Figure 1:
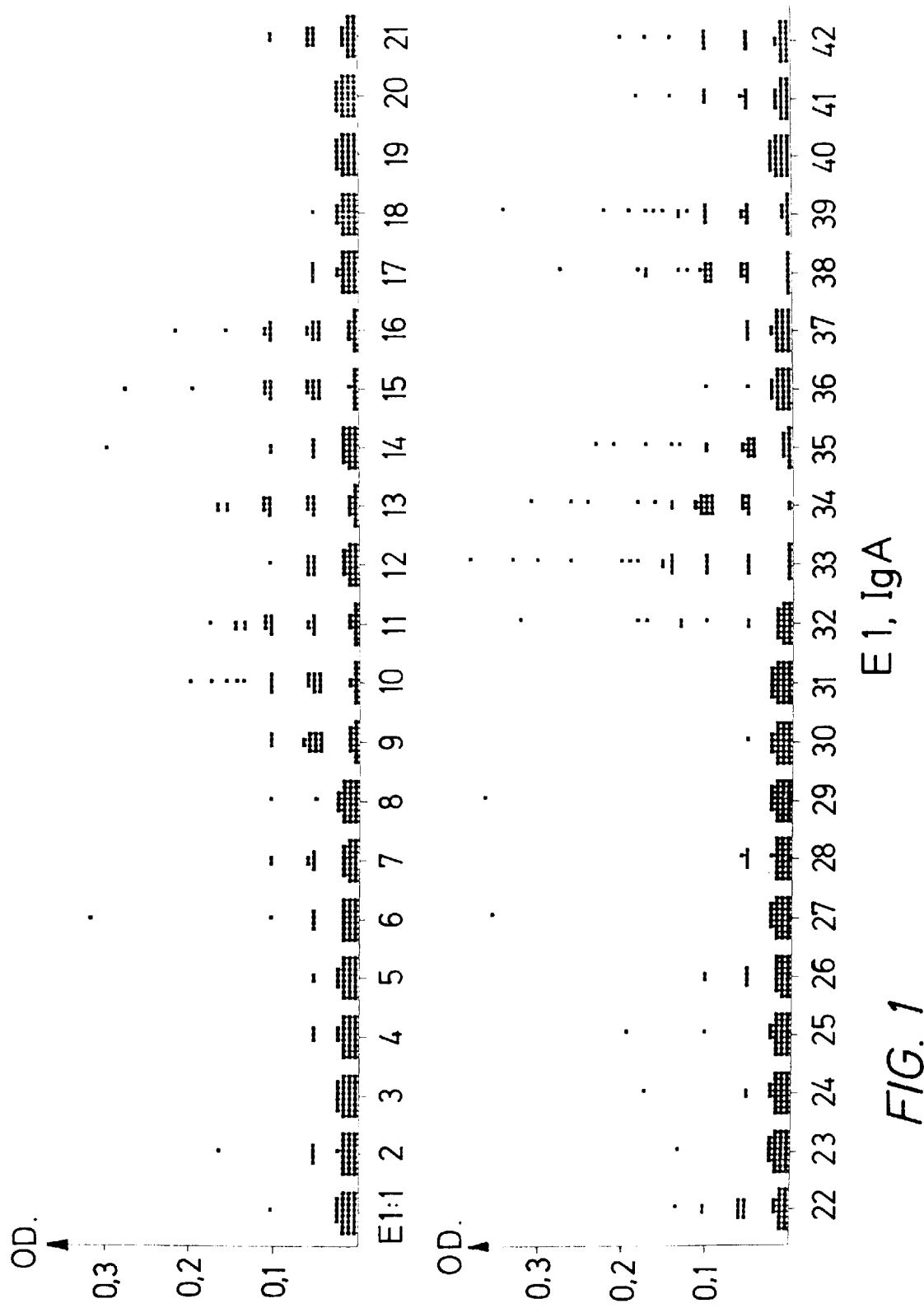

United States Patent [19]
Dillner et al.

[11] Patent Number: 5,932,412
[45] Date of Patent: Aug. 3, 1999

[54] SYNTHETIC PEPTIDES IN HUMAN PAPILLOMAVIRUSES 1, 5, 6, 8, 11, 16, 18, 31, 33 AND 56, USEFUL IN IMMUNOASSAY FOR DIAGNOSTIC PURPOSES

[75] Inventors: Joakim Dillner; Lena Dillner, both of Stockholm, Sweden; Hwee-Ming Cheng, Kuala Lumpur, Malaysia

[73] Assignee: Euro-Diagnostica AB, Malmo, Sweden

[21] Appl. No.: 08/934,915

[22] Filed: Sep. 22, 1997

Related U.S. Application Data

[63] Continuation of application No. 07/949,836, Feb. 22, 1993, abandoned.

[30] Foreign Application Priority Data

May 11, 1990 [SE] Sweden .................................. 9001705

[51] Int. Cl.⁶ .............................. C12G 1/70; G01N 33/53
[52] U.S. Cl. .................................. 435/5; 435/7.1; 436/64; 436/813; 530/321; 530/325; 530/326; 530/388.4; 530/389.4
[58] Field of Search ........................... 435/5, 7.1; 436/64, 436/813; 530/321, 325, 326, 388.3, 389.4

[56] References Cited

U.S. PATENT DOCUMENTS

| | | | |
|---|---|---|---|
| 4,748,109 | 5/1988 | Baird ........................................... | 435/5 |
| 4,777,239 | 10/1988 | Schoolnik et al. ....................... | 530/326 |
| 5,629,146 | 5/1997 | Dillner et al. .............................. | 435/5 |

FOREIGN PATENT DOCUMENTS

| | | | |
|---|---|---|---|
| 16464/83 | 2/1984 | Australia ...................... | G01N 33/570 |
| 30071/84 | 6/1984 | Australia ....................... | G01N 33/54 |
| 0092456 | 10/1983 | European Pat. Off. . | |
| 0243221 | 10/1987 | European Pat. Off. . | |
| 0256321 | 2/1988 | European Pat. Off. ......... | C12N 15/00 |
| 0257754 | 3/1988 | European Pat. Off. .......... | C07K 7/06 |
| 0299354 | 1/1989 | European Pat. Off. ........ | C12P 21/00 |
| 0344940 | 12/1989 | European Pat. Off. . | |
| 0375555 | 6/1990 | European Pat. Off. . | |
| 0386734 | 9/1990 | European Pat. Off. . | |
| 0412762A2 | 2/1991 | European Pat. Off. .......... | C07K 7/06 |
| WO 86/05816 | 10/1986 | WIPO . | |
| WO 87/01375 | 3/1987 | WIPO . | |
| WO 8701375 | 3/1987 | WIPO . | |
| WO 87/05630 | 9/1987 | WIPO . | |
| WO 90/04790 | 5/1990 | WIPO .......................... | G01N 33/570 |

OTHER PUBLICATIONS

Oltersdorf et al. 1987, J. Gneral Virology, vol. 68, pp. 2933–2938.

Doorbar, Chem. Abstr., vol. 107:130591g, p. 395, Oct. 12, 1987.

Li, et al.: "Identification of the Human Papillomavirus Type Bb L1 Open Reading Frame Protein in Condylomas and Corresponding Antibodies in Human Sera"; Journal of Virology B1(9):2684–2690, 1987.

Krisch, I., et al.: "Demonstration of Secretory Component, IgA, IgG, IgM by the Peroxidase—Antiperoxidase Technique in Invested Papillomas of the Nasal Cavities"; Human Pathol. 15(10):915–20 (1984).

Medline, NLM, 86243722 Breast Cancer Res. Treat. 1986, 7(2), pp. 97–103.

Medline, NLM, 87093933 Scand. J., Dent. Res. Oct. 1986, 95(5), pp. 419–426.

Virology, vol. 175, 1990, N.D. Christensen et al.: Immunological Cross–Reactivity to Laboratory–Produced HPV–11 Virions of Polysera Raised against Bacterially Derived Fusion Proteins and Synthetic Peptides of HPV–6b and HPV–16 Capsid Proteins; see p. 1– p. 9. See in particular Table I and Discussion.

The EMBO Journal, vol. 6, No. 1, 1987, K. Seedorf et al.: Identification of early proteins of the human papilloma viruses type 16 (HPV 16) and type 18 (HPV 19) in cervical carcinoma cells. See p. 139—p. 144. See in particular fig. 3.

Int. J. Cancer, vol. 45, 1990, J. Dillner et al.: "Mapping of linear epitopes of human papillomavirus type 16: The L1 and L2 open reading frames"; See p. 529—p. 535. See table 1, peptides 39 and 49.

Proc. Natl. Acad. Sci., vol. 86, May 1989, Joakim Dillner et al.: "A synthetic peptide defines a serologic IgA response to a human papillomavirus–encoded nuclear antigen expressed in virus–carrying cervical neoplasia;" p. 3838, left column and Discussion.

Dialog Information Services, Dataase WPIL, File 351, Accession No. 5195697, TOA NENRYO KOGYO KK: Antibody formed to antigen polypeptide—contains hydrophilic part forming part of initial protein of human papilloma–virus relating to malignant diseases; Examination; JP 1061665 A 890308 8916 (Basic).

J. gen Virol., vol. 70, 1989, D. Patel et al.: Reactivities of Polyclonal and Monoclonal Antibodies Raised to the Major Capsid Protein of Human Papillomavirus Type 16; See p. 69, p. 77. See in particular Table 1 and pp. 76–77.

Dialog Information Services, Medline, File 154, Accession No. 07256206, Steele JC et al: Humoral assays of human sera to disrupted and nondisrupted epitopes of human papillomavirus type 1; Virology Feb. 1990, 174 (2), pp 388–98.

Dialog Information Services, Medline, File 154, Accession No. 06062955, Komly CA et al: "The L2 open reading frame of human papillomavirus type 1a encodes a minor structural protein carrying type–specific antigens"; J Virol (United States), Nov. 1986, 60 (2) pp. 813–6.

(List continued on next page.)

Primary Examiner—Mary E. Mosher
Assistant Examiner—Ali R. Salimi
Attorney, Agent, or Firm—Joseph C. Mason, Jr.; Dennis G. LaPointe

[57] ABSTRACT

The invention refer to a method for diagnosing the presence of infection of papilloma virus (PV) and of papilloma virus (PV) carrying, especially cervix cancer and condyloma, by the detection of virus specific antigen-antibody complexes in immunossay.

5 Claims, 18 Drawing Sheets

OTHER PUBLICATIONS

Dialog Information Services, Medline, File 154, Accession No. 06638652, Doorbar J. et al.: Analysis of HPV–1 E4 gene expression using epitope–defined antibodies; EMBO J, Mar. 1988, 7 (3) pp. 825–33.

J. gen. Virol., vol. 68, 1987, L. Banks, et al.: "Expression of Human Papillomavirus Type 6 and 16 Capsid Proteins in Bacteria and Their Antigenic Characterization"; See p. 3081—p. 3089. See p. 3085, last paragraph—p. 3088, last paragraph.

Virology, vol. 164, 1988, J.M. Firzlaff, et al.: "Detection of Human Papillomavirus Capsid Antigens in Various Squamous Epithelial Lesions Using Antibodies Directed against the L1 and L2 Open Reading Frames"; See p. 467—p. 477.

National Library of Medline (NLM), Database Medline, accession No. 90107938, Barbosa MS et al: "The region of the HPV E7 oncoprotein homologous to adenovirus E1a and Sv40 large T antigen contains separate domains for Rb binding and casein kinase II phosphorylation"; EMBO J 1990, Jan; 9(1):153–60.

National Library of Medline (NLM), Database Medline, accession No. 90171929, Strang G., et al.: "Human T cell responses to human papillomaviurs type 16 L1 and E6 sythetic peptides: identification of T cell determinants, HLA–DR restriction and virus type specificity"; J Gen Virol 1990 Feb; 71 (Pt 2):423–31.

J. gen. Virol., vol. 67, 1986, G. Matlashewski et al.: "The Expression of Human papillomavirus Type 18, E6 Protein in Bacteria and the Production of Anti–E6 Antibodies"; See p. 1909—p. 1916.

J. gen. Virol., vol. 69, 1988, H.M. Browne et al.: "Analysis of the L1 Gene Product of Human Papillomavirus Type 16 by Expression in a Vaccinia Virus Recombinant"; See p. 1263—p. 1273.

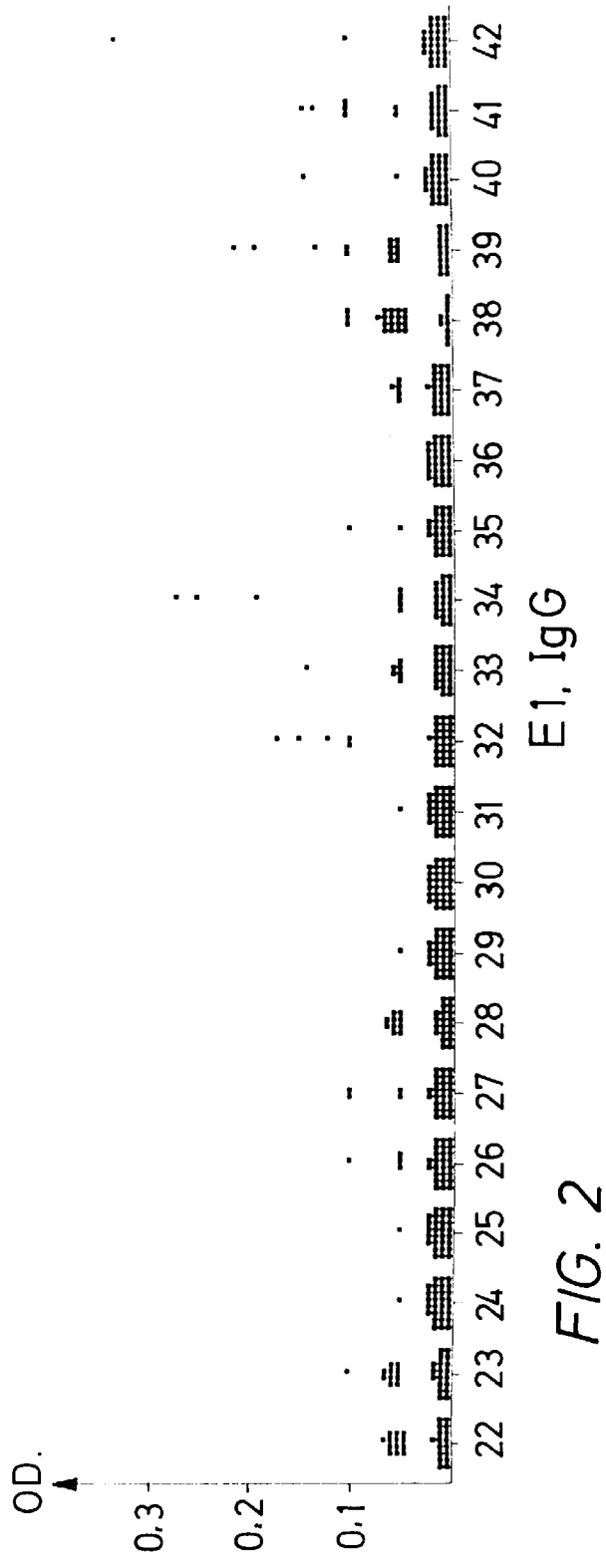
FIG. 2

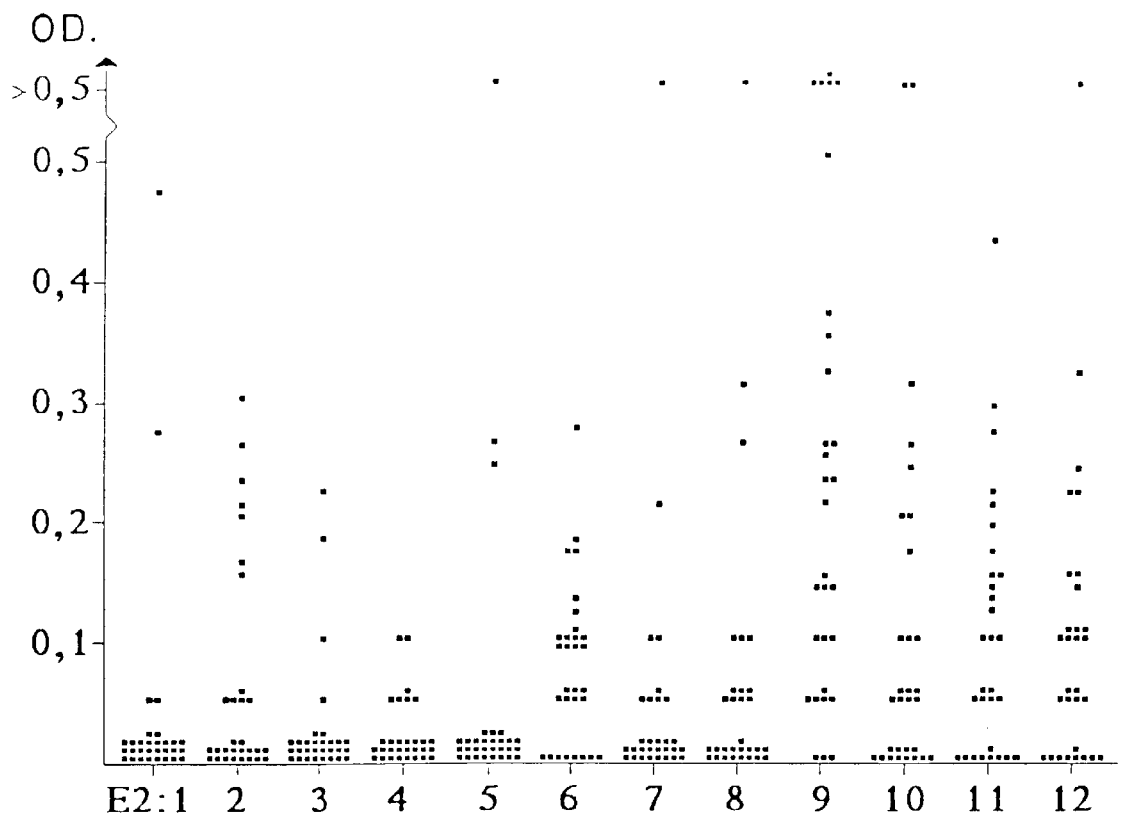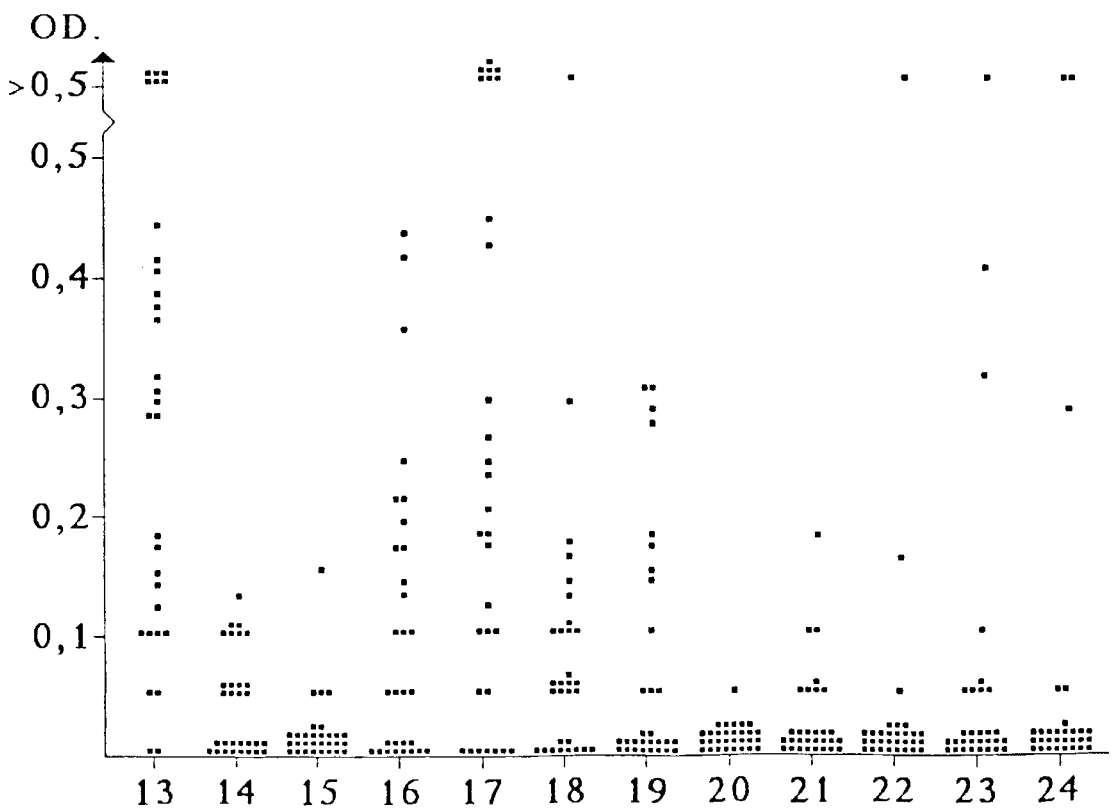
FIG. 4

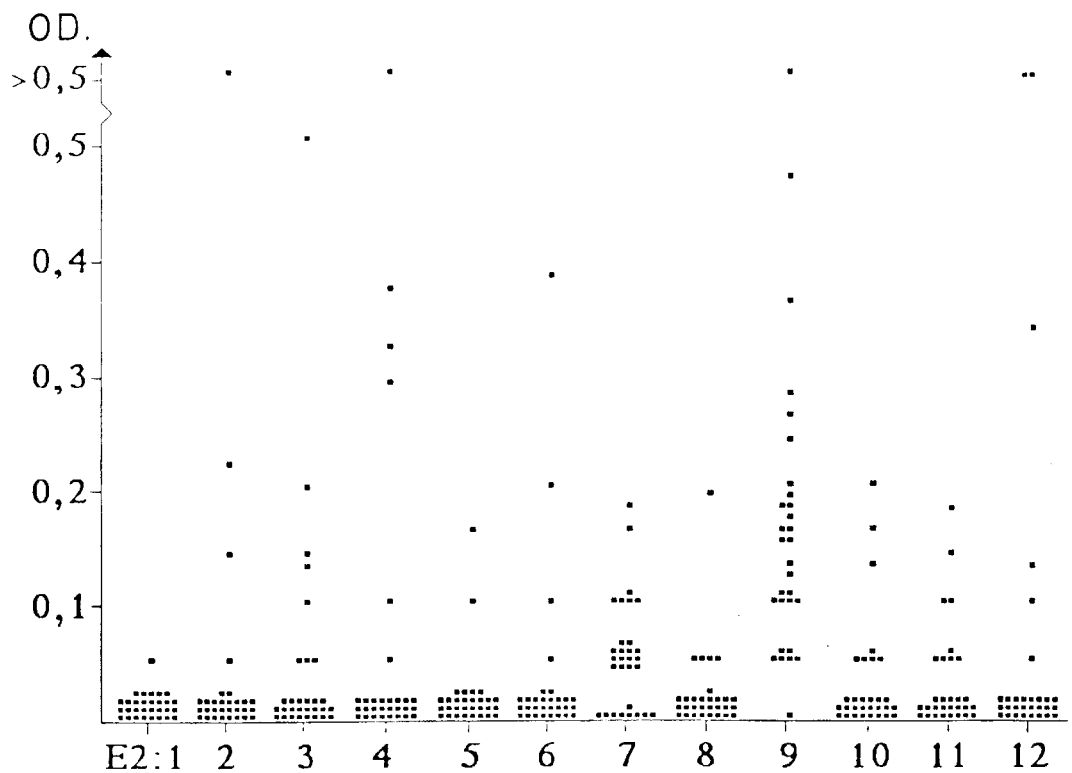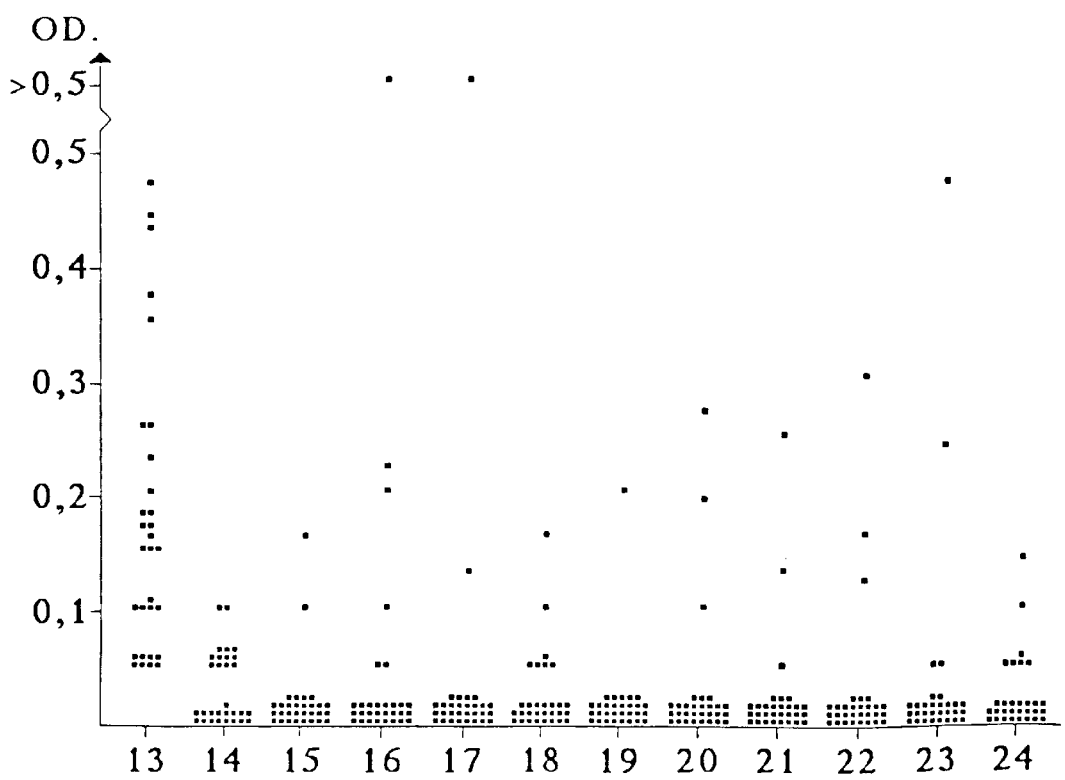
FIG. 5

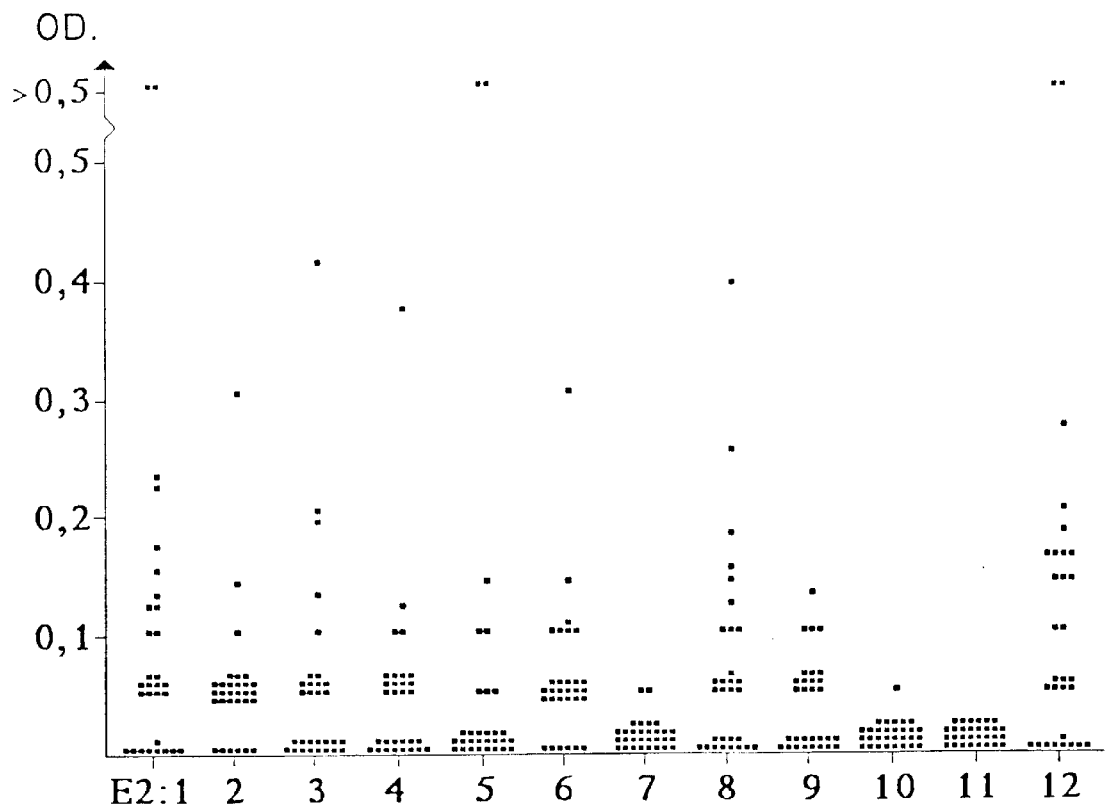
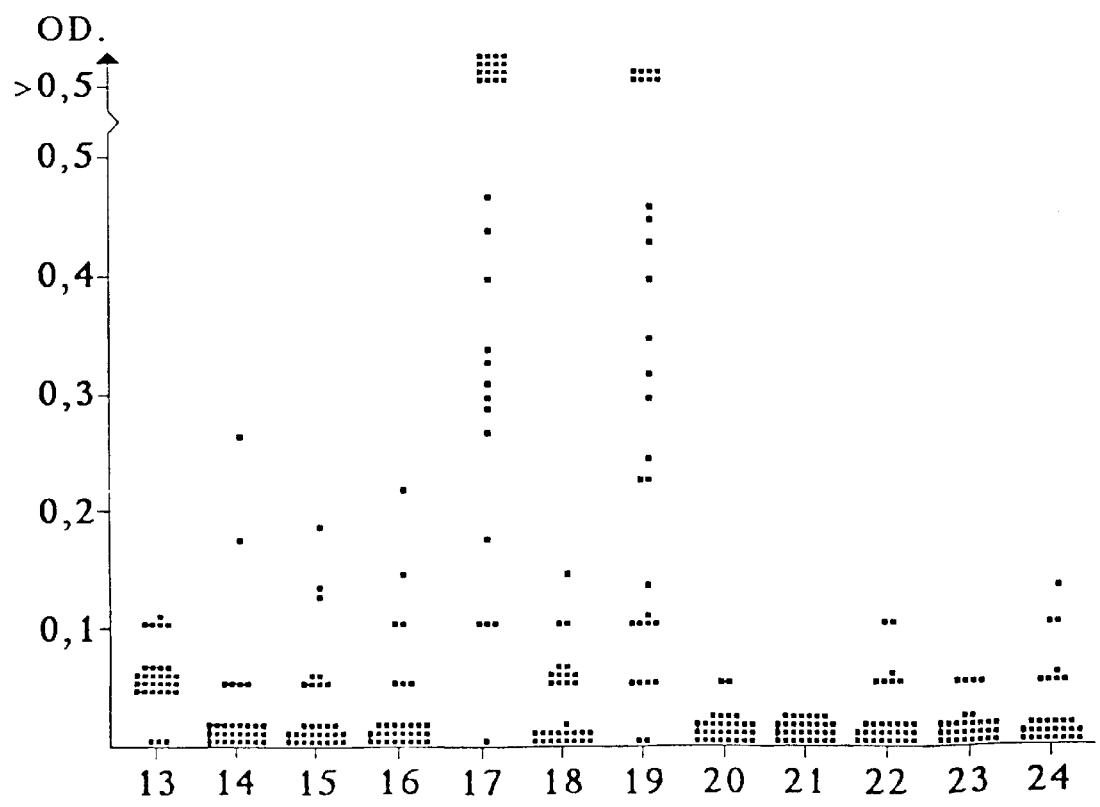
FIG. 6

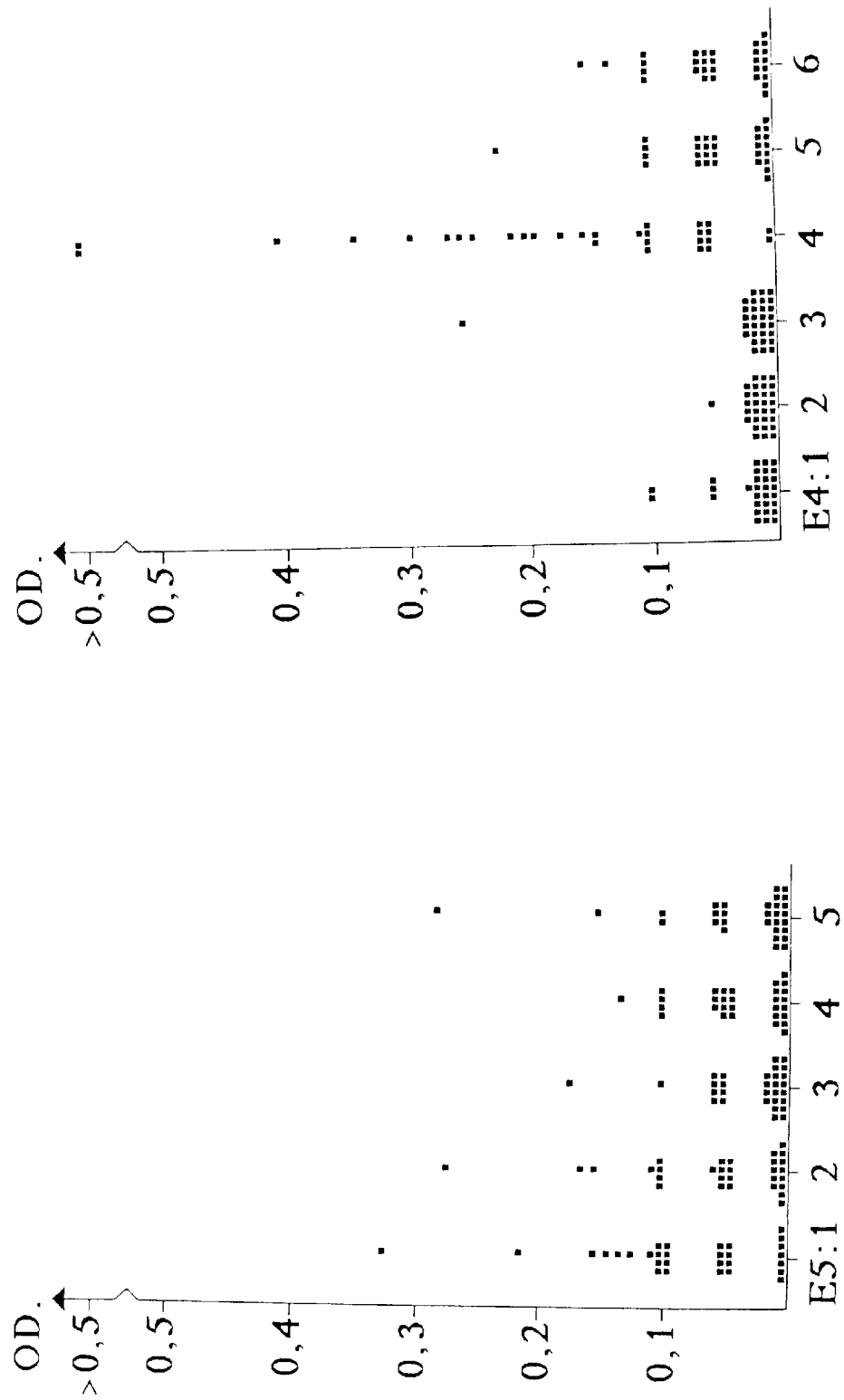

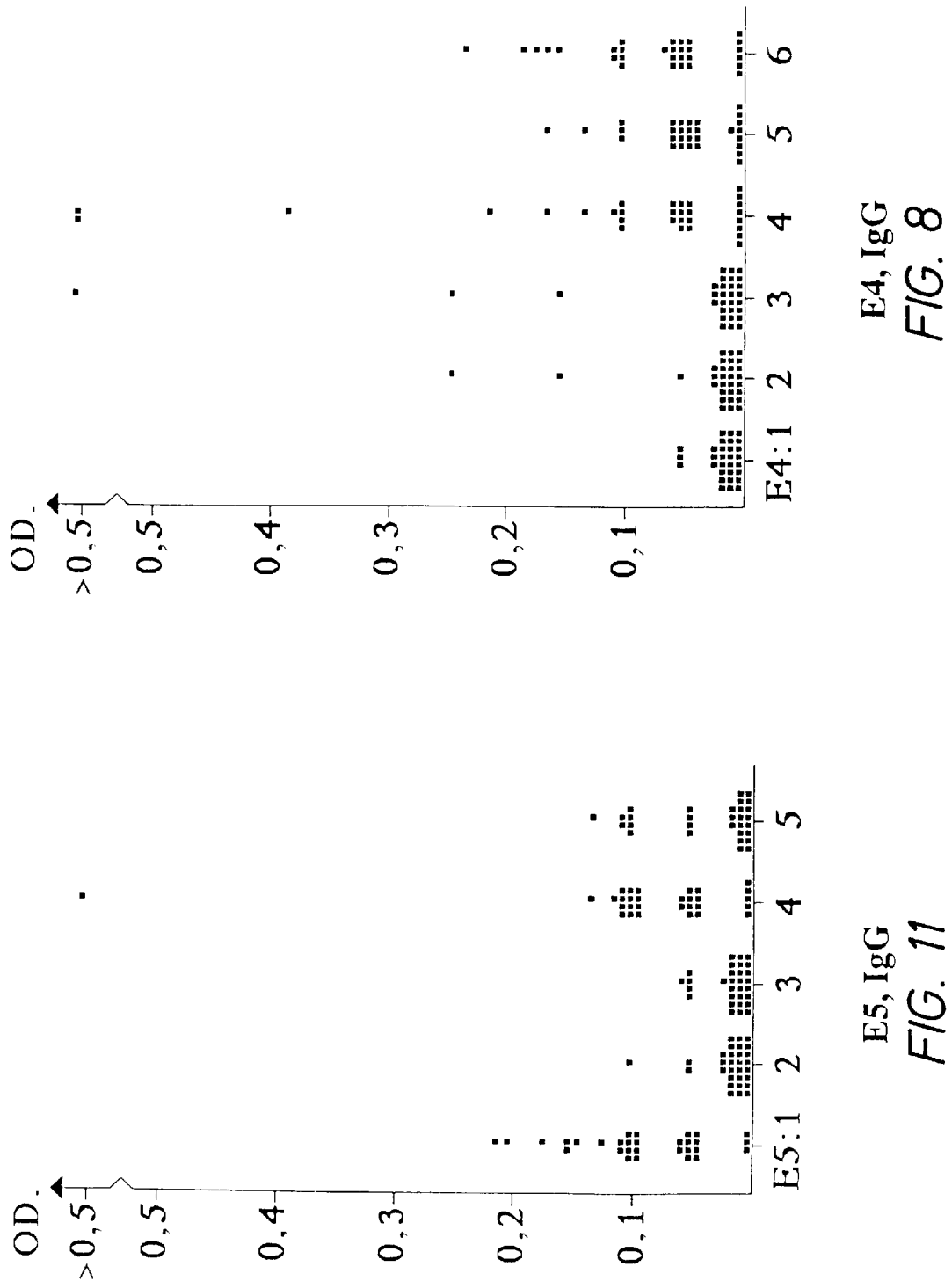

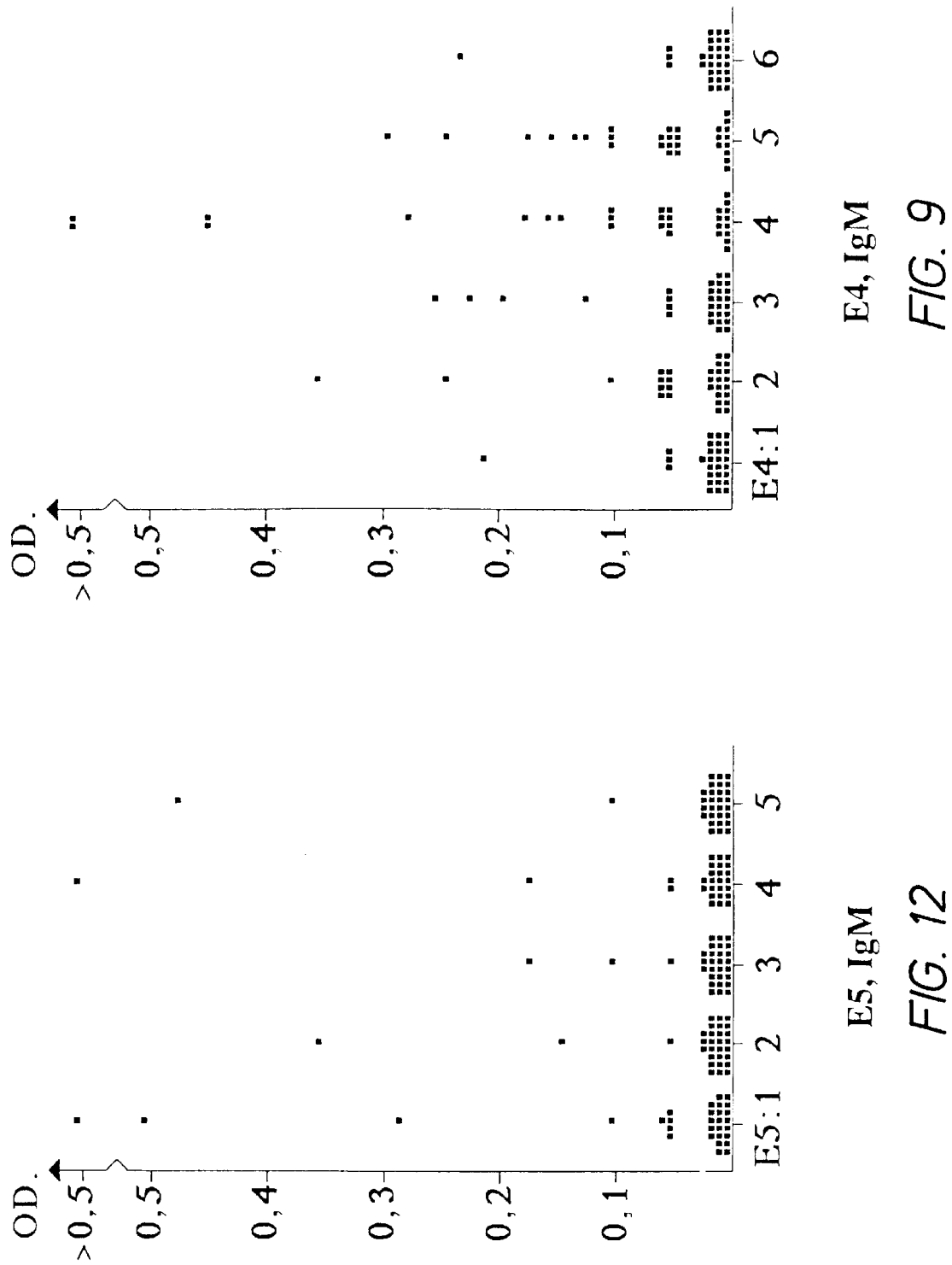

SYNTHETIC PEPTIDES IN HUMAN PAPILLOMAVIRUSES 1, 5, 6, 8, 11, 16, 18, 31, 33 AND 56, USEFUL IN IMMUNOASSAY FOR DIAGNOSTIC PURPOSES

This application is a continuation of application Ser. No. 07/949,836 filed on Feb. 22, 1993, now abandoned.

The invention refers to a method for diagnosing the infection of human papillomavirus (HPV) and of papillomavirus (PV) carrying tumours, especially cervix cancer and condyloma, by the detection of virus specific antigen-antibody complexes in immunoassay. Several new immunoreactive antigens based on the HPV-types 1, 5, 6, 8, 11, 16, 18, 31, 33 and 56, useful for such diagnostics, have been produced by chemical means. Their use and structure is described.

Human papillomavirus is a common virus family which causes proliferative diseases in an infected epithelium. Different types of HPV cause different diseases and appear at different sites in the body. Several types, in particular type 6, 11, 16, 18, 31, 33, 35 and 52, infect the genital region. The HPV types 6 and 11 mainly cause pointed genital warts, known as condyloma acuminata. The types 16, 18, 31, 33, 35, 39, 51 and 55 cause on the other hand mainly flat, almost invisible lesions which are called cervical intraepithelial neoplasia (CIN). These CIN-lesions can develop further to cervix cancer even if comparatively seldom. More than 90% of all cervix cancers carry some type of HPV. HPV 16 alone is found in about 60% of all cervical tumours. HPV 1 causes benign skin tumours, verruca vulgaris or common wart. HPV 5 and HPV 8 cause malignant squamous cell carcinomas in the skin, above all as a part of a state of illness with multiple warts which are called epidermodysplasia verruciformis (EV).

All HPV genome have at least 8 regions which are supposed to code for a protein and are called open reading frames (ORF).These are numbered E1 to E7, L1 and L2. By way of introduction, the reading frames E1, E2, E4, E5, E6 and E7 have been studied in connection with the present invention. Fortyone peptides in all have then been synthesized on the basis of the amino acid sequences for the proteins from E2, E4, E7, L1 or L2 of HPV 1, 5, 6, 8, 11, 16, 18, 31 and 33. The selection of peptide sequences was based on the assumption that an immunoreactive region might be situated in the same relative region of a protein from different HPV types. In this connection, the above described knowledge about the immunoreactive regions of HPV 16 and other known immunoreactive regions within E2, E4, E7, L1 and L2 of HPV 16 were utilized (J. Dillner, L. Dillner, WO 90/04790, Dillner et al., Int. J. Cancer, 45, 529–535, 1990; Dillner, Int. J. Cancer, 46, 703–711, 1990). It is not at all obvious that immunoreactive regions of the other HPV viruses should be located within the same relative regions, and as can be seen below, the successful discovery of immunoreactive regions have been very different for different peptides and different HPV types. Immunoreactive antigens of HPV 16 are known within the reading frames E1, E2, and E6 (J. Dillner et al., Proceedings of the National Academy of Sciences USA, 86, 3838–3841 (1989); J. Dillner, EP,A2 344 940). Additional peptides which likewise originate from HPV 16, reading frames E1, E2, E4, E6 and E7, have been described (G. K. Schoolnik, EP,A2 257 754). Moreover, these have been selected with respect to predicted secondary structure and hydrophilicity. However, these antigens differ from those claimed here.

Schoolnik et al. (EP, A2 257 754) have used a computer algorithm based on hydrophilicity and predicted secondary structure to select peptide sequences for synthesis. W. D. Lancaster presented (in a lecture at the 7th International Papillomavirus meeting, Sophia Antopolis, France, May 1988) the use of a computer algorithm to select sequences in the L1 protein of BPV-1 and BPV-2 that were either poorly conserved or exhibited homology between these BPV types. It must be emphasized that in no instance was any type of computer algorithm or other previously described methods used for peptide selection in the present invention.

The reading frame E7 of HPV 16 is 84 amino acids long and has been synthesized as a 84 amino acid long peptide (Reeves et al., Lancet, i, 551–552, 1990) and as a fusion protein produced in bacteria (Jochmus-Kudielka et al., J. Nat. Cancer Inst., 81, 1698–1704, 1989). The costs for producing such long peptides are,. however, very high and it is in addition technically difficult to accomplish and the shorter E7 peptides described here are consequently a considerable improvement.

An object of the invention is to provide a method of detecting especially cervix cancer in a cheaper and more easy way. Furthermore, it was intended to find peptides based on ORF E7, which should be more immunoreactive and at the same time considerably shorter and thus cheaper and more easy to produce than the earlier described 84 amino acid long peptides. The object has been further developed to find synthetic peptides based on other medically important papilloma viruses than the earlier studied HPV 16. In the present invention we describe immunoreactive peptides from HPV 1, 5, 6, 8, 11, 16, 18, 31, 33 and 56.

In order to achieve said purpose the method of the invention has obtained the characterizing features of claim 1.

Figure 3:
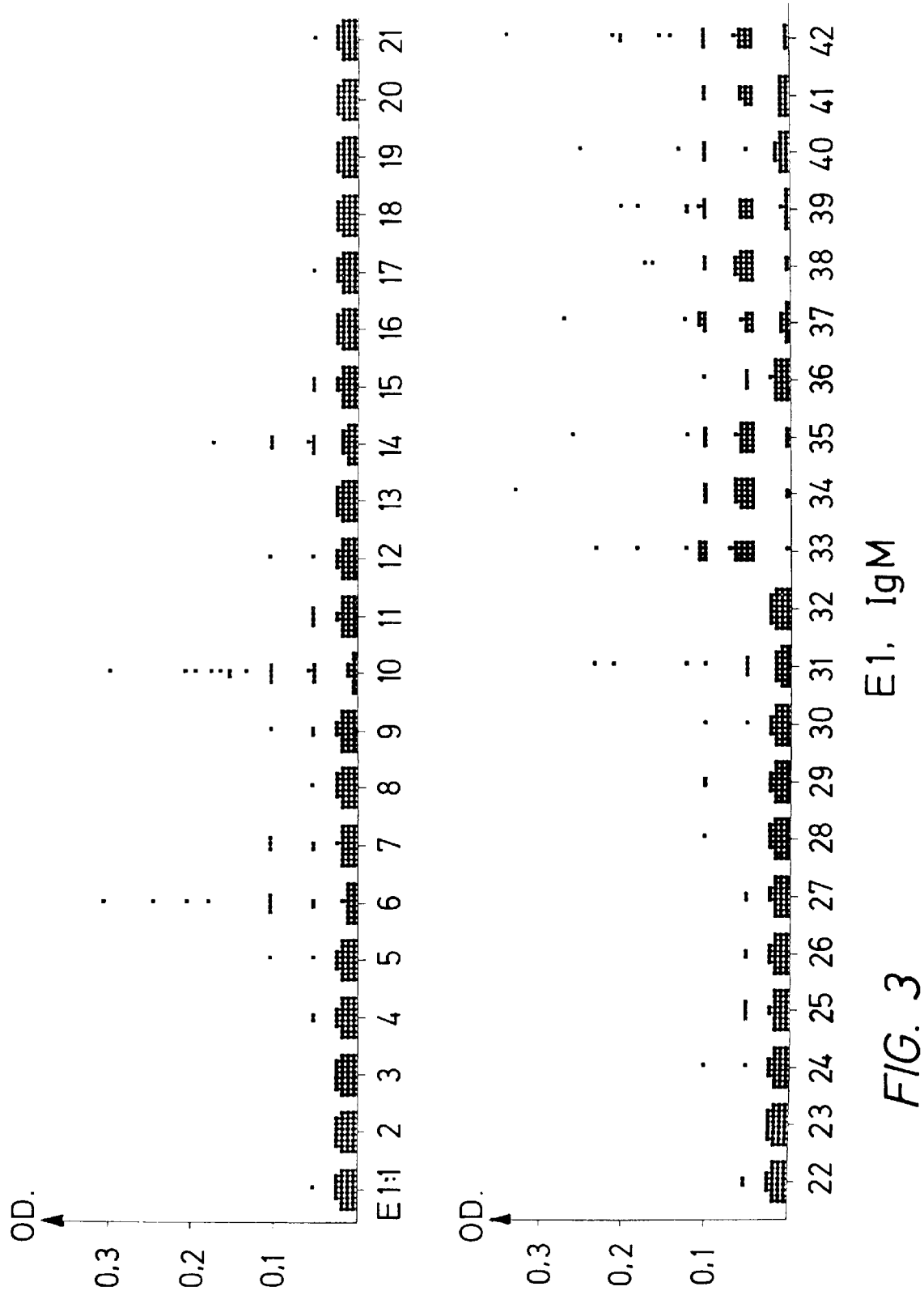
Figure 13:
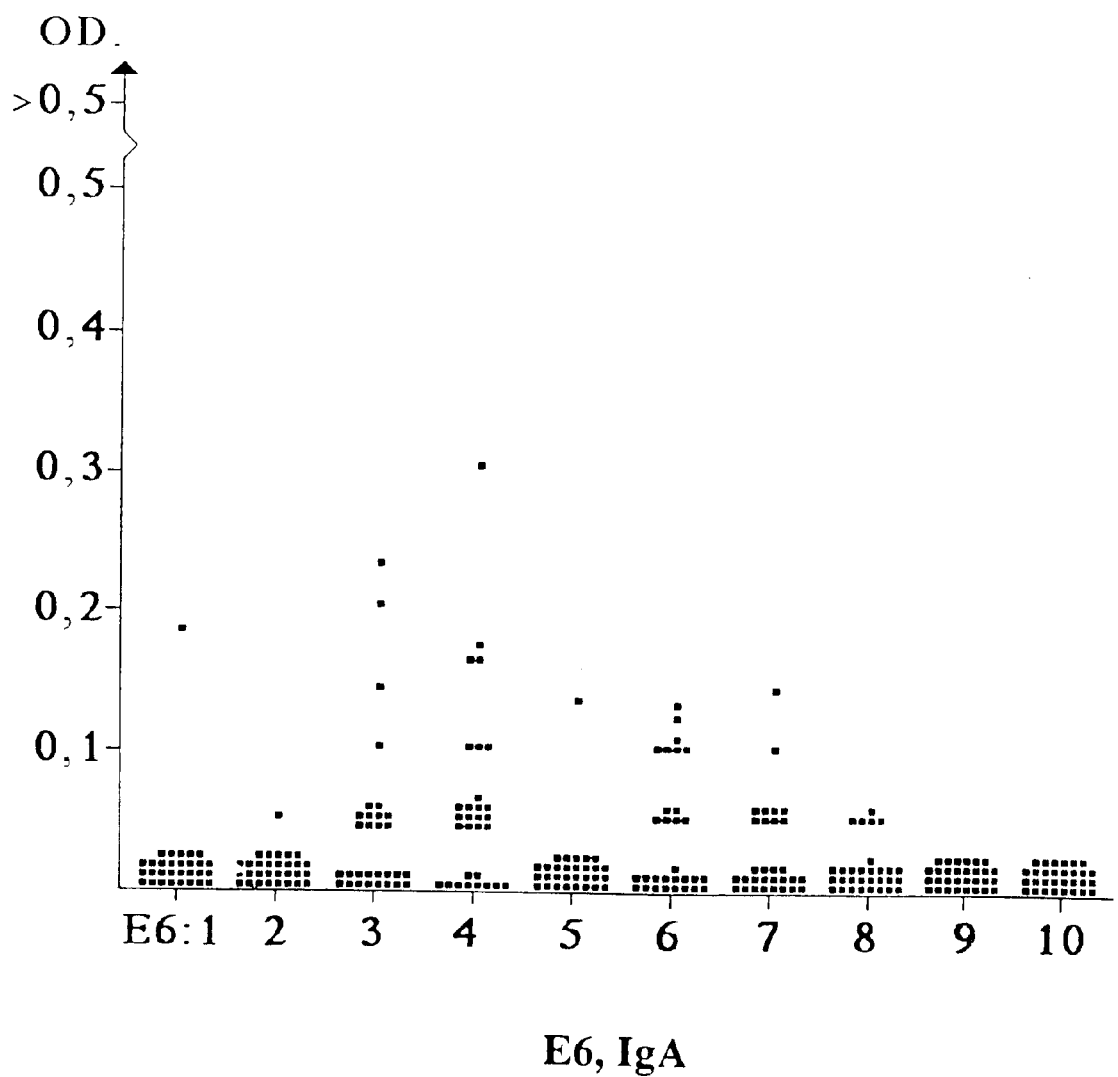
Figure 14:
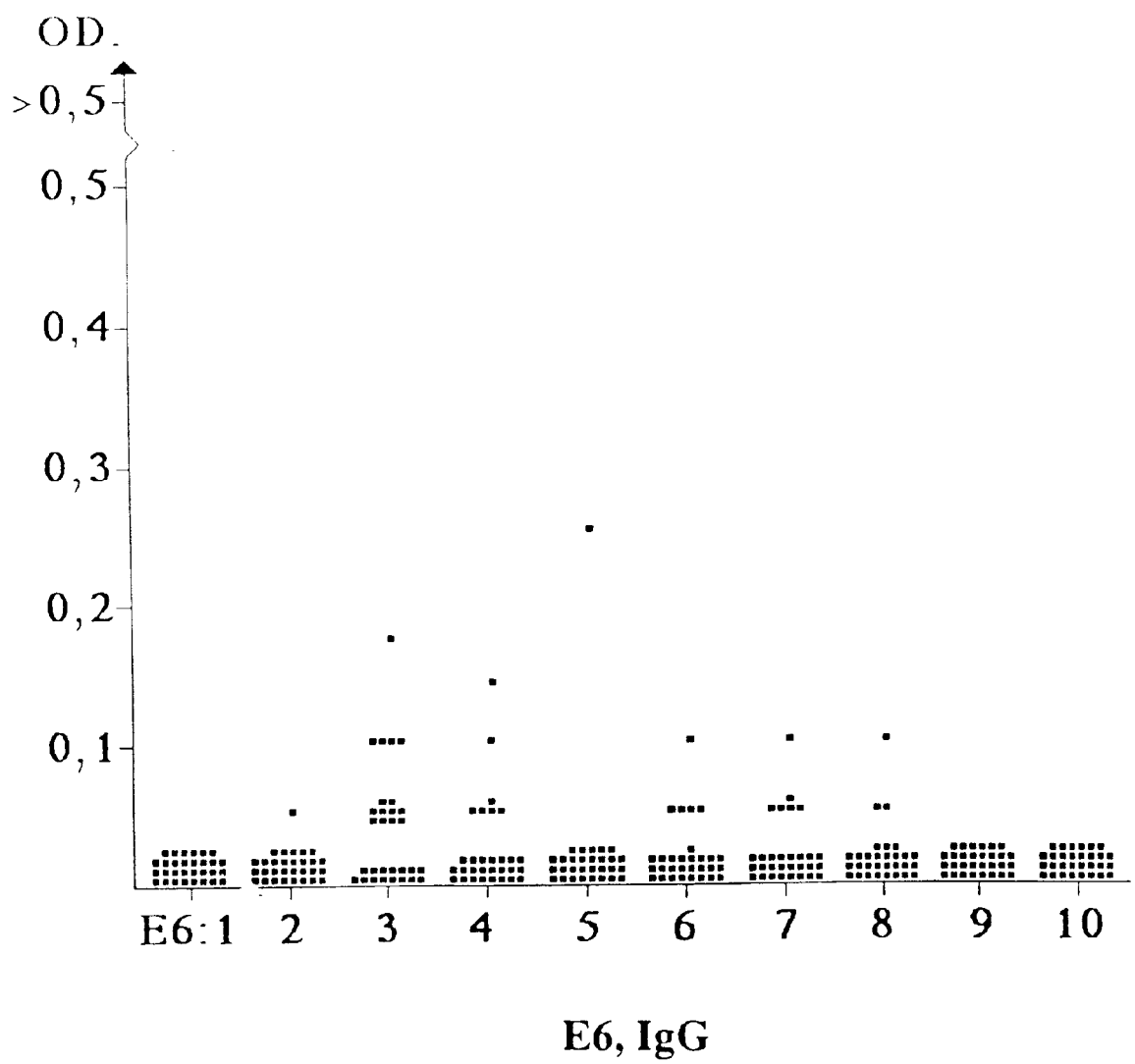
Figure 15:
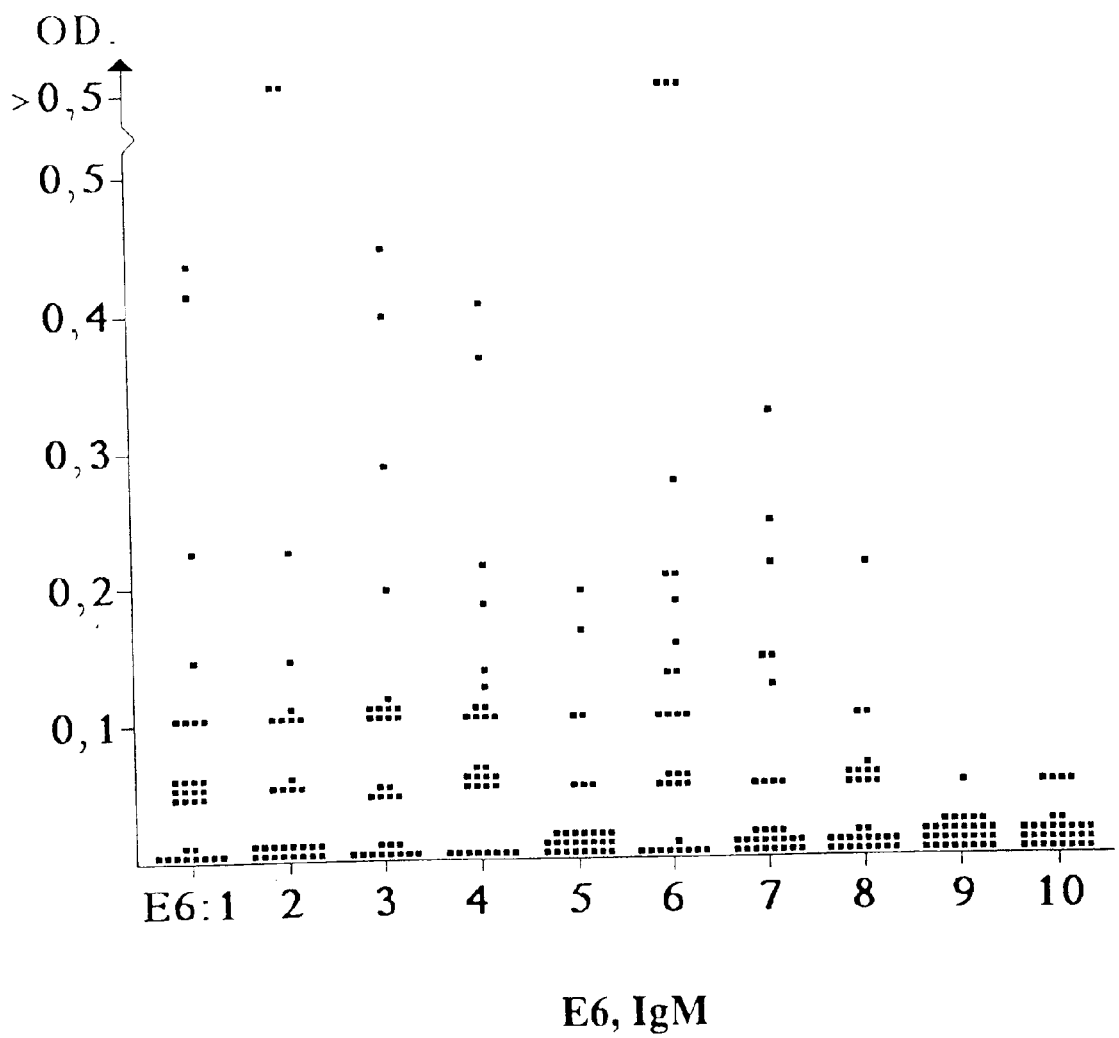
Figure 16:
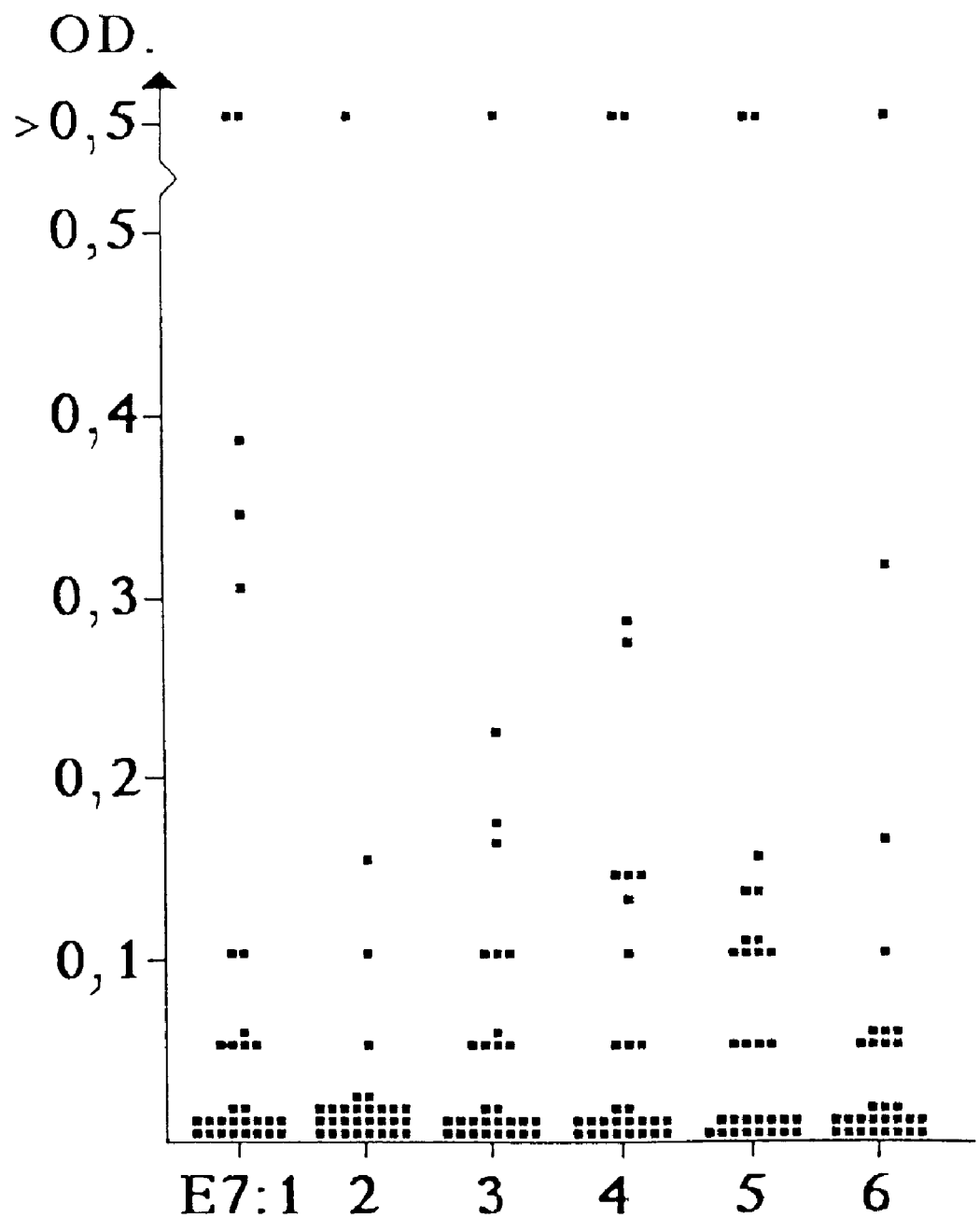
Figure 17:
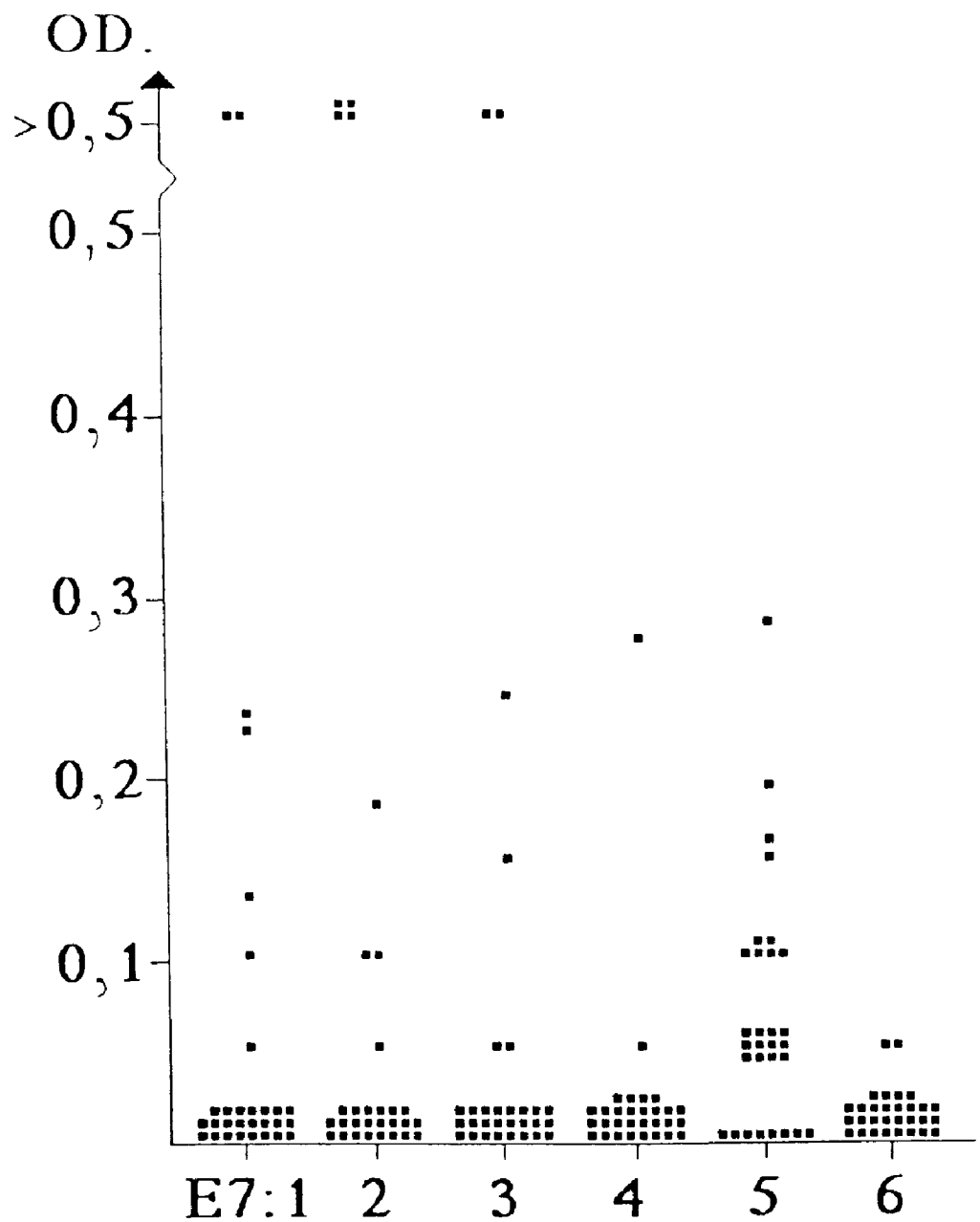
Figure 18:
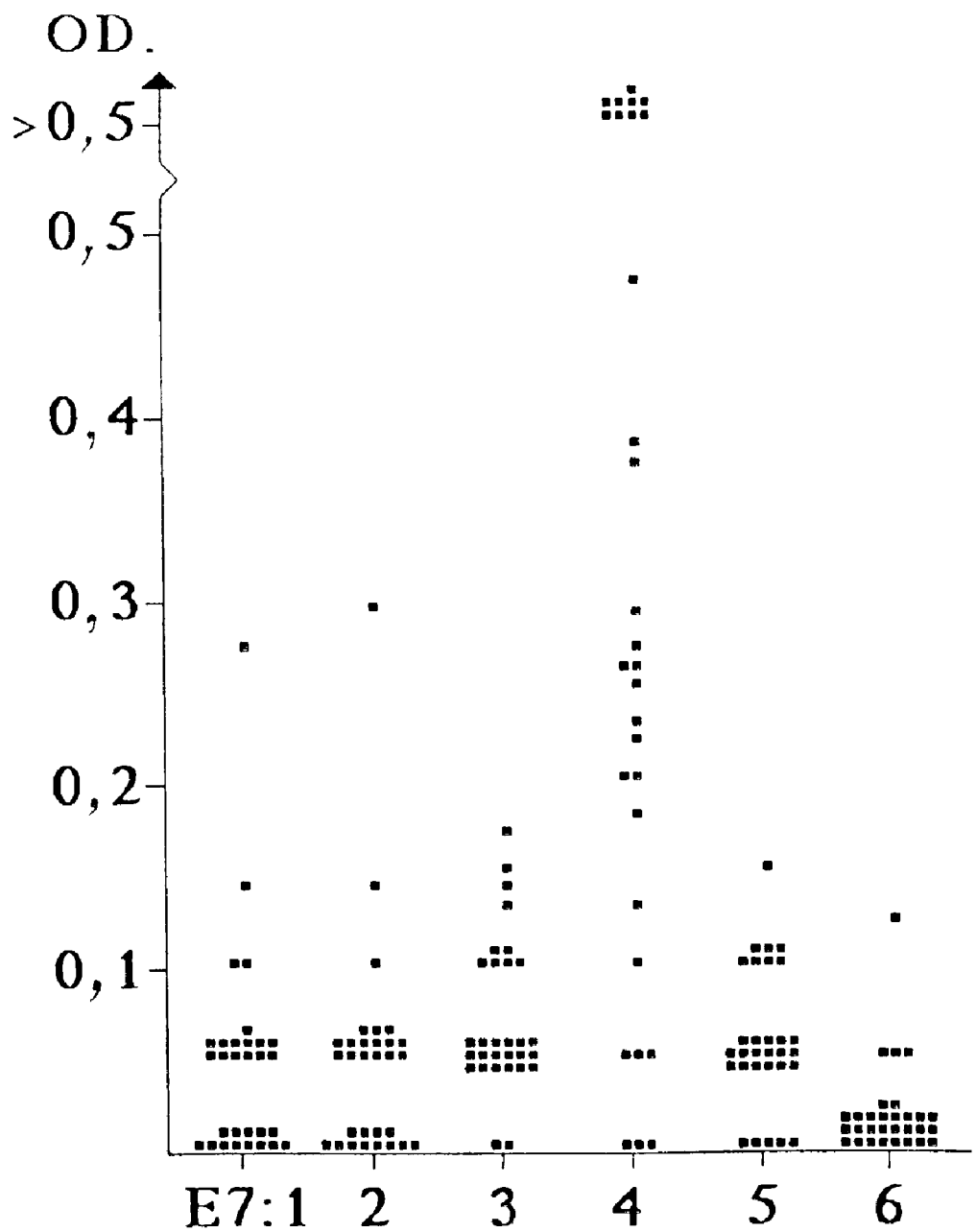
Figure 19:
Figure 20:
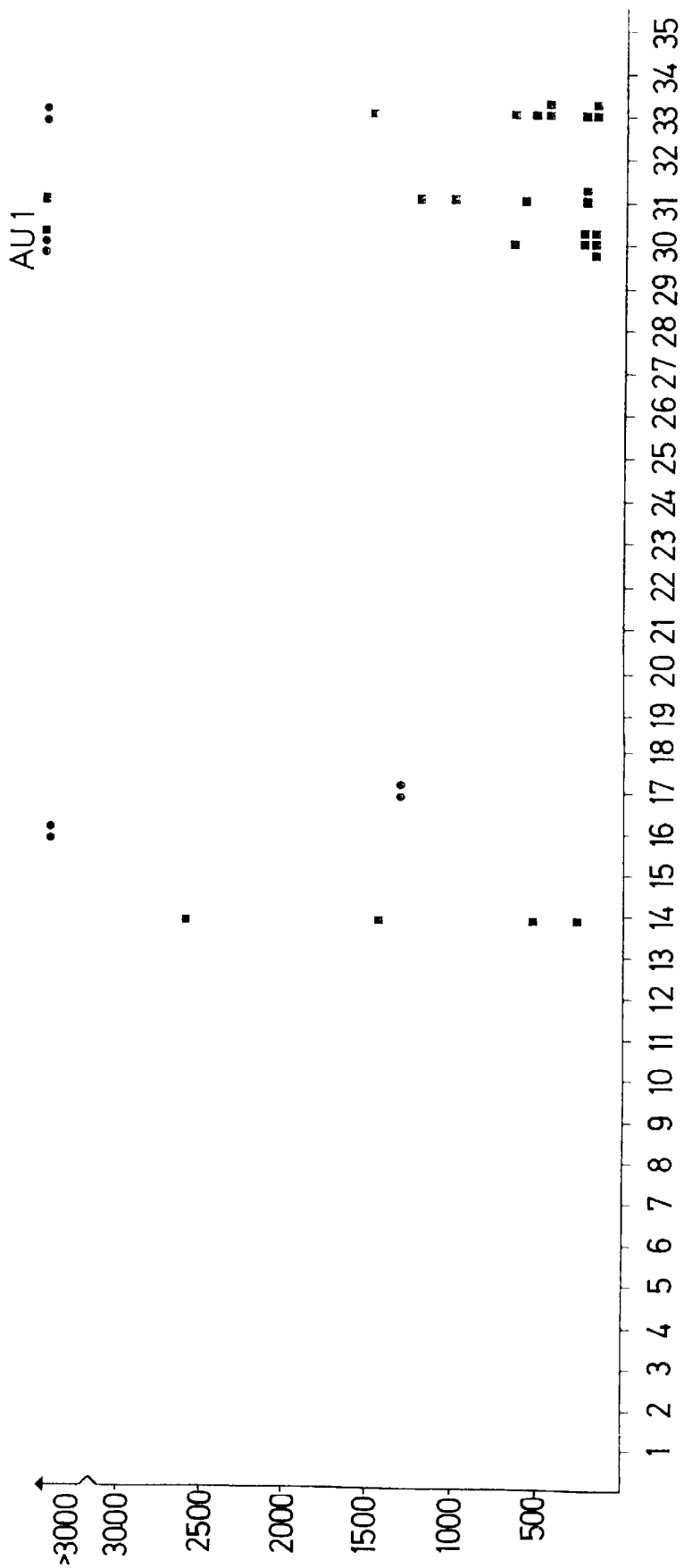
Figure 21:
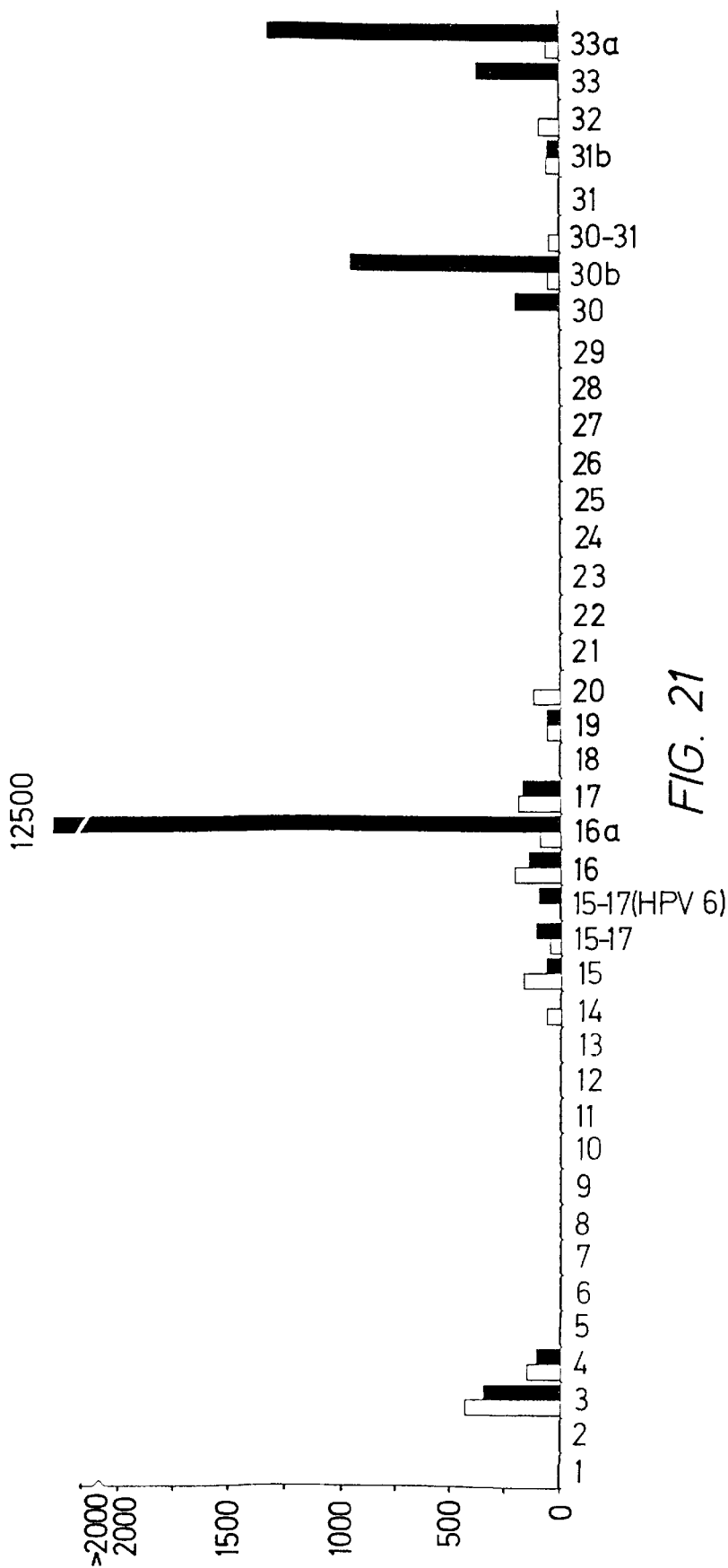

The invention will now be further explained below with reference to the accompanying drawings, in which FIG. 1 shows the IgA reactivity of 30 sera from patients with cervix cancer against 42 overlapping 20 amino acid peptides corresponding to the total sequence of human papillomavirus type 16 (HPV 16), ORF E1, FIG. 2 shows the IgG reactivity of 30 sera from patients with cervix cancer against 42 overlapping 20 amino acid peptides corresponding to the total sequence of human papillomavirus type 16 (HPV 16), ORF E1, FIG. 3 shows the IgM reactivity of 30 sera from patients with cervix cancer against 42 overlapping 20 amino acid peptides corresponding to the total sequence of human papillomavirus type 16 (HPV 16), ORF E1, FIG. 4 shows the IgA reactivity of 30 sera from patients with cervix cancer against 24 overlapping 20 amino acid peptides corresponding to the total sequence of human papillomavirus type 16 (HPV 16), ORF E2, FIG. 5 shows the IgG reactivity of 30 sera from patients with cervix cancer against 24 overlapping 20 amino acid peptides corresponding to the total sequence of human papillomavirus type 16 (HPV 16), ORF E2, FIG. 6 shows the IgM reactivity of 30 sera from patients with cervix cancer against 24 overlapping 20 amino acid peptides corresponding to the total sequence of human papillomavirus type 16 (HPV 16), ORF E2, FIG. 7 shows the IgA reactivity of 30 sera from patients with cervix cancer against 6 overlapping 20 amino acids peptides corresponding to the total. sequence of human papillomavirus type 16 (HPV 16), ORF E4, FIG. 8 shows the IgG reactivity of 30 sera from patients with cervix cancer against 6 overlapping 20 amino acids peptides corresponding to the total sequence of human papillomavirus type 16 (HPV 16), ORF E4, FIG. 9 shows the IgM reactivity of 30 sera from patients with cervix cancer against 6 overlapping 20 amino acid peptides corresponding to the total sequence of human papillomavirus type 16 (HPV 16), ORF E4, FIG. 10 shows the IgA reactivity of 30 sera from patients with cervix cancer against 5 overlapping 20 amino acid peptides corresponding to the total sequence of human papillomavirus type 16 (HPV 16), ORF E5, FIG. 11 shows the IgG reactivity of 30 sera from patients with cervix cancer against 5 overlapping 20 amino acid peptides corresponding to the total sequence of human papillomavirus type 16 (HPV 16), ORF E5, FIG. 12 shows the IgM reactivity of 30 sera from patients with cervix cancer against 5 overlapping 20 amino acid peptides corresponding to the total sequence of human papillomavirus type 16 (HPV 16), ORF E5, FIG. 13 shows the IgA reactivity of 30 sera from patients with cervix cancer against 10 overlapping 20 amino acid peptides corresponding to the total sequence of human papillomavirus type 16 (HPV 16), ORF E6, FIG. 14 shows the IgG reactivity of 30 sera from patients with cervix cancer against 10 overlapping 20 amino acid peptides corresponding to the total sequence of human papillomavirus type 16 (HPV 16), ORF E6, FIG. 15 shows the IgM reactivity of 30 sera from patients with cervix cancer against 10 overlapping 20 amino acid peptides corresponding to the total sequence of human papillomavirus type 16 (HPV 16), ORF E6, FIG. 16 shows the IgA reactivity of 30 sera from patients with cervix cancer against 6 overlapping 20 amino acid peptides corresponding to the total sequence of human papillomavirus type 16 (HPV 16), ORF E7, FIG. 17 shows the IgG reactivity of 30 sera from patients with cervix cancer against 6 overlapping 20 amino acid peptides corresponding to the total sequence of human papillomavirus type 16 (HPV 16), ORF E7, FIG. 18 shows the IgM reactivity of 30 sera from patients with cervix cancer against 6 overlapping 20 amino acid peptides corresponding to the total sequence of human papillomavirus type 16 (HPV 16), ORF E7, FIG. 19 shows a comparison between the immunoreactivities of 30 sera from patients with cervix cancer and 60 sera from healthy persons against 4 of the examined peptides, FIG. 20 shows the mapping of papillomavirus group-specific epitopes, and FIG. 21 shows the generation of group specific antisera by immunization with synthetic peptides.

PEPTIDE SYNTHESIS

The polypeptides were produced synthetically and the the following formula are stated for denoting the amino acids in the synthetic peptides.

In Table 1 below the symbols indicate amino acids according to the following:

| SYMBOL | AMINO ACID |
|---|---|
| Y | L-tyrosine |
| G | glycine |
| F | L-phenylalanine |
| M | L-methionine |
| A | L-alanine |
| S | L-serine |
| I | L-isoleucine |
| L | L-leucine |
| T | L-threonine |
| V | L-valine |
| P | L-proline |

-continued

| SYMBOL | AMINO ACID |
|---|---|
| K | L-lysine |
| H | L-histidine |
| Q | L-glutamine |
| E | L-glutamic acid |
| W | L-tryptophan |
| R | L-arginine |
| D | L-aspartic acid |
| N | L-asparagine |
| C | L-cysteine |

The different amino acids used for peptide synthesis had been deduced from the nucelotide sequences of the open reading frames L1, L2, E2, E4 and E7 of the HPV types 1, 5, 6, 8, 11, 16, 18, 31 and 33. The peptide synthesis was performed with t-Boc amino acids (Bachyem, Bubendorf, Schweiz) and a p-methylbenzhydrylamine resin (Fluka, Buchs, Schweiz) according to an earlier published method (Houghten, Proceedings of the National Academy of Sciences USA, 82, 5131–5153 1985). The protecting groups of formyltryptophan and methionine sulphoxide were removed by treatment with 25% hydrofluoric acid and the peptides were then detached from the resin by liquid hydrofluoric acid. Since all peptides were synthesized on a p-methylbenzhydrylamine resin, all peptides contain an amide group on their carboxyterminal end.

| No. | SEQ ID NO: | Sequence |
|---|---|---|
| | OPEN READING FRAME E 5 | |
| 1 | SEQ ID NO:81 | TNLDTASTTLLACFLLCFCV |
| 2 | SEQ ID NO:82 | LCFCVLLCVCLLIRPLLLSV |
| 3 | SEQ ID NO:83 | LLLSVSTYTSLIILVLLLWI |
| 4 | SEQ ID NO:84 | LLLWITAASAFRCFIVYIIF |
| 5 | SEQ ID NO:85 | VYIIFVYIPLFLIHTHARFLIT |
| | OPEN READING FRAME E 1 | |
| 1 | SEQ ID NO:86 | ADPAGTNGEEGTGCNGWFYV |
| 2 | SEQ ID NO:87 | GWFYVEAVVEKKTGDAISDD |
| 3 | SEQ ID NO:88 | AISDDENENDSDTGEDLVDF |
| 4 | SEQ ID NO:89 | DLVDFIVNDNDYLTQAETET |
| 5 | SEQ ID NO:90 | AETETAHALFTAQEAKQHRD |
| 6 | SEQ ID NO:91 | KQHRDAVQVLKRKYLGSCIE |
| 7 | SEQ ID NO:92 | GSCIEKQSRAAKRRLFESED |
| 8 | SEQ ID NO:93 | FESEDSGYGNTEVETQQMLQV |
| 9 | SEQ ID NO:94 | LQVEGRHETETPCSQYSGG |
| 10 | SEQ ID NO:95 | QYSGGSGGGCSQYSSGSGGE |
| 11 | SEQ ID NO:96 | GSGGEGVSERHTICQTPLTN |
| 12 | SEQ ID NO:97 | TPLTNILNVLKTSNAKAAML |
| 13 | SEQ ID NO:98 | KAAMLAKFKELYGVSFSELV |
| 14 | SEQ ID NO:99 | FSELVRPFKSNRSTCCDWCI |
| 15 | SEQ ID NO:100 | CDWCIAAFGLTPSIADSIKT |
| 16 | SEQ ID NO:101 | DSIKTLLQQYCLYLHIQSLA |
| 17 | SEQ ID NO:102 | IQSLACSWGMVVLLLVRYKC |
| 18 | SEQ ID NO:103 | VRYKCGKNRETIEKLLSKLL |
| 19 | SEQ ID NO:104 | LSKLLCVSPMCMMIEPPKLR |
| 20 | SEQ ID NO:105 | PPKLRSTAAALYWYKTGISN |
| 21 | SEQ ID NO:106 | TGISNISEVYGDTPEWIQRQ |
| 22 | SEQ ID NO:107 | WIQRQTVLQHSFNDCTFELS |
| 23 | SEQ ID NO:108 | TFELSQMVQWAYDNDIVDDS |
| 24 | SEQ ID NO:109 | IVDDSEIAYKYAQLADTNSN |
| 25 | SEQ ID NO:110 | DTNSNASAFLKSNSQAKIVK |
| 26 | SEQ ID NO:111 | AKIVKDCATMCRHYKRAEKK |
| 27 | SEQ ID NO:112 | RAEKKQMSMSQWIKYRCDRV |
| 28 | SEQ ID NO:113 | RCDRVDDGGDWKQIVMFLRY |
| 29 | SEQ ID NO:114 | MFLRYQGVEFMSFLTALKRF |
| 30 | SEQ ID NO:115 | ALKRFLQGIPKKNCILLYGA |
| 31 | SEQ ID NO:116 | LLYGAANTGKSLFGMSLMKF |
| 32 | SEQ ID NO:117 | SLMKFLQGSVICFVNSKSHF |
| 33 | SEQ ID NO:118 | SKSHFWLQPLADAKIGMLDD |
| 34 | SEQ ID NO:119 | GMLDDATVPCWNYIDDNLRN |
| 35 | SEQ ID NO:120 | DNLRNALDGNLVSMDVKHRP |

-continued

| No. | SEQ ID NO: | Sequence |
|---|---|---|
| 36 | SEQ ID NO:121 | VKHRPLVQLKCPPLLITSNI |
| 37 | SEQ ID NO:122 | ITSNINAGTDSRWPYLHNRL |
| 38 | SEQ ID NO:123 | LHNRLVVFTFPNEFPFDENG |
| 39 | SEQ ID NO:124 | FDENGNPVYELNDKNWKS |
| 40 | SEQ ID NO:125 | KNWKSFFSRTWSRLSLHE |
| 41 | SEQ ID NO:126 | LSLHEDEDKENDGDSLPT |
| 42 | SEQ ID NO:127 | DSLPTFKCVSGQNTNTL |

OPEN READING FRAME E 2

| | | |
|---|---|---|
| 1 | SEQ ID NO:128 | ETLCQRLNVCQDKILTHYE |
| 2 | SEQ ID NO:129 | LTHYENDSTDLRDHIDYWKH |
| 3 | SEQ ID NO:130 | DYWKHMRLECAIYYKAREMG |
| 4 | SEQ ID NO:131 | AREMGFKHINHQVVPTLAVS |
| 5 | SEQ ID NO:132 | TLAVSKNKALQAIELQLTLE |
| 6 | SEQ ID NO:133 | QLTLETIYNSQYSNEKWTLQ |
| 7 | SEQ ID NO:134 | KWTLQDVSLEVYLTAPTGCI |
| 8 | SEQ ID NO:135 | PTGCIKKHGYTVEVQFDGDI |
| 9 | SEQ ID NO:136 | FDGDICNTMHYTNWTHIYIC |
| 10 | SEQ ID NO:137 | HYICEEASVTVVEGQVDYY |
| 11 | SEQ ID NO:138 | QVDYYGLYYVHEGIRTYFVQ |
| 12 | SEQ ID NO:139 | TYFVQFKDDAEKYSKNKVWE |
| 13 | SEQ ID NO:140 | NKVWEVHAGGQVILCPTSVF |
| 14 | SEQ ID NO:141 | PTSVFSSNEVSSPEIIRQHL |
| 15 | SEQ ID NO:142 | IRQHLANHPAATHTKAVALG |
| 16 | SEQ ID NO:143 | AVALGTEETQTTIQRPRSEP |
| 17 | SEQ ID NO:144 | PRSEPDTGNPCHTTKLLHRD |
| 18 | SEQ ID NO:145 | LLHRDSVDSAPILTAFNSSH |
| 19 | SEQ ID NO:146 | FNSSHKGRINCNSNTTPIVH |
| 20 | SEQ ID NO:147 | TPIVHLKGDANTLKCLRYRF |
| 21 | SEQ ID NO:148 | LRYRFKKHCTLYTAVSSTWH |
| 22 | SEQ ID NO:149 | SSTWHWTGHNVKHKSAIVTL |
| 23 | SEQ ID NO:150 | AIVTLTYDSEWQRDQFLSQV |
| 24 | SEQ ID NO:151 | FLSQVKIPKTITVSTGFMSI |

OPEN READING FRAME E 7

| | | |
|---|---|---|
| 1 | SEQ ID NO:152 | HGDTPTLHEYMLDLQPETTD |
| 2 | SEQ ID NO:153 | PETTDLYCYEQLNDSSEEED |
| 3 | SEQ ID NO:154 | SEEEDEIDGPAGQAEPDRAH |
| 4 | SEQ ID NO:155 | PDRAHYNIVTFCCKCDSTLR |
| 5 | SEQ ID NO:156 | DSTLRLCVQSTHVDIRTLEDL |
| 6 | SEQ ID NO:157 | TLEDLLMGTLGIVCPICSQKP |

OPEN READING FRAME E 6

| | | |
|---|---|---|
| 1 | SEQ ID NO:158 | HQKRTAMFQDPQERPRKLPQ |
| 2 | SEQ ID NO:159 | RKLPQLCTELQTTIHDIILE |
| 3 | SEQ ID NO:160 | DIILECVYCKQQLLRREVYD |
| 4 | SEQ ID NO:161 | REVYDFAFRDLCIVYRDGNP |
| 5 | SEQ ID NO:162 | RDGNPYAVCDKCLKFYSKIS |
| 6 | SEQ ID NO:163 | YSKISEYRHYCYSLYGTTLE |
| 7 | SEQ ID NO:164 | GTTLEQQYNKPLCDLLIRCI |
| 8 | SEQ ID NO:165 | LIRCINCQKPLCPEEKQRHL |
| 9 | SEQ ID NO:166 | KQRHLDKKQRFHNIRGRWTGR |
| 10 | SEQ ID NO:167 | RWTGRCMSCCRSSRTRRETQL |

OPEN READING FRAME E 4

| | | |
|---|---|---|
| 1 | SEQ ID NO:168 | YYVLHLCLAATKYPLLKLLG |
| 2 | SEQ ID NO:169 | LKLLGSTWPTTPPRPIPKPS |
| 3 | SEQ ID NO:170 | IPKPSPWAPKKHRRLSSDQD |
| 4 | SEQ ID NO:171 | SSDQDQSQTPETPATPLSCC |
| 5 | SEQ ID NO:172 | PLSCCTETQWTVLQSSLHLT |
| 6 | SEQ ID NO:173 | SLHLTAHTKDGLTVIVTLHP |

Preparation of Peptide Antisera

The peptides were coupled to the carrier protein KLH (Keyhole limpet hemocyanin, an oxygen transport protein from a marine gastropod, Sigma, St Louis, Mo. USA) by using maleimidobenzoyl-n-hydroxysuccinimide ester (MBS) for peptides containing cysteine or glutardialdehyde for the others. In this connection, 4 mg peptide was coupled to 4 mg KLH. The reaction mixture with KLH was dialyzed against 10 mM phosphate buffer, pH 6, and 85 µl of 4 mg/ml MBS dissolved in dimethylformamide was then added and was allowed to react for 30 minutes. KLH-MBS was then separated from free MBS by gel filtation on a column of Sepahdex G-25 (Pharmacia, Upsala, Sweden) and the synthetic peptide was added and allowed to react for 15 hours at room temperature. When coupling with glutardialdehyde, KLH was dialyzed against PBS and 4 mg KLH was then mixed with 4 mg synthetic peptide. 200 µl of 25% glutardialdehyd (Merck, Darmstadt, Germany) was added to 13 ml PBS. Then 260 µl of this diluted glutardialdehyde solution was added to the mixture of peptide and KLH and the reaction was allowed to proceed for 15 hours at room temperature. Finally, 100 mM Tris-HCl, pH 7.5, was added. When guinea pigs were immunized, 100 µg of the coupled peptide was injected subcutaneously. At the first immunization the peptide was suspended in 1 ml of Freunds complete adjuvant (Difco). Two weeks later and after another two weeks the animals were given 100 µg of coupled peptide in Freunds incomplete adjuvant (Difco) was administered. The animals were bled two weeks after the last immunization.

Sera

Sera used for immunoassays were obtained from patients with HPV 16-carrying cervix cancer and from healthy controls.

Collection of Cervical Secretions

A small brush (Cytobrush, Medscand, Malmö, Sweden) was rotated over the endo and exocervix and then the brush was placed in a small vial with 1 ml of phosphate buffered saline containing 5 mM ethylenedinitrilotetraacetic acid, penicilline, streptomycine and amphotericin B. The vial was mixed on a Vortex mixer and centrifuged at 5000 rpm for 10 minutes. The brush was removed and the supernatant, containing cervical secretions, was aspirated. The secretions obtained by this method were diluted 1:2 in 10% lamb serum/phosphate buffered saline before they were used in ELISA.

IMMUNOASSAYS

ELISA

The synthetic peptides were diluted to 20 µg/ml in 10 mM carbonate buffer, pH 9.6, and kept for 15 hours at room temperature or, alternatively, for 72 hours at +4° C. in 50 µl/hole ELISA plates (Costar, Cambridge, Mass. USA). After a washing with phosphate buffered saline (PBS) containing 0.05% Tween 20 (PBS-T), the plates were blocked with 10% lamb serum in PBS (LS-PBS) for 60 minutes at 37° C. or, alternatively, for 4 hours at room temperature. Human sera were diluted 1:30 or, alternatively, 1:20 in LS-PBS, and added to the plate whereupon the mixture was incubated f or 120 minuters at 37° C. After 5 washes with PBS-T, a monoclonal antibody against IgA, labelled with peroxidase (Janssen Beerse, Belgium) and diluted 1:500 or, alternatively, 1:200 in LS-PBS, was added. After 5 washes with PBS-T, 0.4 mg/ml of 2,2,-azino-di(3-ethylbenzthiazoline-sulfonate) diammonium salt (ABTS) in 0.1 M citrate buffer, pH 4, containing 0.9% hydrogen peroxide was added and the plate was incubated for 60 minutes. The absorbance of the liberated colour from the reaction was recorded at 415 nm in a spectrophotometer (Titertek, Flow). After 2 washings with PBS-T and blocking with LS-PBS as described above, a rabbit antibody against human IgG, labelled with alkaline phosphatase (Dako, Copenhagen, Denmark) and diluted 1:1000 in LS-PBS, was added and the mixture was incubated for 120 minutes at 37° C. After 5 washings with PBS-T, 1 mg/ml of para-nitrophenylphosphate in 0.1 M diethanolamine buffer, pH 9.6, containing 1 mM MgCl$_2$ was added and the mixture was incubated for 90 minutes at room temperature. The absorbance of the liberated colour from the reaction was recorded at 405 nm in a spectrophotometer (Titertek, Flow). The plates were then washed twice with PBS-T, blocked with LS-PBS as described above and a goat antibody against human IgM, labelled with glucose oxidase (Sera-lab, England) and diluted 1:800 in LS-PBS, was then added and the mixture was incubated for 120 minutes at 37° C. After 5 washings with PBS-T, 0.36 mg/ml of ABTS, 2.4% glucose and 8 μg/ml peroxidase in 0.1 M phosphate buffer, pH 6.0, was added. The absorbance of the liberated colour from the reaction was recorded after 60 minutes at 405 nm in a spectrophotometer (Titertek, Flow). In every test 30 sera were allowed to react with the earlier described reactive peptide His Lys Ser Ala Ile Val Thr Leu Thr Tyr Asp Ser Glu Trp Gln Arg Asp Gln Cys, SEQ ID NO:80 as an internal standard and the absorbances were adjusted compared to the internal standard in order to eliminate variations in the results between different experiments.

Immunofluorescence

Cells of an established cell line of mouse fibroblasts, which had been transfected with HPV type 16, and, as a control, cells of the same cell line, which did not harbour HPV 16 (NIH 3t3), were allowed to grow on a glass slide and were then fixed in 50% acetone/50% methanol at −20° C. for 10 minutes. After blocking of the slides with 10% goat serum in PBS (GS-PBS) for one hour, guinea pig antisera against the different peptides, diluted 1:4 in GS-PBS, were added and the mixture was incubated for 15 hours at room temperature. The slides were immersed 60 times in PBS, 15 μg/ml of goat anti-guinea pig IgG, labelled with biotin (Vector, Burlingame, Calif. USA) in GS-PBS, was added and the mixture was incubated for 45 minutes at room temperature. After 60 immersions in PBS, Avidin labelled with fluorescein isothiocyanate (Dako, Copenhagen, Denmark) at a concentration of 10 μg/ml in a solution of 300 mM NaCl and 10 mM Tris-HCl was added and the mixture was incubated for 30 minutes at room temperature. After 60 immersions in PBS, the specimens were mounted in 50% glycerol and the fluorescent reactivity was determined in a fluorescence microscope (Leitz, Wetzlar, Germany).

Immunohistocytochemistry

Four micron thick sections of formalin fixated and paraffin imbedded preparations of cervix tissue, infected with HPV 16, HPV 6 or HPV 11, on glass slides were immersed in xylene, absolute ethanol, 95% ethanol, 80% ethanol, 50% ethanol and, finally, PBS. Peroxidase activity was extinguished by an immersion for 15 minutes in 3% hydrogen peroxide in PBS and the slides were then blocked with 10% goat serum in PBS (GS-PBS) for one hour. Guinea pig antisera against the different peptides, diluted 1:100 and 1:200 in GS-PBS, were added and allowed to react far 15 hours at room temperature. After 60 immersions in PBS, 15 μg/ml of goat-anti guinea pig-IgG, labelled with biotin (Vector, Burlingame, Calif. USA) in GS-PBS, was added and the mixture was incubated for 45 minutes at room temperature. After 60 immersions in PBS, Avidin labelled with peroxidase (Vector, Burlingame, Calif. USA) in PBS was added and the mixture was incubated for 30 minutes. After 60 immersions in PBS, the slides were immersed for 30 minutes in a solution of 200 ml 0.1 M acetate buffer, pH 5, containing 50 mg aminoethyl carbazole, 4 ml dimethyl formamide and 80 μl 30% hydrogen peroxide. After 20 immersions in PBS the slides were immersed for 10 seconds in Mayer's haematoxylin and then again immersed 60 times in PBS. The specimens were then mounted with 50% glycerol and examined under a light microscope (Leitz, Wetzlar, Germany).

Results

All peptides were tested in ELISA for reactivity with IgA, IgG or IgM antibodies in human sera. Peptides from HPV 16, reading frame E1, E2, E4, E5, E6 and E7 were all tested against a panel of 30 sera from patients with HPV-carrying cervix cancer. IgA reactivity against E1 peptides could first of all be detected with peptides from the carboxyterminal part of E1, FIG. 1. The reactivity was comparatively low with the peptide E1:33 (SEQ ID NO:118) as the only peptide which was reactive with a majority of the sera.

Only low IgG reactivity was obtained with a minority of the sera, FIG. 2. Even the most IgG reactive peptide, E1:39 (SEQ ID NO:124), did only react with 20% of the sera. Some IgH reactivity was also found with peptides in the carboxy-terminal region of E1, FIG. 3, and two peptides, E1:6 (SEQ ID NO:91) and E1:10 (SEQ ID NO:95), in the aminoterminal region of E1. The reading frame E2 was the most reactive of all HPV reading frames. 11 out of 24 peptides were IgA reactive with 25% or more of the sera from patients with cervix cancer. The three most reactive peptides, E2:9 SEQ ID NO:136, E2:13 SEQ ID NO:140, and E2:17 SEQ ID NO:144, were IgA reactive with 70% or more of the sera from patients with cervix cancer, FIG. 4. The IgG reactivity was somewhat lesser but two peptides, E2:9 SEQ ID NO:136 and E2:13 SEQ ID NO:140, were reactive with as much as 77 and 73%, respectively, of the cervix cancer sera, FIG. 5. One of the peptides which were very reactive with IgA, peptide E2:17 SEQ ID NO:144, was not reactive with IgG to any appreciable extent. The IgM reactive peptides from E2 differed to a large extent from the IgA and IgG reactive peptides, FIG. 6. For example, the IgA reactive peptides E2:9 SEQ ID NO:136 and E2:13 SEQ ID NO:140 were not appreciably IgM reactive, while the peptide E2:17 SEQ ID NO:144 reacted with IgA and IgM but not with IgG.

The reading frame E4 contained a main epitope for IgA antibodies, peptide E4:4 SEQ ID NO:171, FIG. 7. This peptide was also the most important E4 epitope for IgG and IgM antibodies, FIGS. 8 and 9. IgG reactivity was also found with peptide E4:6 SEQ ID NO:173 at the carboxy-terminal end of E4.

The reading frame E5 contained only one epitope worth mentioning, E5:1 SEQ ID NO:163, at the aminoterminal end of E5, which had some reactivity with IgA, IgG as well as IgM, FIGS. 10, 11 and 12.

Nor was the reading frame E6 particularly imunnoreactive. Comparatively low IgA and IgG reactivities were noted, FIGS. 13 and 14. However, several peptides were IgM reactive with the peptide E6:6 SEQ ID NO:163 as the most reactive (47% of the sera from patients with cervix cancer), FIG. 15.

The immunoreactivity of the E7 peptides were unusual. For IgG as well as IgA, a small portion (10–20%) of the sera exhibited extremely potent reactivity, FIGS. 16 and 17. These comparatively unusual but strong reactivities were obtained for more peptides along the total E7, FIGS. 16 and 17. The IgM reactivity against the E7 peptides were dominated by peptide E7:4 SEQ ID NO:155, FIG. 18.

Ten of the most reactive peptides were also tested with a panel of 60 sera from healthy persons who then ought to have a smaller portion of and neither as active HPV 16 infections as the cervix cancer group. The absorbance values from ELISA for the two groups were compared with respect to statistically significant differences with a Mann-Whitney test. Most of these 10 peptides were also little reactive with the control sera as shown in Table 2 below.

TABLE 2

| Peptide | IgA >0.1[1] SCC | Co | p-value[2] | IgG >0.1 SCC | Co | p-value | IgM >0.1 SCC | Co | p-value |
|---|---|---|---|---|---|---|---|---|---|
| E1:33 SEQ ID NO:118 | 63% | 37% | <0.02 | 3% | 2% | NS | 40% | 20% | NS |
| E1:39 | 43% | 18% | NS | 20% | 0% | <0.0001 | 30% | 8% | <0.0001 |
| E2:9 SEQ ID NO:136 | 70% | 62% | <0.01 | 76% | 82% | NS | 13% | 12% | NS |
| E2:13 SEQ ID NO:140 | 87% | 68% | <0.0001 | 73% | 47% | <0.0005 | 17% | 20% | NS |
| E2:17 SEQ ID NO:144 | 70% | 55% | <0.01 | 7% | 5% | NS | 97% | 78% | NS |
| E2:19 SEQ ID NO:146 | 30% | 20% | NS | 3% | 2% | NS | 80% | 80% | NS |
| E4:4 SEQ ID NO:171 | 67% | 30% | <0.0001 | 37% | 28% | NS | 37% | 37% | NS |
| E6:6 SEQ ID NO:163 | 23% | 13% | NS | 3% | 2% | NS | 47% | 28% | <0.02 |
| E7:1 SEQ ID NO:152 | 23% | 2% | <0.0002 | 20% | 8% | <0.03 | 13% | 2% | NS |
| E7:4 SEQ ID NO:155 | 30% | 2% | <0.0002 | 3% | 2% | NS | 80% | 75% | NS |

[1]Percent of sera which gives an absorbance value from ELISA of more than 0.1 in the group with cervical carcinoma (SCC) or in the control group (Co).
[2]The numerals indicate the p-values for an significant increase in the absorbances in the group with cervical carcinoma. Notice that the p-valves are not based on the percentage of positive sera but on a non-parametric method (Mann-Whitney-test) of the actual absorbances.
NS = Not significant In several cases, however, very steep increases of antibody titers against these peptides were obtained with patients with cervix cancer compared with the healthy persons as is evident from Table 2 and FIG. 19. The IgG reactivities against the peptides E2:13 (SEQ ID NO:140), E7:1 (SEQ ID NO:152) and E1:39 (SEQ ID NO:124) as well as the IgA reactivities against E2:9 (SEQ ID NO:136), E2:13 (SEQ ID NO:140), E2:17 (SEQ ID NO:144), E7:1 (SEQ ID NO:152); E7:4 (SEQ ID NO:155) and E4:4 (SEQ ID NO:171) should especially be mentioned. According to Table 2, the IgM reactivities were tumour associated only in a couple of cases.

Ninety-four peptides (all from E1, E2, E4, E5, E6 and E7) were also coupled to a carrier protein and used for producing anti-peptide antibodies in guinea pigs by hyperimmunization. The production of anti-peptide antibodies by hyperimmunization was verified by ELISA with a peptide which had not been coupled. All antisera were tested with respect to fluorescence against the cell lines NIH3T3 and NIH3T3/HPV 16. Several sera exhibited immunofluorescence. The antiserum against E6:1 (SEQ ID NO:158) was that serum which gave the most substantial immunofluorescence in the HPV positive cell while no fluorescence was obtained in the HPV negative cell (not shown).

All peptides were tested in ELISA with respect to reactivity with IgA, IgG or IgM antibodies in human sera. The HPV types 1, 5 and 8 infect the skin, HPV 1 gives common benign warts while HPV 5 and 8 are associated with malignant squamous cell carcinomas in the skin, and since it is well known that warts are very frequent with children the peptides for these three types were tested with a panel of 30 sera. The first ten sera are from children (2–8 years old), the following from patients with cervix cancer, where the HPV type of the tumour has not been determined, and the last ten sera are from patients with CIN where likewise the HPV type has not been determined. The results are given as the obtained optical densities at 415 nm multiplied with 1000. Values below 100 are not considered as positive but are included for the sake of completeness.

Peptide Ile Gly Ser Ala Arg Met Leu Val Lys Phe Ile Asp Glu Ala Gln Arg Glu Lys Cys (SEQ ID NO:1), HPV 1, protein E2.
IgA: 0, 541, 918, 186, 52, 0, 48, 0, 166, 37, 5, 0, 0, 0, 0, 3, 0, 36, 51, 0, 0, 0, 0, 11, 27, 48, 17, 113, 0, 0.
IgG: 185, 106, 117, 122, 183, 45, 276, 167, 94, 94, 204, 44, 80, 37, 72, 85, 176, 44, 49, 32, 85, 180, 55, 25, 51, 48, 73, 347, 40, 0.
IgM: 102, 88, 206, 70, 87, 49, 37, 1335, 936, 151, 146, 64, 0, 39, 0, 0, 1, 0, 33, 0, 58, 33, 55, 18, 14, 46, 14, 204, 13, 28.

Peptide Tyr Asp Asn Asn Pro Asp Asn Gln Thr Arg His Thr Ile Trp Asn His Val Tyr Tyr Gln (SEQ ID NO:2), HPV 1, E2.
IgA: 0, 28, 13, 0, 30, 3, 0, 0, 38, 9, 0, 24, 45, 0, 4, 33, 0, 84, 77, 0, 0, 16, 0, 31, 90, 114, 98, 67, 52, 0.
IgG: 150, 189, 165, 144, 249, 57, 304, 206, 109, 74, 305, 98, 176, 143, 227, 172, 386, 141, 86, 107, 182, 379, 116, 92, 125, 134, 164, 271, 138, 74.
IgM: 31, 17, 9, 105, 13, 16, 6, 311, 601, 139, 56, 93, 57, 8, 54, 38, 17, 14, 42, 24, 42, 26, 14, 23, 10, 11, 32, 17, 0, 0.

Peptide Leu Gly Ser Ser Leu Ala Ala Lys Cys Pro Glu Gln Ala Pro Pro Glu Pro Gln Thr Asp Pro Tyr (SEQ ID NO:4), HPV 1, L1.
IgA: 78, 93, 209, 38, 89, 40, 249, 56, 79, 92, 13, 200, 49, 35, 15, 50, 33, 100, 115, 0, 37, 678, 152, 53, 92, 396, 202, 64, 86, 0.
IgG: 219, 330, 209, 169, 217, 87, 355, 339, 169, 211, 211, 163, 218, 183, 316, 179, 367, 177, 131, 166, 165, 387, 98, 88, 102, 207, 162, 174, 68, 38.
IgM: 272, 56, 164, 326, 93, 167, 33, 686, 458, 415, 0, 109, 11, 13, 110, 0, 26, 84, 51, 75, 36, 27, 84, 64, 16, 54, 54, 7, 11, 148.

Peptide Asp Ile Pro Leu Val Glu Leu Asn Leu Gly Leu Glu Thr Asp Thr Ser Ser Val Val Gln (SEQ ID NO:5), HPV 1, L2.
IgA: 55, 0, 22, 0, 26, 48, 129, 0, 0, 0, 8, 0, 0, 0, 2, 50, 29, 0, 51, 0, 79, 68, 237, 13, 24, 81, 67, 23, 27, 0.
IgG: 223, 433, 276, 220, 264, 131, 347, 245, 128, 138, 315, 85, 184, 247, 247, 200, 479, 146, 83, 127, 370, 641, 259, 93, 104, 178, 95, 229, 109, 61.
IgM: 11, 0, 0, 50, 0, 0, 0, 95, 61, 0, 0, 0, 8, 0, 0, 0, 0, 0, 0, 26, 0, 0, 0, 0, 0, 0, 0, 0, 0, 0.

Peptide Leu Gly Arg Pro Arg Met Leu Ile Ser Phe Ser Ser Tyr Thr Gln Arg Arg Asp Cys (SEQ ID NO:6), HPV 5, E2.
IgA: 0, 0, 0, 0, 9, 0, 0, 0, 0, 0, 0, 0, 0, 0, 31, 0, 0, 0, 68, 0, 0, 0, 0, 0, 0, 0, 0, 0, 0, 0.
IgG: 108, 84, 129, 72, 62, 31, 316, 147, 70, 74, 130, 44, 82, 47, 69, 72, 125, 69, 78, 48, 40, 141, 33, 32, 50, 43, 62, 107, 66, 3.
IgM: 0, 0, 28, 0, 0, 0, 32, 0, 0, 0, 23, 48, 5, 3, 0, 11, 12, 1, 48, 0, 46, 49, 6, 8, 39, 11, 27, 24, 0, 6.

Peptide Leu Gly Arg Ser Arg Met Leu Ile Leu Phe Thr Ser Ala Gly Gln Arg Lys Asp Cys (SEQ ID NO:11), HPV 8, E2.
IgA: 0, 0, 195, 0, 48, 134, 427, 0, 0, 70, 503, 152, 1117, 401, 14, 843, 456, 577, 1581, 181, 93, 1396, 0, 15, 47, 213, 365, 415, 4, 0.

IgG: 115, 138, 259, 71, 80, 22, 192, 98, 87, 45, 623, 60, 194, 175, 259, 157, 404, 134, 125, 132, 165, 869, 40, 20, 35, 28, 57, 484, 21, 0.

IgM: 88, 72, 75, 0, 103, 48, 47, 0, 0, 0, 125, 94, 9, 89, 64, 53, 49, 0, 23, 36, 125, 54, 21, 57, 66, 35, 34, 12, 0, 12.

It is notable that the sera number 8 and 9 are considerably IgM positive with 3 out of 4 HPV 1 peptides and that the peptide from HPV 8 was considerably IgA positive for patients with cervix cancer but not for children.

HPV 6 and HPV 11 are two closely related viruses which cause pointed genital warts (condyloma) and rarely becomes malignant. In some rare cases, however, HPV6 and 11 can also be associated with CIN and cervix cancer. The test panel for HPV 6 consisted of 2 sera from patients with condyloma and known HPV 6 infection, 8 sera from patients with condyloma, 4 sera from patients with cervix cancer, 6 sera from patients with condyloma, 5 sera from patients with CIN and finally further 5 sera from patients with condyloma. The test panel for HPV 11 consisted of one serum from a patient with condyloma and HPV 11, 9 sera from patients with condyloma, 4 sera from patients with cervix cancer, 6 sera from patients with condyloma, 5 sera from patients with CIN, 4 sera from patients with condyloma and finally one serum from a patient with cervix cancer.

Peptide Phe Asp Gly Cys Ala Asn Asn Thr Met Asp Tyr Val Val Trp Thr Asp Val Tyr Val Gln (SEQ ID NO:7), HPV 6, E2.

IgA: 318, 0, 340, 607, 422, 242, 352, 421, 193, 112, 160, 340, 198, 171, 259, 66, 129, 101, 296, 229, 140, 206, 569, 253, 292, 119, 150, 92, 72, 236.

IgG: 207, 229, 517, 638, 259, 430, 224, 407, 357, 257, 482, 120, 356, 333, 404, 143, 11, 276, 172, 123, 382, 674, 141, 130, 186, 304, 145, 276, 164, 241.

IgM: 0, 0, 6, 54, 4, 1, 8, 0, 25, 0, 17, 14, 22, 5, 13, 0, 0, 5, 3, 26, 50, 62, 2, 80, 23, 2, 0, 17, 0, 20.

Peptide Arg Leu Gly Asn Glu His Glu Glu Ser Asn Ser Pro Leu Ala Thr Pro Cys Val Trp Pro (SEQ ID NO:8), HPV 6, E4.

IgA: 33, 0, 61, 690, 63, 29, 99, 152, 132, 32, 0, 0, 0, 2, 80, 35, 37, 93, 56, 43, 0, 0, 0, 0, 52, 225, 48, 396, 46, 42.

IgG: 0, 0, 0, 0, 0, 0, 363, 0, 11, 0, 0, 16, 0, 0, 0, 0, 0, 7, 0, 0, 0,3, 7, 0, 0, 28, 0, 0, 0, 0.

IgM: 0, 0, 0, 131, 0, 0, 0, 0, 0, 18, 41, 0, 45, 49, 87, 57, 10, 0, 9, 42, 89, 135, 49, 0, 49, 0, 20, 0, 59, 126, 27.

Peptide Pro Leu Asp Thr Phe Val Val Ser Ser Ser Asp Ser Gly Pro Thr Ser Ser Thr Pro Val (SEQ ID NO:10), HPV 6, L2.

IgA: 17, 1699, 10, 770, 14, 867, 20, 0, 255, 5, 511, 2682, 72, 4, 286, 108, 321, 285, 66, 2750, 159, 2604, 0, 46, 0, 2834, 48, 24, 88, 122.

IgG: 290, 2944, 2438, 955, 222, 2972, 436, 369, 440, 165, 528, 2651, 1301, 323, 953, 690, 93, 869, 157, 2961, 920, 2898, 351, 241, 197, 2952, 254, 552, 1550, 317.

IgM: 0, 0, 0, 122, 0, 0, 0, 0, 95, 0, 7, 0, 0, 0, 44, 8, 0, 0, 2, 0, 25, 0, 0, 0, 0, 0, 34, 0, 0, 0.

Peptide Phe Asp Gly Cys Glu Asp Asn Val Met Glu Tyr Val Val Trp Thr His Ile Tyr Leu Gln (SEQ ID NO:13), HPV 11, E2.

IgA: 178, 173, 474, 381, 229, 270, 322, 236, 122, 227, 52, 252, 170, 89, 75, 105, 181, 239, 191, 145, 190, 134, 440, 176, 151, 134, 92, 113, 169, 0.

IgG: 140, 613, 634, 346, 314, 254, 351, 414, 207, 519, 401, 153, 383, 374, 148, 44, 368, 278, 258, 291, 387, 633, 250, 125, 177, 215, 284, 241, 251, 311.

IgM: 0, 0, 246, 0, 0, 0, 0, 7, 0, 0, 1, 17, 8, 0, 0, 0, 0, 19, 0, 0, 13, 22, 0, 0, 0, 0, 0, 0, 0, 54.

Peptide Arg Arg Arg Leu Gly Ser Glu His Val Asp Arg Pro Leu Thr Thr Pro Cys Val Trp Pro (SEQ ID NO:14), HPV 11, E4.

IgA: 0, 26, 0, 0, 0, 0, 232, 22, 0, 31, 0, 0, 0, 0, 0, 0, 0, 64, 0, 41, 0, 0, 0, 5, 0, 0, 11, 0, 0, 67.

IgG: 0, 0, 0, 0, 0, 0, 0, 0, 0, 0, 0, 0, 0, 0, 0, 0, 0, 0, 0, 0, 0, 0, 0, 0, 0, 0, 0, 0, 0.

IgM: 10, 0, 17, 0, 0, 4, 191, 0, 0, 88, 13, 45, 0, 0, 4, 0, 0, 6, 0, 0, 40, 32, 0, 0, 3, 0, 83, 0, 0, 0.

Peptide Gln Ser Gln Ala Ile Thr Cys Gln Lys Pro Thr Pro Glu Lys Glu Lys Gln Asp Pro Tyr Lys (SEQ ID NO:16), HPV 11, L1.

IgA: 168, 48, 143, 137, 396, 123, 282, 229, 79, 511, 61, 329, 289, 554, 247, 62, 68, 235, 69, 76, 0, 625, 0, 786, 97, 0, 49, 129, 240, 0.

IgG: 46, 21, 122, 71, 148, 78, 46, 127, 47, 149, 150, 60, 386, 115, 78, 8, 154, 141, 100, 237, 200, 447, 115, 113, 126, 151, 204, 215, 219, 285.

IgM: 92, 0, 139, 21, 0, 0, 0, 319, 5, 248, 134, 759, 70, 46, 11, 0, 107, 285, 141, 591, 129, 172, 254, 27, 47, 3, 205, 375, 124, 262.

Peptide Pro Leu Asp Thr Phe Val Val Ser Ser Ser Asp Ser Gly Pro Thr Ser Ser Thr Pro Leu (SEQ ID NO:17), HPV 11, L2.

IgA: 0, 0, 83, 0, 132, 0, 0, 41, 0, 0, 0, 438, 9, 0, 51, 29, 144, 54, 300, 2621, 0, 1738, 0, 31, 0, 21, 17, 0, 36, 0.

IgG: 143, 2288, 338, 127, 431, 245, 218, 285, 91, 0, 428, 2712, 541, 217, 206, 34, 495, 178, 1167, 128, 155, 881, 201, 135, 126, 187, 283, 159, 197, 201.

IgM: 0, 0, 124, 0, 0, 0, 0, 0, 0, 0, 0, 0, 0, 26, 0, 0, 0, 1, 0, 0, 18, 0, 0, 0, 0, 76, 0, 0, 0, 56.

HPV 16 is that HPV type which is most commonly found with cervix cancer and CIN. The test panel for HPV 16 consisted of 10 sera from patients with cervix cancer and known HPV 16 infection, 10 sera from patients with cervix cancer and finally 10 sera from patients with CIN.

Peptide His Gly Asp Thr Pro Thr Leu His Glu Tyr Met Leu Asp Leu Gln Pro Glu Thr Thr Asp Leu Tyr Cys Tyr Glu Gln Leu Asn Asp Ser (SEQ ID NO:51), HPV 16, E7.

IgA: 183, 0, 0, 0, 3, 4, 80, 30, 0, 16, 18, 20, 0, 0, 0, 0, 0, 0, 34, 0, 74, 0, 188, 0, 0, 0, 12, 0, 0, 0.

IgG: 1283, 361, 0, 0, 0, 0, 93, 0, 0, 0, 18, 0, 8, 8, 0, 7, 0, 0, 0, 0, 0, 8, 2, 0, 0, 0, 0, 0, 0, 0.

IgM: 0, 25, 47, 13, 37, 40, 107, 44, 17, 38, 19, 39, 35, 30, 0, 24, 33, 11, 137, 17, 38, 43, 0, 5, 33, 10, 46, 15, 0, 14.

Peptide Gln Ala Glu Pro Asp Arg Ala His Tyr Asn Ile Val Thr Phe Cys Cys Lys Cys Asp Ser Thr Leu Arg Leu Cys Val Gln Ser Thr His (SEQ ID NO:52), HPV 16, E7.

IgA: 0, 43, 79, 142, 91, 162, 365, 78, 133, 266, 278, 491, 270, 184, 13, 288, 220, 106, 504, 0, 0, 215, 946, 536, 102, 149, 761, 243, 472, 0.

IgG: 20, 0, 6, 0, 7, 24, 36, 0, 8 ,7, 108, 25, 58, 39, 53, 34, 70, 30, 25, 0, 18, 84, 4, 19, 32, 13, 129, 89, 7, 0.

IgM: 155, 163, 148, 298, 254, 698, 261, 81, 289, 144, 1831, 600, 269, 374, 364, 265, 137, 497, 308, 141, 166, 161, 354, 395, 256, 143, 612, 236, 1037, 163.

Peptide Cys Cys Lys Cys Asp Ser Thr Leu Arg Leu Cys Val Gln Ser Thr His Val Asp Ile Arg Thr Leu Glu Asp Leu Leu Met Gly Thr Leu (SEQ ID NO:53), HPV 16, E7.

IgA: 351, 188, 277, 99, 334, 427, 954, 375, 344, 833, 459, 634, 707, 615, 17, 834, 518, 967, 1651, 566, 255, 607, 1150, 485, 519, 426, 380, 335, 415, 107.

IgG: 33, 103, 0, 0, 17, 23, 20, 0, 6, 10, 190, 20, 108, 69, 174, 40, 112, 10, 0, 0, 55, 91, 0, 14, 20, 0, 0, 23, 0, 0.

IgM: 0, 26, 22, 33, 33, 341, 23, 2, 3, 45, 83, 20, 15, 188, 100, 26, 24, 0, 325, 13, 61, 48, 0, 52, 247, 3, 54, 282, 4, 0.

Peptide Val Gln Ser Thr His Val Asp Ile Arg Thr Leu Glu Asp Leu Leu Met Gly Thr Leu Gly Ile Val Cys Pro Ile Cys Ser Gln Lys Pro (SEQ ID NO:54), HPV 16, E7.

IgA: 14, 66, 68, 19, 69, 75, 159, 77, 41, 117, 63, 133, 54, 0, 17, 104, 17, 43, 112, 0, 0, 91, 1, 50, 89, 72, 35, 30, 78, 0.

IgG: 0, 0, 0, 0, 0, 0, 0, 0, 0, 0, 0, 0, 0, 0, 0, 0, 0, 0, 0, 0, 0, 0, 0, 0, 0, 0, 0, 0, 0.

IgM: 0, 0, 0, 0, 0, 0, 0, 0, 0, 0, 118, 2, 0, 0, 0, 0, 0, 0, 4, 0, 7, 0, 0, 0, 0, 0, 0, 0, 0, 0.

New peptide from HPV 16, L1

The nucleotide sequence of the L1 open reading frame of HPV 16 was recently determined a second time (Parton, Nucleic Acids Research, 18, 3631 (1990)). It was found that the original nucleotide sequence contained two errors that changed the deduced amino acid sequence at two positions close to each other in the carboxyterminal part of L1. To investigate whether these corrections were important, a peptide covering the region of these 2 errors and a peptide from the same region but with the corrected sequence were synthesized. They were tested in IgA ELISA with a panel of 30 sera from patients with HPV-carrying CIN or cervical cancer with the following results given as absorbances:

Peptide VTQAIACQKHTPPAPKEDDPL (SEQ ID NO:174) (old, incorrect sequence):

0.110, 1.854, 0, 0, 0, 0.571, 0.195, 0.123, 0, 0, 0, 0, 0, 0, 0, 0, 0, 0, 0.343, 0, 0, 0, 0, 0, 0, 0, 0, 0.383.

Peptide Val Thr Ser Gln Ala Ile Ala Cys Gln Lys His Thr Pro Pro Ala Pro Lys Glu Asp Pro Leu (SEQ ID NO:55) (corrected sequence):

0.124, 2.903, 0, 0, 0, 1.012, 0.289, 0.228, 0, 0, 0, 0.374, 0, 0, 0,0, 0, 0.125, 0, 0.610, 0, 0, 0.162, 0, 0, 0, 0.197, 0, 0, 0.632.

Results with an IgG ELISA gave a Similar Tendency (not shown).

The old peptide is partially overlapped by the peptides number 30:GGTLEDTYRFVTQAIACQKH (SEQ ID NO:175) and number 31:ACQKHTPPAPKEDDPLKKYT (SEQ ID NO:176), which were described in our previous patent application. While peptide 30 (SEQ ID NO:175) was not significantly immunoreactive, peptide 31 (SEQ ID NO:176) was reactive. Comparison of the immunoreactivity of peptide 31 (SEQ ID NO:176) with peptide VTQAIACQKHTPPAPKEDDPL (SEQ ID NO:174) showed that peptide VTQAIACQKHTPPAPKEDDPL (SEQ ID NO:174) represented a slight improvement over peptide 31 (SEQ ID NO:176) (not shown).

The peptide E2:9 in FIGS. 4, 5 and 6 had the sequence FDGDICNTMHYTNWTHIYIC (SEQ ID NO:136). In order to see if the immunoreactivity of this peptide could be improved, we synthesized two analogs of this peptide that removed 2 amino acids compared to the original peptide, either in the N-terminal (peptide E2:9(N): VQFDGDICNTMHYTNWTHIY) or in the C-terminal direction (peptide E2:9(C): GDICNTMHYTNWTHIYICEE). They were then tested in an IgA ELISA with a panel of 30 sera from patients with CIN (The number of IgA-positive sera in this panel was less than in the panel with cervical cancer sera which was used in FIGS. 4, 5 and 6).

Peptide E2:9 (SEQ ID NO:136):

0, 0, 0, 0.105, 0, 0, 0, 0, 0, 0, 0, 0, 0.199, 0, 0, 0, 0, 0, 0, 0.124, 0.102, 0.164, 0.126, 0, 0, 0, 0, 0, 0.

Peptide E2:9(C) (SEQ ID NO:178):

0.222, 0, 0.253, 0.136, 0, 0, 0.159, 0, 0, 0, 0, 0, 0.172, 0, 0, 0,0, 0, 0, 0.172, 0.210, 0.233, 0.161, 0, 0, 0, 0.134, 0.104, 0.155.

As can be seen, all the sera that were positive for the original peptide were also positive for the improved peptide. In all cases but one (serum number 14, 0.199 versus 0.172) the immunoreactivity was improved when peptide E2:9(C) (SEQ ID NO:178) was used. An IgG ELISA with the same sera and peptides showed that peptide E2:9(C) (SEQ ID NO:178) was an improvement also for IgG (not shown). The peptide analog E2:9 (N) (SEQ ID NO:177) gave similar results as did peptide E2:9 (SEQ ID NO:136) (not shown).

Use of peptides from L1 of HPV 16 to produce antipeptide sera that will detect all types of papillomaviruses.

In our previous patent application, peptides based on the deduced amino acid sequence of HPV 16 L1 were synthesized. The peptides were used in ELISA for detection of human antipeptide antibodies to these peptides. It was also proposed in the patent claims that these peptides could be used in the diagnosis of papillomavirus associated disease by the detection of antigen-antibody complexes in tissue. The claims also included peptides containing the same epitope and peptides containing substantial homology with the original peptide.

Group-specific detection does not necessarily mean that every single virus within the papillomavirus group should be detectable but the detection should be broadly reactive with genetically diverse papillomavirus types from several host species.

Thus, which ones of these HPV 16-derived peptides that were reactive with antibodies against bovine, canine and avian papillomaviruses was now tested to see which epitopes that were shared between these papillomaviruses with a very low degree of relatedness. As shown in FIG. 20, peptides 16 (SEQ ID NO:179), 30 (SEQ ID NO:181), 31 (SEQ ID NO:181) and 33 (SEQ ID NO:182) from WO 90/04790 represented the main group-specific epitopes.

The prospects of producing antibodies against bovine papillomavirus (BPV) were then examined by immunization of guinea pigs with peptides 16 (SEQ ID NO:179), 30 (SEQ ID NO:181), 31 (SEQ ID NO:181) and 33 (SEQ ID NO:182). For comparison, antisera against all the other peptides were also produced. However, as shown in FIG. 21, very low or no reactivity at all against BPV was found in ELISA.

Shortened versions of the original peptides 16 (SEQ ID NO:179), 30 (SEQ ID NO:181), 31 (SEQ ID NO:181) and 33 (SEQ ID NO:182) were then synthesized and used for immunization. As shown in FIG. 21, the antipeptide antisera were now reactive with BPV. The most successful peptide was peptide 16a, with the sequence Val His Thr Gly Phe Gly Ala Met Asp Phe Thr Thr Leu Gln Ala Gly Gly Cys (SEQ ID NO:56), which gave an anti-BPV titer of 12.500 which should be compared to the anti-BPV titer of the antiserum against the original peptide 16 which was less than 100 (i e not significant).

For peptide 30b Gly Gly Thr Leu Glu Asp Thr Tyr Arg Phe Gly Gly Cys (SEQ ID NO:57), an anti-BPV reaction was also obtained, which was not detectable for the original peptide.

For peptide 33a (SEQ ID NO:183) (SADLDQFPLGRKFLLGGC), the reactivity towards BPV was improved but the antiserum against the original peptide 33 (SEQ ID NO:182) also produced some anti-BPV antibodies. The antiserum to peptide 16a (SEQ ID NO:184) was then analyzed for its reactivity in Lmmunohistocytochemical staining of slides containing sections of human and bovine skin warts and was found to stain both types of viruses in this application in accordance with the ELISA data (not shown).

HPV 18 is a common virus associated with CIN and cervix cancer, especially adenocarcinoma. The test panel for HPV 18 consisted of 7 sera from patients with cervix cancer and known HPV 18 infection, 2 sera from patients with CIN and known HPV 18 infection, 11 sera from patients with cervix cancer and finally 10 sera from patients with CIN.

Peptide Phe Asp Gly Asn Lys Asp Asn Cys Met Thr Tyr Val Ala Trp Asp Ser Val Tyr Tyr Met (SEQ ID NO:58), HPV 18, E2.
IgA: 27, 3, 0, 22, 15, 89, 74, 75, 7, 0, 0, 60, 60, 0, 0, 19, 19, 24, 83, 0, 84, 0, 393, 79, 98, 146, 0, 36, 0.
IgG: 282, 371, 222, 146, 220, 315, 442, 339, 169, 0, 581, 176, 406, 412, 498, 300, 696, 306, 192, 194, 438, 628, 279, 157, 329, 280, 233, 357, 162, 75.
IgM: 42, 55, 0, 28, 39, 30, 28, 0, 0, 0, 85, 49, 103, 25, 48, 28, 31, 18, 41, 31, 76, 76, 50, 30, 46, 22, 66, 21, 29, 0.
Peptide Ser Leu Leu Asn Ser Tyr Ser Thr Pro Pro His Arg Ile Pro Ala Pro Cys Pro Trp Ala (SEQ ID NO:59), HPV 18, E4.
IgA: 34, 0, 0, 0, 61, 46, 62, 0, 0, 0, 0, 17, 35, 0, 5, 0, 0, 0, 35, 0, 0, 0, 293, 0, 17, 0, 14, 32, 0, 0.
IgG: 0, 0, 0, 3, 0, 0, 0, 0, 0, 0, 0, 33, 0, 0, 0, 0, 0, 0, 0, 0, 0, 0, 9, 0, 0, 0.
IgM: 24, 0, 0, 0, 10, 9, 0, 0, 1, 0, 0, 17, 36, 2, 4, 0, 20, 12, 30, 0, 33, 78, 0, 0, 62, 0, 0, 31, 0, 0.
Peptide His Gly Pro Lys Ala Thr Leu Gln Asp Ile Val Leu His Leu Glu Pro Gln Asn Glu Ile Pro Val Asp Leu Leu Cys His Glu Gln Leu (SEQ ID NO:61), HPV 18, E7.
IgA: 171, 48, 0, 21, 77, 108, 294, 119, 24, 0, 41, 271, 80, 40, 0, 121, 181, 37, 252, 48, 148, 145, 517, 156, 150, 212, 236, 17, 155, 0.
IgG: 0, 17, 0, 21, 4, 4t 4, 0, 0, 0, 23, 9, 14, 0, 0, 3, 8, 0, 0, 0, 0, 38, 0, 0, 0, 0, 0, 0, 0, 0.
IgM: 17, 38, 0, 22, 22, 31, 10, 0, 1, 0, 41, 65, 12, 8, 19, 19, 0, 31, 0, 65, 38, 0, 4, 8, 18, 23, 0, 0, 0.
Peptide Pro Gln Asn Glu Ile Pro Val Asp Leu Leu Cys His Glu Gln Leu Ser Asp Ser Glu Glu Glu Asn Asp Glu Ile Asp Gly Val Asn His (SEQ ID NO:62), HPV 18, E7.
IgA: 0, 0, 0, 20, 3, 0, 24, 205, 11, 0, 0, 58, 0, 0, 0, 15, 0, 0, 85, 0, 5, 0, 16, 0, 0, 35, 115, 5, 19, 0.
IgG: 0, 0, 0, 0, 0, 0, 0, 0, 0, 0, 0, 6, 3, 0, 0, 0, 0, 0, 0, 0, 0, 10, 5, 0, 18, 0, 10, 0, 0, 0.
IgM: 20, 16, 0, 3, 14, 2, 0, 0, 31, 0, 25, 60, 0, 4, 0, 13, 9, 1, 33, 0, 146, 54, 0, 4, 8, 14, 17, 70, 4, 2.
Peptide Ser Asp Ser Glu Glu Glu Asn Asp Glu Ile Asp Gly Val Asn His Gln His Leu Pro Ala Arg Arg Ala Glu Pro Gln Arg His Thr Met (SEQ ID NO:63), HPV 18, E7.
IgA: 0, 0, 0, 2, 37, 67, 1410, 0, 60, 0, 0, 41, 0, 0, 18, 28, 0, 0, 55, 0, 0, 0, 0, 0, 73, 100, 80, 33, 22, 0.
IgG: 0, 0, 0, 30, 0, 0, 0, 0, 0, 0, 0, 4, 0, 0, 0, 0, 0, 0, 0, 0, 0, 0, 0, 0, 2, 2, 3, 0, 0.
IgM: 4, 0, 0, 0, 2, 0, 0, 0, 19, 0, 0, 54, 0, 0, 0, 0, 0, 0, 51, 0, 29, 26, 0, 0, 15, 1, 6, 50, 0, 35.
Peptide Gln His Leu Pro Ala Arg Arg Ala Glu Pro Gln Arg His Thr Met Leu Cys Met Cys Cys Lys Cys Glu Ala Arg Ile Glu Leu Val Val (SEQ ID NO:64), HPV 18, E7.
IgA: 331, 236, 83, 7, 193, 202, 141, 0, 30, 266, 144, 627, 301, 155, 14, 440, 213, 94, 662, 0, 0, 971, 0, 0, 4, 520, 243, 506, 102, 0.
IgG: 0, 34, 0, 0, 13, 6, 0, 0, 0, 0, 14, 63, 31, 13, 8, 19, 0, 7, 7, 0, 1, 122, 0, 0, 0, 156, 16, 26, 39, 0.
IgM: 23, 143, 59, 162, 131, 143, 29, 121, 96, 136, 82, 80, 61, 130, 104, 83, 63, 99, 124, 58, 137, 22, 22, 46, 129, 146, 131, 27, 44, 121.
Peptide Leu Cys Met Cys Cys Lys Cys Glu Ala Arg Ile Glu Leu Val Val Glu Ser Ser Ala Asp Asp Leu Arg Ala Phe Gln Gln Leu Phe Leu (SEQ ID NO:65), HPV 18, E7.
IgA: 374, 28, 0, 44, 137, 205, 484, 27, 28, 71, 114, 1835, 23, 87, 10, 155, 103, 435, 360, 492, 145, 74, 339, 540, 243, 453, 225, 0, 219, 0.
IgG: 565, 606, 438, 266, 414, 546, 758, 432, 275, 468, 823, 195, 492, 687, 710, 466, 929, 346, 331, 185, 663, 952, 464, 335, 381, 399, 260, 386, 211, 100.
IgM: 26, 39, 0, 32, 40, 109, 119, 15, 66, 29, 77, 28, 0, 137, 0, 31, 20, 156, 116, 50, 135, 45, 30, 60, 68, 49, 50, 30, 92, 10.
Peptide Glu Ser Ser Ala Asp Asp Leu Arg Ala Phe Gln Gln Leu Phe Leu Asn Thr Leu Ser Phe Val Cys Pro Trp Cys Ala Ser Gln Gln (SEQ ID NO:66), HPV 18, E7.
IgA: 91, 12, 0, 7, 104, 243, 140, 0, 5, 18, 0, 87, 0, 0, 0, 60, 0, 0, 151, 0, 0, 79, 0, 15, 72, 155, 121, 0, 102, 0.
IgG: 331, 376, 287, 226, 271, 304, 438, 217, 147, 216, 392, 186, 354, 280, 366, 319, 551, 229, 218, 135, 325, 520, 254, 181, 190, 129, 140, 239, 92, 39.
IgM: 55, 103, 0, 81, 152, 417, 98, 36, 52, 7, 32, 205, 36, 43, 0, 27, 53, 24, 52, 22, 151, 125, 180, 76, 139, 156, 142, 36, 352, 153.
Peptide Gln Ser Val Ala Ile Thr Cys Gln Lys Asp Ala Ala Pro Ala Glu Asn Lys Asp Pro Tyr Asp (SEQ ID NO:67), HPV 18, L1.
IgA: 223, 0, 0, 0, 0, 45, 0, 53, 0, 0, 0, 0, 10, 0, 0, 32, 0, 0, 4, 0, 0, 0, 1, 0, 9, 0, 28, 66, 24, 0.
IgG: 226, 233, 192, 90, 126, 597, 286, 248, 138, 0, 376, 46, 135, 83, 149, 118, 320, 108, 320, 108, 66, 117, 272, 435, 108, 30, 99, 118, 94, 405, 99, 25.
IgM: 50, 9, 99, 58, 12, 0, 0, 20, 65, 0, 32, 57, 24, 0, 0, 0, 0, 0, 13, 0, 25, 48, 70, 12, 95, 0, 0, 42, 115, 29.
Peptide Pro Leu Gln Thr Phe Ala Ser Ser Gly Thr Gly Glu Glu Pro Ile Ser Ser Thr Pro Leu (SEQ ID NO:68), HPV 18, L2.
IgA: 270, 124, 0, 25, 31, 176, 34, 203, 109, 11, 143, 933, 43, 13, 0, 89, 17, 0, 26, 14, 169, 2604, 33, 41, 30, 1556, 689, 453, 62, 0.
IgG: 1449, 350, 336, 143, 155, 280, 382, 410, 312, 166, 470, 2751, 990, 213, 519, 1468, 457, 255, 94, 166, 537, 2181, 332, 223, 133, 918, 1513, 420, 189, 146.
IgM: 0, 63, 0, 0, 4, 200, 0, 30, 27, 0, 41, 8, 0, 205, 61, 0, 0, 0, 0, 0, 127, 0, 0, 0, 7, 12, 55, 46, 47, 1.

HPV 31 is also a common virus in connection with CIN and is sometimes seen in connection with cervix cancer. The test panel for HPV 31 consisted of 10 sera from patients with CIN and known HPV 31 infection, 10 sera from patients with cervix cancer and 10 sera from patients with CIN.

Peptide Phe Asp Gly Asp Val His Asn Thr Met His Tyr Thr Asn Trp Lys Phe Ile Tyr Leu Cys (SEQ ID NO:69), HPV 31, E2.
IgA: 24, 0, 28, 0, 31, 16, 9, 31, 0, 106, 33, 183, 117, 210, 10, 158, 88, 101, 303, 0, 0, 82, 64, 127, 164, 197, 156, 49, 231, 0.
IgG: 24, 0, 21, 0, 19, 16, 8, 37, 3, 0, 13, 14, 33, 1, 35, 40, 72, 34, 14, 9, 28, 86, 0, 4, 0, 16, 55, 55, 26, 0.
IgM: 0, 0, 0, 0, 0, 0, 0, 24, 0, 39, 23, 63, 39, 1, 6, 35, 44, 47, 93, 35, 52, 56, 35, 45, 52, 46, 35, 60, 74, 28.
Peptide His Lys Asn Ala Ile Val Thr Leu Thr Tyr Ile Ser Thr Ser Gln Arg Asp Asp Cys (SEQ ID NO:70), HPV 31, E2.
IgA: 120, 0, 88, 46, 133, 122, 15, 87, 0, 270, 281, 336, 390, 213, 55, 486, 199, 319, 1011, 70, 6, 306, 335, 210, 1868, 318, 379, 272, 213, 0.
IgG: 296, 220, 158, 99, 117, 201, 245, 255, 264, 159, 1056, 369, 494, 310, 722, 263, 697, 342, 309, 276, 338, 538, 140, 117, 194, 166, 240, 428, 238, 94.
IgM: 104, 67, 52, 26, 44, 59, 17, 52, 0, 113, 167, 133, 74, 76, 219, 59, 39, 70, 653, 114, 241, 145, 37, 221, 2227, 50, 69, 120, 137, 35.
Peptide Thr Ser Gln Ala Ile Thr Cys Gln Lys Thr Ala Pro Gln Lys Pro Lys Glu Asp Pro Phe Lys (SEQ ID NO:72), HPV 31, L1.
IgA: 0, 0, 10, 0, 0, 0, 10, 4, 0, 61, 6, 64, 48, 15, 0, 0, 0, 108, 0, 0, 29, 0, 22, 16, 84, 24, 222, 17, 0.
IgG: 2, 0, 8, 1, 18, 13, 15, 33, 0, 0, 0, 9, 0, 0, 0, 0, 0, 0, 0, 0, 0, 0, 0, 0, 0, 0, 0, 78, 0, 0.

IgM; 255, 65, 319, 524, 18, 35, 9, 87, 223, 140, 15, 398, 31, 294, 139, 0, 0, 0, 39, 0, 40, 129, 104, 0, 9, 17, 49, 239, 301, 184.

Peptide Pro Met Asp Thr Phe Ile Val Ser Thr Asn Asn Gln Asn Ile Thr Ser Ser Thr Pro Ile (SEQ ID NO:73), HPV 31, L2.

IgA: 206, 207, 729, 121, 625, 1343, 12, 250, 91, 755, 1144, 2682, 144, 107, 4, 317, 22, 117, 108, 39, 238, 2604, 0, 51, 96, 2800, 2406, 2831, 762, 0.

IgG: 64, 255, 144, 13, 326, 116, 741, 162, 77, 259, 43, 583, 214, 12, 298, 713, 0, 76, 10, 57, 103, 473, 12, 19, 1, 709, 393, 0, 557, 126.

IgM: 29, 96, 0, 153, 0, 0, 0, 17, 131, 74, 21, 0, 0, 95, 86, 0, 0, 0, 22, 7, 121, 0, 12, 5, 10, 29, 0, 0, 8, 0.

HPV 33 is a relatively new virus which has been found to be rather common both in connection with CIN and cervix cancer. The test panel for HPV 33 consisted of 4 sera from patients with cervix cancer and known HPV 33 infection, 5 sera from patients with CIN and known HPV 33 infection, 11 sera from patients with cervix cancer and finally 10 sera from patients with CIN.

Peptide Tyr Asp Asn Asp Lys Lys Asn Thr Met Asp Tyr Thr Asn Trp Gly Glu Ile Tyr Ile Ile (SEQ ID NO:74), HPV 33, E2.

IgA: 53, 0, 29, 204, 67, 65, 19, 83, 210, 47, 12, 170, 77, 551, 35, 140, 146, 71, 150, 103, 210, 87, 347, 143, 180, 222, 241, 110, 171, 0.

IgG: 165, 268, 2202, 237, 240, 415, 97, 211, 333, 147, 458, 191, 323, 384, 330, 250, 714, 185, 146, 142, 459, 541, 250, 110, 124, 242, 148, 335, 149, 65.

IgM: 4, 0, 0, 0, 0, 0, 0, 0, 2, 155, 7, 0, 0, 0, 0, 0, 0, 0, 0, 0, 0, 24, 0, 0, 0, 0, 0, 7, 0, 0.

Peptide Pro Gln Thr Pro Pro Ser Pro Leu Gln Ser Cys Ser Val Gln Thr Pro Pro Trp Thr Ile (SEQ ID NO:75), HPV 33, E4.

IgA: 92, 0, 28, 14, 0, 22, 7, 38, 127, 62, 73, 200, 74, 138, 44, 227, 49, 61, 283, 0, 41, 121, 69, 88, 145, 68, 37, 81, 84, 0.

IgG: 6, 5, 0, 1, 19, 0, 0, 0, 0, 0, 0, 27, 0, 15, 0, 0, 0, 20, 0, 0, 0, 0, 0, 0, 0, 0, 0, 0, 0, 0.

IgM: 355, 66, 163, 12, 73, 94, 32, 212, 55, 80, 136, 374, 71, 112, 57, 210, 40, 31, 650, 37, 627, 222, 45, 168, 50, 31, 37, 51, 88, 118.

Peptide Thr Ser Gln Ala Ile Thr Cys Gln Lys Thr Val Pro Pro Lys Glu Lys Glu Asp Pro Leu Gly (SEQ ID NO:77), HPV 33, L1.

IgA: 48, 0, 0, 0, 0, 0, 0, 0, 76, 0, 35, 0, 0, 454, 0, 0, 0, 0, 61, 0, 0, 30, 0, 24, 0, 0, 32, 14, 0, 0.

IgG: 139, 128, 936, 57, 82, 82, 220, 39, 86, 127, 264, 48, 87, 34, 111, 89, 261, 50, 69, 29, 184, 316, 93, 0, 28, 21, 34, 237, 35, 0.

IgM: 5, 0, 0, 0, 55, 78, 31, 112, 209, 122, 105, 304, 137, 14, 37, 0, 1, 9, 4, 0, 99, 150, 149, 0, 0, 11, 56, 123, 190, 108.

Peptide Pro Met Asp Thr Phe Val Val Ser Thr Asp Ser Ser Asn Val Thr Ser Ser Thr Pro Ile (SEQ ID NO:78), HPV 33, L2.

IgA: 0, 0, 0, 0, 2734, 29, 2840, 98, 266, 17, 1066, 1921, 0, 6, 0, 0, 230, 0, 0, 0, 0, 182, 2604, 0, 0, 0, 2800, 2362, 2238, 603, 0.

IgG: 740, 2531, 2626, 200, 2990, 1286, 486, 741, 1034, 248, 526, 2439, 1431, 332, 1533, 2967, 420, 727, 191, 480, 862, 2469, 375, 228, 132, 2977, 2368, 304, 2684, 790.

IgM: 43, 23, 127, 12, 52, 146, 0, 6, 184, 25, 77, 58, 53, 146, 202, 12, 19, 54, 27, 63, 172, 0, 54, 18, 52, 172, 19, 0, 134, 3.

E7 Peptides for HPV Types 1, 5, 6, 8, 11, 18, 31, 33 and 56

As described above, an HPV 16 peptide from the E7 open reading frame which had the sequence Cys Cys Lys Cys Asp Ser Thr Leu Arg Leu Cys Val Gln Ser Thr His Val Asp Ile Arg Thr Leu Glu Asp Leu Leu Met Gly Thr Leu (SEQ ID NO:53)

was studied. Analysis of the predicted amino acid sequences revealed that all papillomaviruses have a motif of 30 amino acids in the E7 open reading frame that can be represented by (SEQ ID NO:185) CxxCxxxxxxxxxxxxxxxxxxxxLL'xxxL', where L' usually is Leucine, but in a few cases was substituted for the other hydrophobic amino acids Valine or Phenylalanine.

The peptides described by this formula were synthesized for HPV 1, 5, 8, 6, 11, 18, 31, 33 and 56 and tested in IgA and IgG ELISAs with a panel of 30 sera from patients with CIN.

Peptide Cys Cys Gly Cys Asp Ser Asn Val Arg Leu Val Val Gln Cys Thr Glu Thr Asp Ile Arg Glu Val Gln Gln Leu Leu Leu Gly Thr Leu (SEQ ID NO:9) (HPV 6, E7), IgA: 0.162, 0, 0.182, 0.228, 0, 0, 0, 0, 0, 0, 0, 0, 0.122, 0.185, 0, 0, 0, 0, 0, 0, 0.134, 0.197, 0.227, 0.100, 0, 0.104, 0, 0.117, 0, 0.121.

IgG: 0.240, 0.287, 0.130, 0, 0, 0.185, 0, 0, 0.224, 0, 0, 0.145, 0, 0.130, 0, 0, 0, 0, 0, 0, 0.401, 0, 0, 0.161, 0, 0, 0, 0, 0, 0.126.

Peptide Cys Ala Tyr Cys Glu Lys Leu Val Arg Leu Thr Val Leu Ala Asp His Ser Ala Ile Arg Gln Leu Glu Glu Leu Leu Leu Arg Ser Leu (SEQ ID NO:3) (HPV 1, E7), IgA: 0.128, 0, 0.142, 0.125, 0, 0, 0, 0, 0, 0, 0, 0.115, 0.230, 0, 0, 0, 0, 0, 0.120, 0.121, 0.162, 0.115, 0, 0, 0, 0.121, 0, 0.

IgG: 0.229, 0.176, 0.108, 0, 0, 0, 0, 0, 0.123, 0, 0, 0, 0, 0.121, 0, 0, 0, 0, 0, 0, 0.166, 0, 0, 0, 0.130, 0, 0, 0, 0, 0.105

Peptide Cys His Thr Cys Asn Thr Thr Val Arg Leu Cys Val Asn Ser Thr Ala Ser Asp Leu Arg Thr Ile Gln Gln Leu Leu Met Gly Thr Val (SEQ ID NO:76) (HPV 33, E7), IgA: 0, 0.178, 0, 0, 0, 0, 0.115, 0.103, 0.115, 0, 0, 0, 0.115, 0.339, 0, 0.148, 0.145, 0.105, 0.205, 0.350, 0.112, 0.130, 0.138, 0.196, 0, 0, 0, 0.117, 0, 0.132.

IgG: 0.148, 0.301, 0.114, 0, 0.134, 0.110, 0, 0.180, 0.161, 0, 0, 0.145, 0, 0.170, 0, 0, 0, 0.130, 0.143, 0.161, 0, 0, 0, 0.127, 0.112, 0, 0, 0, 0, 0.111.

Peptide Cys Cys Gly Cys Asp Ser Asn Val Arg Leu Val Val Glu Cys Thr Asp Gly Asp Ile Arg Gln Leu Gln Asp Leu Leu Leu Gly Thr Leu (SEQ ID NO:15) (HPV 11, E7), IgA: 0.253, 0, 0.286, 0.142, 0, 0, 0, 0, 0, 0, 0, 0, 0.230, 0, 0, 0, 0, 0, 0.199, 0.229, 0.226, 0.158, 0, 0, 0, 0.107, 0, 0.123.

IgG: 0.325, 0.464, 0.259, 0, 0, 0.293, 0, 0, 0.307, 0.133, 0, 0.219, 0, 0.178, 0, 0, 0, 0, 0, 0, 0.699, 0, 0, 0.261, 0, 0, 0, 0, 0, 0.210.

Peptide Cys Ser Cys Cys Gln Val Lys Leu Arg Leu Phe Val Asn Ala Thr Asp Ser Gly Ile Arg Thr Phe Gln Glu Leu Leu Phe Arg Asp Leu (SEQ ID NO:12) (HPV 8, E7), IgA: 0.103, 0, 0, 0.144, 0, 0, 0, 0, 0, 0, 0, 0, 0.214, 0, 0, 0, 0, 0, 0, 0.133, 0.144, 0.200, 0.140, 0, 0, 0, 0, 0, 0.

IgG: 0.119, 0.198, 0, 0, 0, 0, 0, 0, 0.112, 0, 0, 0.135, 0, 0.140, 0, 0, 0, 0, 0, 0, 0, 0, 0.108, 0, 0, 0, 0, 0, 0.

Peptide Cys Cys Lys Cys Glu Ala Arg Ile Glu Leu Val Val Glu Ser Ser Ala Asp Asp Leu Arg Ala Phe Gln Gln Leu Phe Leu Asn Thr Leu (SEQ ID NO:60) (HPV 18, E7), IgA: 0.143, 0, 0.292, 0.133, 0, 0.127, 0, 0, 0, 0, 0, 0, 0.221, 0, 0, 0, 0, 0, 0, 0.129, 0.206, 0.200, 0.141, 0, 0, 0.123, 0.135, 0, 175.

IgG: 0.239, 0.276, 0.200, 0, 0, 0.182, 0, 0, 0.199, 0, 0, 0.181, 0, 0, 0, 0, 0, 0, 0.476, 0.167, 0, 0.171, 0, 0, 0, 0, 0, 0.

Peptide CRNCEVKLRIFVHATEFGIRAFQQLLTGDL (SEQ ID NO:186) (HPV 5, E7),

IgA; 0, 0, 0, 0, 0, 0, 0, 0, 0, 0, 0, 0, 0, 0, 0, 0, 0, 0, 0, 0, 0, 0, 0.128, 0, 0, 0, 0, 0, 0.

IgG: All 30 were negative.

Peptide Cys Cys Glu Cys Lys Phe Val Val Gln Leu Asp Ile Gln Ser Thr Lys Glu Asp Leu Arg Val Val Gln Gln Leu Leu Met Gly Ala Leu (SEQ ID NO:79) (HPV 56, E7), IgA: 0.149, 0, 0.171, 0, 0, 0, 0, 0, 0, 0, 0, 0, 0, 0.117, 0.260, 0, 0, 0, 0.112, 0, 0, 0.132, 0.145, 0.135, 0.120, 0, 0, 0, 0.132, 0, 0.122.

IgG; 0.134, 0.224, 0, 0, 0, 0.110, 0, 0, 0.113, 0, 0, 0, 0, 0.105, 0, 0, 0, 0, 0, 0, 0.182, 0, 0, 0, 0, 0, 0, 0, 0.

Peptide Cys Cys Gln Cys Lys Ser Thr Leu Arg Leu Cys Val Gln Ser Thr Gln Val Asp Ile Arg Ile Leu Gln Glu Leu Leu Met Gly Ser Phe (SEQ ID NO:71) (HPV 31, E7), IgA: 1.344, 0.200, 0.855, 0.600, 0, 0.358, 0.282, 0, 0.158, 0, 0, 0, 0, 0.694, 0.122, 0, 0, 0, 0, 0.107, 0.902, 0.948, 1.762, 0.882, 0, 0, 0, 0, 0.121, 0.451.

IgG: 0.448, 0.775, 0.435, 0.123, 0, 0.530, 0.411, 0, 0.529, 0.405, 0, 0.825, 0, 0.538, 0.179, 0, 0, 0, 0, 0, 0.588, 0.198, 0, 0.635, 0, 0, 0, 0.422, 0.163, 0.474.

As shown by the results presented above, this site in the E7 protein is an important antigenic site (for both IgA and IgG) that was present for all HPV types tested except HPV 5.

Essential Amino Acids in the Major E4 Epitope.

The major E4 epitope, peptide E4:4 Ala Asp Pro Ala Ala Ala Thr Lys Tyr Pro Leu Leu Lys Leu Leu Gly Ser Thr Trp Pro Thr Thr Pro Pro Arg Pro Ile Pro Lys Pro (SEQ ID NO:41); Trp Pro Thr Thr Pro Pro Arg Pro Ile Pro Lys Pro Ser Pro Trp Ala Pro Lys Lys His Arg Arg Leu Ser Ser Asp Gln Asp Gln Ser (SEQ ID NO 42); KHRRLSSDQDQSQTPE-TPATPLSCCTETQW (SEQ ID NO:190); QSQTPETPAT-PLSCCTETQWTVLQSSLHLT (SEQ ID NO 191) was investigated for necessary amino acids by the synthesis of 2 peptides that had been moved 2 amino acids compared to the original peptide, peptide E4:4N (SEQ ID NO:187) (RLSSDQDQSQTPETPATPLS) and peptide E4:4C (SEQ ID NO:188) (DQDQSQTPETPATPLSCCTE). The peptides were tested and compared with peptide E4:4 (SEQ ID NO:39) in IgA and IgG ELISAs in the same panel of 30 human sera. Both the peptide E4:4N (SEQ ID NO:187) and the peptide E4:4C (SEQ ID NO:188) were unreactive (no serum produced any optical density above 0.1) (not shown). The E4 peptide (SEQ ID NO:189) DQDQSQTPETP was synthesized in a previous work (Schoolnik, EP 0 257 754). Since the non-reactivity of peptides E4:4N (SEQ ID NO:187) and E4:4C (SEQ ID NO:188) implies that both the first residues SS and the last residues CC of peptide E4:4 (SEQ ID NO:39) are essential for its reactivity, we think that the peptide E4:4 (SEQ ID NO:39) represents a new invention with an immunoreactivity that was not present in this previously described peptide.

Epitopes in the E4 Protein Requiring 30 Amino Acids Peptides.

The finding of an epitope in the E7 open reading frame that was 30 amino acids long prompted an additional test of the E4 open reading frame with overlapping 30 residues synthetic peptides. The following peptides were synthesized:

Ala Asp Pro Ala Ala Ala Thr Lys Tyr Pro Leu Leu Lys Leu Leu Gly Ser Thr Trp Pro Thr Thr Pro Pro Arg Pro Ile Pro Lys Pro (SEQ ID NO:41); Trp Pro Thr Thr Pro Pro Arg Pro Ile Pro Lys Pro Ser Pro Trp Ala Pro Lys Lys His Arg Arg Leu Ser Ser Asp Gln Asp Gln Ser (SEQ ID NO:42); KHRRLSSDQDQSQTPETPATPLSCCTETQW (SEQ ID NO:189); QSQTPETPATPLSCCTETQWTVLQSSLHLT (SEQ ID NO:190); TETQWTVLQSSLHLTAHTKDG-LTVIVTLHP (SEQ ID NO:192)

The peptides were tested in IgA ELISAs with a panel of 30 human sera from CIN patients.

Peptide Ala Asp Pro Ala Ala Ala Thr Lys Tyr Pro Leu Leu Lys Leu Leu Gly Ser Thr Trp Pro Thr Thr Pro Pro Arg Pro Ile Pro Lys Pro (SEQ ID NO:41)

IgA: 0.234, 0, 0, 0, 0, 0, 0, 0, 0, 0, 0, 0, 0, 0, 0, 0, 0, 0, 0.106, 0, 0, 0, 0.171, 0, 0, 0, 0, 0, 0.202.

Peptide Trp Pro Thr Thr Pro Pro Arg Pro Ile Pro Lys Pro Ser Pro Trp Ala Pro Lys Lys His Arg Arg Leu Ser Ser Asp Gln Asp Gln Ser (SEQ ID NO:42)

IgA: 0.199, 0, 0, 0.148, 0, 0, 0.662, 0, 0, 0.119, 0, 0, 0, 0.121, 0, 0, 0,0, 0, 0, 0, 0, 0.724, 0, 0, 0, 0, 0.141, 0.248, 0.136.

The peptide (SEQ ID NO:193) KHRRLSSDQDQSQTPE-TPATPLSCCTETQW showed an immunoreactivity that was strongly correlated to, but somewhat lesser than the reactivity of peptide Ser Ser Asp Gln Asp Gln Ser Gln Thr Pro Glu Thr Pro Ala Thr Pro Leu Ser Cys Cys (SEQ ID NO:39) (not shown). The peptides (SEQ ID NO:191) QSQTPET-PATPLSCCTETQWTVLQSSLHLT and (SEQ ID NO:191) TETQWTVLQSSLHLTAHTKDGLTVIVTLHP reacted with 2 out of 30 sera in the IgA ELISA (not shown).

Antibodies in Cervical Secretions

The major immunoreactive peptides were also tested in IgA and IgG ELISAs with cervical secretions from 30 women with cervical intraepithelial neoplasia (CIN) or with a history of CIN. It was found that those peptides which were the most immunoreactive with serum also were those which were most reactive with cervical secretions.

The results are exemplified with peptide E2:9 (SEQ ID NO:136) (FDGDICNTMHYTNWTHIYIC). IgA-ELISA where the results are given as optical densities for a 1:2 dilution of the secretion:

0.063, 0, 0.059, 0, 0.091, 0.456, 0.074, 0, 0, 0, 0.177, 0, 1.563, 0, 0.124, 0, 0, 0, 0, 0, 0.104, 0.083, 0, 0, 0, 0.068, 0, 0, 0, 0.150.

IgG-ELISA also at a 1:2 dilution of the secretion:

0.080, 0, 0, 0, 0.067, 0.262, 0.110, 0, 0, 0, 0.131, 0, 0.092, 0, 0, 0, 0, 0, 0, 0, 0, 0, 0, 0, 0, 0, 0, 0, 0, 0.070.

As seen from the results shown above, IgA was the major Ig class in secretions. An ELISA was also performed on serum from the same patients. Comparison of the IgG—results for serum and secretions showed a strong correlation, whereas no obvious correlation was seen between IgA in serum and secretions (not shown). This suggests that most of the IgA found in secretions was produced locally, whereas the IgG found in secretions may be due to a leakage of serum antibodies into the secretions.

In summary, these results show that several immunoreactive peptides based on both HPV 1, 5, 6, 8, 11, 16, 18, 31, 33 and 56 have been found. The immunoreactivity is quite different depending on if IgG, IgA or IgM is measured. The method used here, ELISA, is only one of several variants of immunoasssay, but the most simple and most practical method for testing sera on a large scale.

We claim:

1. A method for detecting the presence of human papillomavirus antibody, and papillomavirus associated diseases comprising:

contacting a sample with a peptide specific for human papillomavirus E7 protein, wherein the peptide is SEQ ID NO: 3, 9, 12, 15, 52, 53, 54, 60, 61, 62, 63, 64, 65, 66, 71, 76, 79, 152, 153, 154, 155, 156, 157, 186, or 193;

detecting a level of peptide binding in said sample;

comparing said level of peptide binding in said sample to a level of peptide binding in a control sample; and quantitating said level of peptide binding in said sample, wherein said level of peptide binding in said sample which is greater than said level of peptide binding in said control sample indicates the presence of human papillomavirus antibody and papillomavirus associated diseases.

2. The method according to claim 1, wherein said detecting comprises contacting said sample and said peptide specific for human papillomavirus E7 protein with a monoclonal antibody specific for an immunoglobin selected from the group of immunoglobins consisting of: IgG; IgA; and IgM.

3. The method according to claim 1, wherein said contacting and detecting comprises an immunoassay selected from the group consisting of: ELISA; immunofluorescence; and immunohistocytochemistry.

4. The method according to claim 1, wherein said sample is selected from the group consisting of: serum; cervical secretions; cervical tissue; and skin.

5. The method according to claim 1, wherein said papillomavirus is present in cervix cancer, condyloma, CIN, warts, and squamous cell carcinoma.

* * * * *

SEQUENCE LISTING (1) GENERAL INFORMATION:

(iii) NUMBER OF SEQUENCES: 193

(2) INFORMATION FOR SEQ ID NO: 1:

(i) SEQUENCE CHARACTERISTICS:
         (A) LENGTH: 19 amino acids
         (B) TYPE: amino acid
         (C) TOPOLOGY: linear (ii) MOLECULE TYPE: peptide (xi) SEQUENCE DESCRIPTION: SEQ ID NO: 1:

Ile Gly Ser Ala Arg Met Leu Val Lys Phe Ile Asp Glu Ala Gln Arg
     1               5                   10                  15

Glu Lys Cys (2) INFORMATION FOR SEQ ID NO: 2:

(i) SEQUENCE CHARACTERISTICS:
         (A) LENGTH: 20 amino acids
         (B) TYPE: amino acid
         (D) TOPOLOGY: linear (ii) MOLECULE TYPE: peptide (xi) SEQUENCE DESCRIPTION: SEQ ID NO: 2:

Tyr Asp Asn Asn Pro Asp Asn Gln Thr Arg His Thr Ile Trp Asn His
     1               5                   10                  15

Val Tyr Tyr Gln
                 20

(2) INFORMATION FOR SEQ ID NO: 3:

(i) SEQUENCE CHARACTERISTICS:
         (A) LENGTH: 30 amino acids
         (B) TYPE: amino acid
         (D) TOPOLOGY: linear (ii) MOLECULE TYPE: peptide (xi) SEQUENCE DESCRIPTION: SEQ ID NO: 3:

Cys Ala Tyr Cys Glu Lys Leu Val Arg Leu Thr Val Leu Ala Asp His
     1               5                   10                  15

Ser Ala Ile Arg Gln Leu Glu Glu Leu Leu Leu Arg Ser Leu
                 20                  25                  30

(2) INFORMATION FOR SEQ ID NO: 4:

(i) SEQUENCE CHARACTERISTICS:
         (A) LENGTH: 22 amino acids
         (B) TYPE: amino acid
         (D) TOPOLOGY: linear (ii) MOLECULE TYPE: peptide (xi) SEQUENCE DESCRIPTION: SEQ ID NO: 4:

Leu Gly Ser Ser Leu Ala Ala Lys Cys Pro Glu Gln Ala Pro Pro Glu
     1               5                   10                  15

Pro Gln Thr Asp Pro Tyr
                 20

(2) INFORMATION FOR SEQ ID NO: 5:

(i) SEQUENCE CHARACTERISTICS:
    (A) LENGTH: 20 amino acids
    (B) TYPE: amino acid
    (D) TOPOLOGY: linear (ii) MOLECULE TYPE: peptide (xi) SEQUENCE DESCRIPTION: SEQ ID NO: 5:

Asp Ile Pro Leu Val Glu Leu Asn Leu Gly Leu Glu Thr Asp Thr Ser
   1               5                  10                  15

Ser Val Val Gln
              20

(2) INFORMATION FOR SEQ ID NO: 6:

(i) SEQUENCE CHARACTERISTICS:
       (A) LENGTH: 19 amino acids
       (B) TYPE: amino acid
       (D) TOPOLOGY: linear (ii) MOLECULE TYPE: peptide (xi) SEQUENCE DESCRIPTION: SEQ ID NO: 6:

Leu Gly Arg Pro Arg Met Leu Ile Ser Phe Ser Ser Tyr Thr Gln Arg
     1               5                  10                  15

Arg Asp Cys (2) INFORMATION FOR SEQ ID NO: 7:

(i) SEQUENCE CHARACTERISTICS:
       (A) LENGTH: 20 amino acids
       (B) TYPE: amino acid
       (D) TOPOLOGY: linear (ii) MOLECULE TYPE: peptide (xi) SEQUENCE DESCRIPTION: SEQ ID NO: 7:

Phe Asp Gly Cys Ala Asn Asn Thr Met Asp Tyr Val Val Trp Thr Asp
     1               5                  10                  15

Val Tyr Val Gln
                20

(2) INFORMATION FOR SEQ ID NO: 8:

(i) SEQUENCE CHARACTERISTICS:
       (A) LENGTH: 20 amino acids
       (B) TYPE: amino acid
       (D) TOPOLOGY: linear (ii) MOLECULE TYPE: peptide (xi) SEQUENCE DESCRIPTION: SEQ ID NO: 8:

Arg Leu Gly Asn Glu His Glu Glu Ser Asn Ser Pro Leu Ala Thr Pro
     1               5                  10                  15

Cys Val Trp Pro
                20

(2) INFORMATION FOR SEQ ID NO: 9:

(i) SEQUENCE CHARACTERISTICS:
       (A) LENGTH: 30 amino acids
       (B) TYPE: amino acid
       (D) TOPOLOGY: linear (ii) MOLECULE TYPE: peptide (xi) SEQUENCE DESCRIPTION: SEQ ID NO: 9:

```
        Cys Cys Gly Cys Asp Ser Asn Val Arg Leu Val Val Gln Cys Thr Glu
        1               5                   10                  15

Thr Asp Ile Arg Glu Val Gln Gln Leu Leu Leu Gly Thr Leu
                        20                  25                  30
```

(2) INFORMATION FOR SEQ ID NO: 10:

(i) SEQUENCE CHARACTERISTICS:
      (A) LENGTH: 20 amino acids
      (B) TYPE: amino acid
      (D) TOPOLOGY: linear (ii) MOLECULE TYPE: peptide (xi) SEQUENCE DESCRIPTION: SEQ ID NO: 10:

```
        Pro Leu Asp Thr Phe Val Val Ser Ser Asp Ser Gly Pro Thr Ser
        1               5                   10                  15

Ser Thr Pro Val
                        20
```

(2) INFORMATION FOR SEQ ID NO: 11:

(i) SEQUENCE CHARACTERISTICS:
      (A) LENGTH: 19 amino acids
      (B) TYPE: amino acid
      (D) TOPOLOGY: linear (ii) MOLECULE TYPE: peptide (xi) SEQUENCE DESCRIPTION: SEQ ID NO: 11:

```
        Leu Gly Arg Ser Arg Met Leu Ile Leu Phe Thr Ser Ala Gly Gln Arg
        1               5                   10                  15

Lys Asp Cys
```

(2) INFORMATION FOR SEQ ID NO: 12:

(i) SEQUENCE CHARACTERISTICS:
      (A) LENGTH: 30 amino acids
      (B) TYPE: amino acid
      (D) TOPOLOGY: linear (ii) MOLECULE TYPE: peptide (xi) SEQUENCE DESCRIPTION: SEQ ID NO: 12:

```
        Cys Ser Cys Cys Gln Val Lys Leu Arg Leu Phe Val Asn Ala Thr Asp
        1               5                   10                  15

Ser Gly Ile Arg Thr Phe Gln Glu Leu Leu Phe Arg Asp Leu
                        20                  25                  30
```

(2) INFORMATION FOR SEQ ID NO: 13:

(i) SEQUENCE CHARACTERISTICS:
      (A) LENGTH: 20 amino acids
      (B) TYPE: amino acid
      (D) TOPOLOGY: linear (ii) MOLECULE TYPE: peptide (xi) SEQUENCE DESCRIPTION: SEQ ID NO: 13:

```
        Phe Asp Gly Cys Glu Asp Asn Val Met Glu Tyr Val Val Trp Thr His
        1               5                   10                  15

Ile Tyr Leu Gln
                        20
```

(2) INFORMATION FOR SEQ ID NO: 14:

(i) SEQUENCE CHARACTERISTICS:
    (A) LENGTH: 20 amino acids
    (B) TYPE: amino acid
    (D) TOPOLOGY: linear (ii) MOLECULE TYPE: peptide (xi) SEQUENCE DESCRIPTION: SEQ ID NO: 14:

Arg Arg Arg Leu Gly Ser Glu His Val Asp Arg Pro Leu Thr Thr Pro
1               5                   10                  15

Cys Val Trp Pro
            20

(2) INFORMATION FOR SEQ ID NO: 15:

(i) SEQUENCE CHARACTERISTICS:
    (A) LENGTH: 30 amino acids
    (B) TYPE: amino acid
    (D) TOPOLOGY: linear (ii) MOLECULE TYPE: peptide (xi) SEQUENCE DESCRIPTION: SEQ ID NO: 15:

Cys Cys Gly Cys Asp Ser Asn Val Arg Leu Val Val Gly Cys Thr Asp
1               5                   10                  15

Gly Asp Ile Arg Gln Leu Gln Asp Leu Leu Gly Thr Leu
            20                  25                  30

(2) INFORMATION FOR SEQ ID NO: 16:

(i) SEQUENCE CHARACTERISTICS:
    (A) LENGTH: 21 amino acids
    (B) TYPE: amino acid
    (D) TOPOLOGY: linear (ii) MOLECULE TYPE: peptide (xi) SEQUENCE DESCRIPTION: SEQ ID NO: 16:

Gln Ser Gln Ala Ile Thr Cys Gln Lys Pro Thr Pro Glu Lys Glu Lys
1               5                   10                  15

Gln Asp Pro Tyr Lys
            20

(2) INFORMATION FOR SEQ ID NO: 17:

(i) SEQUENCE CHARACTERISTICS:
    (A) LENGTH: 20 amino acids
    (B) TYPE: amino acid
    (D) TOPOLOGY: linear (ii) MOLECULE TYPE: peptide (xi) SEQUENCE DESCRIPTION: SEQ ID NO: 17:

Pro Leu Asp Thr Phe Val Val Ser Ser Asp Ser Gly Pro Thr Ser
1               5                   10                  15

Ser Thr Pro Leu
            20

(2) INFORMATION FOR SEQ ID NO: 18:

(i) SEQUENCE CHARACTERISTICS:
    (A) LENGTH: 20 amino acids
    (B) TYPE: amino acid
    (D) TOPOLOGY: linear (ii) MOLECULE TYPE: peptide (xi) SEQUENCE DESCRIPTION: SEQ ID NO: 18:

Lys Gln His Arg Asp Ala Val Gln Val Leu Lys Arg Lys Tyr Leu Gly
    1               5                  10                  15

Ser Cys Ile Glu
                20

(2) INFORMATION FOR SEQ ID NO: 19:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 19:

Gln Tyr Ser Gly Gly Ser Gly Gly Cys Ser Gln Tyr Ser Ser Gly
    1               5                  10                  15

Ser Gly Gly Glu
                20

(2) INFORMATION FOR SEQ ID NO: 20:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 20:

Gly Ser Gly Gly Glu Gly Val Ser Glu Arg His Thr Ile Cys Gln Thr
    1               5                  10                  15

Pro Leu Thr Asn
                20

(2) INFORMATION FOR SEQ ID NO: 21:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 21:

Lys Ala Ala Met Leu Ala Lys Phe Lys Glu Leu Tyr Gly Val Ser Phe
    1               5                  10                  15

Ser Glu Leu Val
                20

(2) INFORMATION FOR SEQ ID NO: 22:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 22:

Asp Ser Ile Lys Thr Leu Leu Gln Gln Tyr Cys Leu Tyr Leu His Ile
    1               5                  10                  15

Gln Ser Leu Ala
                20

(2) INFORMATION FOR SEQ ID NO: 23:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 23:

```
Ser Lys Ser His Phe Trp Leu Gln Pro Leu Ala Asp Ala Lys Ile Gly
 1               5                  10                  15

Met Leu Asp Asp
        20
```

(2) INFORMATION FOR SEQ ID NO: 24:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 24:

```
Gly Met Leu Asp Asp Ala Thr Val Pro Cys Trp Asn Tyr Ile Asp Asp
 1               5                  10                  15

Asn Leu Arg Asn
        20
```

(2) INFORMATION FOR SEQ ID NO: 25:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 25:

```
Leu His Asn Arg Leu Val Val Phe Thr Phe Pro Asn Glu Phe Pro Phe
 1               5                  10                  15

Asp Glu Asn Gly
        20
```

(2) INFORMATION FOR SEQ ID NO: 26:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO: 26:

```
Phe Asp Glu Asn Gly Asn Pro Val Tyr Glu Leu Asn Asp Lys Asn Trp
 1               5                  10                  15

Lys Ser
```

(2) INFORMATION FOR SEQ ID NO: 27:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO: 27:

Asp Ser Leu Pro Thr Phe Lys Cys Val Ser Gly Gln Asn Thr Asn Thr
1               5                   10                  15

Leu (2) INFORMATION FOR SEQ ID NO: 28:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 28:

Gly Asp Ile Cys Asn Thr Met His Tyr Thr Asn Trp Thr His Ile Tyr
1               5                   10                  15

Ile Cys Glu Glu
            20

(2) INFORMATION FOR SEQ ID NO: 29:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 29:

Leu Thr His Tyr Glu Asn Asp Ser Thr Asp Leu Arg Asp His Ile Asp
1               5                   10                  15

Tyr Trp Lys His
            20

(2) INFORMATION FOR SEQ ID NO: 30:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 30:

Pro Thr Gly Cys Ile Lys Lys His Gly Tyr Thr Val Glu Val Gln Phe
1               5                   10                  15

Asp Gly Asp Ile
            20

(2) INFORMATION FOR SEQ ID NO: 31:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 31:

Phe Asp Gly Asp Ile Cys Asn Thr Met His Tyr Thr Asn Trp Thr His
1               5                   10                  15

Ile Tyr Ile Cys
            20

(2) INFORMATION FOR SEQ ID NO: 32:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 32:

```
His Ile Tyr Ile Cys Glu Glu Ala Ser Val Thr Val Val Glu Gly Gln
  1               5                  10                  15
Val Asp Tyr Tyr
            20
```

(2) INFORMATION FOR SEQ ID NO: 33:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 33:

```
Gln Val Asp Tyr Tyr Gly Leu Tyr Tyr Val His Glu Gly Ile Arg Thr
  1               5                  10                  15
Tyr Phe Val Gln
            20
```

(2) INFORMATION FOR SEQ ID NO: 34:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 34:

```
Thr Tyr Phe Val Gln Phe Lys Asp Asp Ala Glu Lys Tyr Ser Lys Asn
  1               5                  10                  15
Lys Val Trp Glu
            20
```

(2) INFORMATION FOR SEQ ID NO: 35:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 35:

```
Asn Lys Val Trp Glu Val His Ala Gly Gly Gln Val Ile Leu Cys Pro
  1               5                  10                  15
Thr Ser Val Phe
            20
```

(2) INFORMATION FOR SEQ ID NO: 36:

(i) SEQUENCE CHARACTERISTICS:
        (A) LENGTH: 20 amino acids
        (B) TYPE: amino acid
        (D) TOPOLOGY: linear -continued

```
    (ii) MOLECULE TYPE: peptide (xi) SEQUENCE DESCRIPTION: SEQ ID NO: 36:

Ala Val Ala Leu Gly Thr Glu Glu Thr Gln Thr Thr Ile Gln Arg Pro
       1               5                   10                  15

Arg Ser Glu Pro
                   20

(2) INFORMATION FOR SEQ ID NO: 37:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 37:

Pro Arg Ser Glu Pro Asp Thr Gly Asn Pro Cys His Thr Thr Lys Leu
       1               5                   10                  15

Leu His Arg Asp
                   20

(2) INFORMATION FOR SEQ ID NO: 38:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 38:

Phe Asn Ser Ser His Lys Gly Arg Ile Asn Cys Asn Ser Asn Thr Thr
       1               5                   10                  15

Pro Ile Val His
                   20

(2) INFORMATION FOR SEQ ID NO: 39:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 39:

Ser Ser Asp Gln Asp Gln Ser Gln Thr Pro Glu Thr Pro Ala Thr Pro
       1               5                   10                  15

Leu Ser Cys Cys
                   20

(2) INFORMATION FOR SEQ ID NO: 40:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 40:

Ile Pro Lys Pro Ser Pro Trp Ala Pro Lys Lys His Arg Arg Leu Ser
       1               5                   10                  15

Ser Asp Gln Asp
```

20

(2) INFORMATION FOR SEQ ID NO: 41:

(i) SEQUENCE CHARACTERISTICS:
      (A) LENGTH: 30 amino acids
      (B) TYPE: amino acid
      (D) TOPOLOGY: linear (ii) MOLECULE TYPE: peptide (xi) SEQUENCE DESCRIPTION: SEQ ID NO: 41:

```
Ala Asp Pro Ala Ala Ala Thr Lys Tyr Pro Leu Leu Lys Leu Leu Gly
1               5                   10                  15

Ser Thr Trp Pro Thr Thr Pro Pro Arg Pro Ile Pro Lys Pro
                20                  25                  30
```

(2) INFORMATION FOR SEQ ID NO: 42:

(i) SEQUENCE CHARACTERISTICS:
      (A) LENGTH: 30 amino acids
      (B) TYPE: amino acid
      (D) TOPOLOGY: linear (ii) MOLECULE TYPE: peptide (xi) SEQUENCE DESCRIPTION: SEQ ID NO: 42:

```
Trp Pro Thr Thr Pro Pro Arg Pro Ile Pro Lys Pro Ser Pro Trp Ala
1               5                   10                  15

Pro Lys Lys His Arg Arg Leu Ser Ser Asp Gln Asp Gln Ser
                20                  25                  30
```

(2) INFORMATION FOR SEQ ID NO: 43:

(i) SEQUENCE CHARACTERISTICS:
      (A) LENGTH: 20 amino acids
      (B) TYPE: amino acid
      (D) TOPOLOGY: linear (ii) MOLECULE TYPE: peptide (xi) SEQUENCE DESCRIPTION: SEQ ID NO: 43:

```
Thr Asn Leu Asp Thr Ala Ser Thr Thr Leu Leu Ala Cys Phe Leu Leu
1               5                   10                  15

Cys Phe Cys Val
                20
```

(2) INFORMATION FOR SEQ ID NO: 44:

(i) SEQUENCE CHARACTERISTICS:
      (A) LENGTH: 20 amino acids
      (B) TYPE: amino acid
      (D) TOPOLOGY: linear (ii) MOLECULE TYPE: peptide (xi) SEQUENCE DESCRIPTION: SEQ ID NO: 44:

```
Tyr Ser Lys Ile Ser Glu Tyr Arg His Tyr Cys Tyr Ser Leu Tyr Gly
1               5                   10                  15

Thr Thr Leu Glu
                20
```

(2) INFORMATION FOR SEQ ID NO: 45:

(i) SEQUENCE CHARACTERISTICS:
      (A) LENGTH: 20 amino acids
      (B) TYPE: amino acid (D) TOPOLOGY: linear (ii) MOLECULE TYPE: peptide (xi) SEQUENCE DESCRIPTION: SEQ ID NO: 45:

Gly Thr Thr Leu Glu Gln Gln Tyr Asn Lys Pro Leu Cys Asp Leu Leu
          1               5                  10                  15

Ile Arg Cys Ile
                    20

(2) INFORMATION FOR SEQ ID NO: 46:

(i) SEQUENCE CHARACTERISTICS:
           (A) LENGTH: 20 amino acids
           (B) TYPE: amino acid
           (D) TOPOLOGY: linear (ii) MOLECULE TYPE: peptide (xi) SEQUENCE DESCRIPTION: SEQ ID NO: 46:

His Gly Asp Thr Pro Thr Leu His Glu Tyr Met Leu Asp Leu Gln Pro
          1               5                  10                  15

Glu Thr Thr Asp
                    20

(2) INFORMATION FOR SEQ ID NO: 47:

(i) SEQUENCE CHARACTERISTICS:
           (A) LENGTH: 20 amino acids
           (B) TYPE: amino acid
           (D) TOPOLOGY: linear (ii) MOLECULE TYPE: peptide (xi) SEQUENCE DESCRIPTION: SEQ ID NO: 47:

Pro Glu Thr Thr Asp Leu Tyr Cys Tyr Glu Gln Leu Asn Asp Ser Ser
          1               5                  10                  15

Glu Glu Glu Asp
                    20

(2) INFORMATION FOR SEQ ID NO: 48:

(i) SEQUENCE CHARACTERISTICS:
           (A) LENGTH: 20 amino acids
           (B) TYPE: amino acid
           (D) TOPOLOGY: linear (ii) MOLECULE TYPE: peptide (xi) SEQUENCE DESCRIPTION: SEQ ID NO: 48:

Pro Asp Arg Ala His Tyr Asn Ile Val Thr Phe Cys Cys Lys Cys Asp
          1               5                  10                  15

Ser Thr Leu Arg
                    20

(2) INFORMATION FOR SEQ ID NO: 49:

(i) SEQUENCE CHARACTERISTICS:
           (A) LENGTH: 21 amino acids
           (B) TYPE: amino acid
           (D) TOPOLOGY: linear (ii) MOLECULE TYPE: peptide (xi) SEQUENCE DESCRIPTION: SEQ ID NO: 49:

Asp Ser Thr Leu Arg Leu Cys Val Gln Ser Thr His Val Asp Ile Arg
          1               5                  10                  15

```
       Thr Leu Glu Asp Leu
                 20

(2) INFORMATION FOR SEQ ID NO: 50:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 50:

Thr Leu Glu Asp Leu Leu Met Gly Thr Leu Gly Ile Val Cys Pro Ile
       1               5                  10                  15

Cys Ser Gln Lys Pro
                 20

(2) INFORMATION FOR SEQ ID NO: 51:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO: 51:

His Gly Asp Thr Pro Thr Leu His Glu Tyr Met Leu Asp Leu Gln Pro
       1               5                  10                  15

Glu Thr Thr Asp Leu Tyr Cys Tyr Glu Gln Leu Asn Asp Ser
                     20                  25                  30

(2) INFORMATION FOR SEQ ID NO: 52:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO: 52:

Gln Ala Glu Pro Asp Arg Ala His Tyr Asn Ile Val Thr Phe Cys Cys
       1               5                  10                  15

Lys Cys Asp Ser Thr Leu Arg Leu Cys Val Gln Ser Thr His
                     20                  25                  30

(2) INFORMATION FOR SEQ ID NO: 53:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO: 53:

Cys Cys Lys Cys Asp Ser Thr Leu Arg Leu Cys Val Gln Ser Thr His
       1               5                  10                  15

Val Asp Ile Arg Thr Leu Glu Asp Leu Leu Met Gly Thr Leu
                     20                  25                  30

(2) INFORMATION FOR SEQ ID NO: 54:

(i) SEQUENCE CHARACTERISTICS:
```

(A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO: 54:

Val Gln Ser Thr His Val Asp Ile Arg Thr Leu Glu Asp Leu Leu Met
    1               5                   10                  15

Gly Thr Leu Gly Ile Val Cys Pro Ile Cys Ser Gln Lys Pro
                20                  25                  30

(2) INFORMATION FOR SEQ ID NO: 55:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 55:

Val Thr Ser Gln Ala Ile Ala Cys Gln Lys His Thr Pro Pro Ala Pro
    1               5                   10                  15

Lys Glu Asp Pro Leu
                20

(2) INFORMATION FOR SEQ ID NO: 56:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO: 56:

Val His Thr Gly Phe Gly Ala Met Asp Phe Thr Thr Leu Gln Ala Gly
    1               5                   10                  15

Gly Cys (2) INFORMATION FOR SEQ ID NO: 57:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO: 57:

Gly Gly Thr Leu Glu Asp Thr Tyr Arg Phe Gly Gly Cys
    1               5                   10

(2) INFORMATION FOR SEQ ID NO: 58:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 58:

Phe Asp Gly Asn Lys Asp Asn Cys Met Thr Tyr Val Ala Trp Asp Ser
    1               5                   10                  15

Val Tyr Tyr Met

20

(2) INFORMATION FOR SEQ ID NO: 59:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 59:

Ser Leu Leu Asn Ser Tyr Ser Thr Pro Pro His Arg Ile Pro Ala Pro
      1               5                  10                  15

Cys Pro Trp Ala
                20

(2) INFORMATION FOR SEQ ID NO: 60:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO: 60:

Cys Cys Lys Cys Glu Ala Arg Ile Glu Leu Val Val Glu Ser Ser Ala
      1               5                  10                  15

Asp Asp Leu Arg Ala Phe Gln Gln Leu Phe Leu Asn Thr Leu
                      20                  25                  30

(2) INFORMATION FOR SEQ ID NO: 61:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO: 61:

His Gly Pro Lys Ala Thr Leu Gln Asp Ile Val Leu His Leu Glu Pro
      1               5                  10                  15

Gln Asn Glu Ile Pro Val Asp Leu Leu Cys His Glu Gln Leu
                      20                  25                  30

(2) INFORMATION FOR SEQ ID NO: 62:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO: 62:

Pro Gln Asn Glu Ile Pro Val Asp Leu Leu Cys His Glu Gln Leu Ser
      1               5                  10                  15

Asp Ser Glu Glu Glu Asn Asp Glu Ile Asp Gly Val Asn His
                      20                  25                  30

(2) INFORMATION FOR SEQ ID NO: 63:

(i) SEQUENCE CHARACTERISTICS:
        (A) LENGTH: 30 amino acids
        (B) TYPE: amino acid (D) TOPOLOGY: linear (ii) MOLECULE TYPE: peptide (xi) SEQUENCE DESCRIPTION: SEQ ID NO: 63:

Ser Asp Ser Glu Glu Glu Asn Asp Glu Ile Asp Gly Val Asn His Gln
     1               5                   10                  15

His Leu Pro Ala Arg Arg Ala Glu Pro Gln Arg His Thr Met
                 20                  25                  30

(2) INFORMATION FOR SEQ ID NO: 64:

(i) SEQUENCE CHARACTERISTICS:
       (A) LENGTH: 30 amino acids
       (B) TYPE: amino acid
       (D) TOPOLOGY: linear (ii) MOLECULE TYPE: peptide (xi) SEQUENCE DESCRIPTION: SEQ ID NO: 64:

Gln His Leu Pro Ala Arg Arg Ala Glu Pro Gln Arg His Thr Met Leu
     1               5                   10                  15

Cys Met Cys Cys Lys Cys Glu Ala Arg Ile Glu Leu Val Val
                 20                  25                  30

(2) INFORMATION FOR SEQ ID NO: 65:

(i) SEQUENCE CHARACTERISTICS:
       (A) LENGTH: 30 amino acids
       (B) TYPE: amino acid
       (D) TOPOLOGY: linear (ii) MOLECULE TYPE: peptide (xi) SEQUENCE DESCRIPTION: SEQ ID NO: 65:

Leu Cys Met Cys Cys Lys Cys Glu Ala Arg Ile Glu Leu Val Val Glu
     1               5                   10                  15

Ser Ser Ala Asp Asp Leu Arg Ala Phe Gln Gln Leu Phe Leu
                 20                  25                  30

(2) INFORMATION FOR SEQ ID NO: 66:

(i) SEQUENCE CHARACTERISTICS:
       (A) LENGTH: 29 amino acids
       (B) TYPE: amino acid
       (D) TOPOLOGY: linear (ii) MOLECULE TYPE: peptide (xi) SEQUENCE DESCRIPTION: SEQ ID NO: 66:

Glu Ser Ser Ala Asp Asp Leu Arg Ala Phe Gln Gln Leu Phe Leu Asn
     1               5                   10                  15

Thr Leu Ser Phe Val Cys Pro Trp Cys Ala Ser Gln Gln
                 20                  25

(2) INFORMATION FOR SEQ ID NO: 67:

(i) SEQUENCE CHARACTERISTICS:
       (A) LENGTH: 21 amino acids
       (B) TYPE: amino acid
       (D) TOPOLOGY: linear (ii) MOLECULE TYPE: peptide (xi) SEQUENCE DESCRIPTION: SEQ ID NO: 67:

Gln Ser Val Ala Ile Thr Cys Gln Lys Asp Ala Ala Pro Ala Glu Asn
     1               5                   10                  15

```
        Lys Asp Pro Tyr Asp
                     20
```

(2) INFORMATION FOR SEQ ID NO: 68:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 68:

```
  Pro Leu Gln Thr Phe Ala Ser Ser Gly Thr Gly Glu Glu Pro Ile Ser
  1               5                  10                  15

Ser Thr Pro Leu
                20
```

(2) INFORMATION FOR SEQ ID NO: 69:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 69:

```
  Phe Asp Gly Asp Val His Asn Thr Met His Tyr Thr Asn Trp Lys Phe
  1               5                  10                  15

Ile Tyr Leu Cys
                20
```

(2) INFORMATION FOR SEQ ID NO: 70:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO: 70:

```
  His Lys Asn Ala Ile Val Thr Leu Thr Tyr Ile Ser Thr Ser Gln Arg
  1               5                  10                  15

Asp Asp Cys
```

(2) INFORMATION FOR SEQ ID NO: 71:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO: 71:

```
  Cys Cys Gln Cys Lys Ser Thr Leu Arg Leu Cys Val Gln Ser Thr Gln
  1               5                  10                  15

Val Asp Ile Arg Ile Leu Gln Glu Leu Leu Met Gly Ser Phe
                20                  25                  30
```

(2) INFORMATION FOR SEQ ID NO: 72:

(i) SEQUENCE CHARACTERISTICS:
        (A) LENGTH: 21 amino acids (B) TYPE: amino acid
            (D) TOPOLOGY: linear (ii) MOLECULE TYPE: peptide (xi) SEQUENCE DESCRIPTION: SEQ ID NO: 72:

Thr Ser Gln Ala Ile Thr Cys Gln Lys Thr Ala Pro Gln Lys Pro Lys
    1               5                   10                  15

Glu Asp Pro Phe Lys
                20

(2) INFORMATION FOR SEQ ID NO: 73:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 73:

Pro Met Asp Thr Phe Ile Val Ser Thr Asn Asn Gln Asn Ile Thr Ser
    1               5                   10                  15

Ser Thr Pro Ile
                20

(2) INFORMATION FOR SEQ ID NO: 74:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 74:

Tyr Asp Asn Asp Lys Lys Asn Thr Met Asp Tyr Thr Asn Trp Gly Glu
    1               5                   10                  15

Ile Tyr Ile Ile
                20

(2) INFORMATION FOR SEQ ID NO: 75:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 75:

Pro Gln Thr Pro Pro Ser Pro Leu Gln Ser Cys Ser Val Gln Thr Pro
    1               5                   10                  15

Pro Trp Thr Ile
                20

(2) INFORMATION FOR SEQ ID NO: 76:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO: 76:

Cys His Thr Cys Asn Thr Thr Val Arg Leu Cys Val Asn Ser Thr Ala

```
                1               5              10              15

Ser Asp Leu Arg Thr Ile Gln Gln Leu Leu Met Gly Thr Val
                              20              25              30

(2) INFORMATION FOR SEQ ID NO: 77:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 77:

Thr Ser Gln Ala Ile Thr Cys Gln Lys Thr Val Pro Pro Lys Glu Lys
      1               5              10              15

Glu Asp Pro Leu Gly
                    20

(2) INFORMATION FOR SEQ ID NO: 78:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 78:

Pro Met Asp Thr Phe Val Val Ser Thr Asp Ser Ser Asn Val Thr Ser
      1               5              10              15

Ser Thr Pro Ile
                  20

(2) INFORMATION FOR SEQ ID NO: 79:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO: 79:

Cys Cys Glu Cys Lys Phe Val Val Gln Leu Asp Ile Gln Ser Thr Lys
      1               5              10              15

Glu Asp Leu Arg Val Val Gln Gln Leu Leu Met Gly Ala Leu
                      20              25              30

(2) INFORMATION FOR SEQ ID NO: 80:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO: 80:

His Lys Ser Ala Ile Val Thr Leu Thr Tyr Asp Ser Glu Trp Gln Arg
      1               5              10              15

Asp Gln Cys (2) INFORMATION FOR SEQ ID NO: 81:

(i) SEQUENCE CHARACTERISTICS:
```

(A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 81:

Thr Asn Leu Asn Thr Ala Ser Thr Thr Leu Leu Ala Cys Phe Leu Leu
      1               5                  10                  15

Cys Phe Cys Val
              20

(2) INFORMATION FOR SEQ ID NO: 82:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 82:

Leu Cys Phe Cys Val Leu Leu Cys Val Cys Leu Leu Ile Arg Pro Leu
      1               5                  10                  15

Leu Leu Ser Val
              20

(2) INFORMATION FOR SEQ ID NO: 83:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 83:

Leu Leu Leu Ser Val Ser Thr Tyr Thr Ser Leu Ile Ile Leu Val Leu
      1               5                  10                  15

Leu Leu Trp Ile
              20

(2) INFORMATION FOR SEQ ID NO: 84:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 84:

Leu Leu Leu Trp Ile Thr Ala Ala Ser Ala Phe Arg Cys Phe Ile Val
      1               5                  10                  15

Tyr Ile Ile Phe
              20

(2) INFORMATION FOR SEQ ID NO: 85:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO: 85:

```
      Val Tyr Ile Ile Phe Val Tyr Ile Pro Leu Phe Leu Ile His Thr His
      1               5                  10                  15

Ala Arg Phe Leu Ile Thr
                      20
```

(2) INFORMATION FOR SEQ ID NO: 86:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 86:

```
      Ala Asn Pro Ala Gly Thr Asn Gly Glu Glu Gly Thr Gly Cys Asn Gly
      1               5                  10                  15

Trp Phe Tyr Val
                  20
```

(2) INFORMATION FOR SEQ ID NO: 87:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 87:

```
      Gly Trp Phe Tyr Val Glu Ala Val Val Glu Lys Lys Thr Gly Asn Ala
      1               5                  10                  15

Ile Ser Asn Asn
                  20
```

(2) INFORMATION FOR SEQ ID NO: 88:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 88:

```
      Ala Ile Ser Asn Asn Glu Asn Glu Asn Ser Asn Thr Gly Glu Asn
      1               5                  10                  15

Leu Val Asn Phe
                  20
```

(2) INFORMATION FOR SEQ ID NO: 89:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 89:

```
      Asn Leu Val Asn Phe Ile Val Asn Asn Asn Tyr Leu Thr Gln Ala
      1               5                  10                  15

Glu Thr Glu Thr
                  20
```

(2) INFORMATION FOR SEQ ID NO: 90:

(i) SEQUENCE CHARACTERISTICS:
    (A) LENGTH: 20 amino acids
    (B) TYPE: amino acid
    (D) TOPOLOGY: linear (ii) MOLECULE TYPE: peptide (xi) SEQUENCE DESCRIPTION: SEQ ID NO: 90:

Ala Glu Thr Glu Thr Ala His Ala Leu Phe Thr Ala Gln Glu Ala Lys
  1               5                  10                  15

Gln His Arg Asn
              20

(2) INFORMATION FOR SEQ ID NO: 91:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 91:

Lys Gln His Arg Asn Ala Val Gln Val Leu Lys Arg Lys Tyr Leu Gly
      1               5                  10                  15

Ser Cys Ile Glu
                  20

(2) INFORMATION FOR SEQ ID NO: 92:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 92:

Gly Ser Cys Ile Glu Lys Gln Ser Arg Ala Ala Lys Arg Arg Leu Phe
      1               5                  10                  15

Glu Ser Glu Asn
                  20

(2) INFORMATION FOR SEQ ID NO: 93:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 93:

Phe Glu Ser Glu Asn Ser Gly Tyr Gly Asn Thr Glu Val Glu Thr Gln
      1               5                  10                  15

Gln Met Leu Gln Val
                  20

(2) INFORMATION FOR SEQ ID NO: 94:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO: 94:

```
Leu Gln Val Glu Gly Arg His Glu Thr Glu Thr Pro Cys Ser Gln Tyr
1               5                   10                  15

Ser Gly Gly
```

(2) INFORMATION FOR SEQ ID NO: 95:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 95:

```
Gln Tyr Ser Gly Gly Ser Gly Gly Cys Ser Gln Tyr Ser Ser Gly
1               5                   10                  15

Ser Gly Gly Glu
            20
```

(2) INFORMATION FOR SEQ ID NO: 96:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 96:

```
Gly Ser Gly Gly Glu Gly Val Ser Glu Arg His Thr Ile Cys Gln Thr
1               5                   10                  15

Pro Leu Thr Asn
            20
```

(2) INFORMATION FOR SEQ ID NO: 97:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 97:

```
Thr Pro Leu Thr Asn Ile Leu Asn Val Leu Lys Thr Ser Asn Ala Lys
1               5                   10                  15

Ala Ala Met Leu
            20
```

(2) INFORMATION FOR SEQ ID NO: 98:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 98:

```
Lys Ala Ala Met Leu Ala Lys Phe Lys Glu Leu Tyr Gly Val Ser Phe
1               5                   10                  15

Ser Glu Leu Val
            20
```

(2) INFORMATION FOR SEQ ID NO: 99:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 99:

```
Phe Ser Glu Leu Val Arg Pro Phe Lys Ser Asn Arg Ser Thr Cys Cys
 1               5                  10                  15

Asn Trp Cys Ile
            20
```

(2) INFORMATION FOR SEQ ID NO: 100:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 100:

```
Cys Asn Trp Cys Ile Ala Ala Phe Gly Leu Thr Pro Ser Ile Ala Asn
 1               5                  10                  15

Ser Ile Lys Thr
            20
```

(2) INFORMATION FOR SEQ ID NO: 101:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 101:

```
Asn Ser Ile Lys Thr Leu Leu Gln Gln Tyr Cys Leu Tyr Leu His Ile
 1               5                  10                  15

Gln Ser Leu Ala
            20
```

(2) INFORMATION FOR SEQ ID NO: 102:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 102:

```
Ile Gln Ser Leu Ala Cys Ser Trp Gly Met Val Val Leu Leu Leu Val
 1               5                  10                  15

Arg Tyr Lys Cys
            20
```

(2) INFORMATION FOR SEQ ID NO: 103:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 103:

Val Arg Tyr Lys Cys Gly Lys Asn Arg Glu Thr Ile Glu Lys Leu Leu
  1              5                   10               15

Ser Lys Leu Leu
              20

(2) INFORMATION FOR SEQ ID NO: 104:

(i) SEQUENCE CHARACTERISTICS:
    (A) LENGTH: 20 amino acids
    (B) TYPE: amino acid
    (D) TOPOLOGY: linear (ii) MOLECULE TYPE: peptide (xi) SEQUENCE DESCRIPTION: SEQ ID NO: 104:

Leu Ser Lys Leu Leu Cys Val Ser Pro Met Cys Met Met Ile Glu Pro
  1              5                   10               15

Pro Lys Leu Arg
              20

(2) INFORMATION FOR SEQ ID NO: 105:

(i) SEQUENCE CHARACTERISTICS:
    (A) LENGTH: 20 amino acids
    (B) TYPE: amino acid
    (D) TOPOLOGY: linear (ii) MOLECULE TYPE: peptide (xi) SEQUENCE DESCRIPTION: SEQ ID NO: 105:

Pro Pro Lys Leu Arg Ser Thr Ala Ala Ala Leu Tyr Trp Tyr Lys Thr
  1              5                   10               15

Gly Ile Ser Asn
              20

(2) INFORMATION FOR SEQ ID NO: 106:

(i) SEQUENCE CHARACTERISTICS:
    (A) LENGTH: 20 amino acids
    (B) TYPE: amino acid
    (D) TOPOLOGY: linear (ii) MOLECULE TYPE: peptide (xi) SEQUENCE DESCRIPTION: SEQ ID NO: 106:

Thr Gly Ile Ser Asn Ile Ser Glu Val Tyr Gly Asn Thr Pro Glu Trp
  1              5                   10               15

Ile Gln Arg Gln
              20

(2) INFORMATION FOR SEQ ID NO: 107:

(i) SEQUENCE CHARACTERISTICS:
    (A) LENGTH: 20 amino acids
    (B) TYPE: amino acid
    (D) TOPOLOGY: linear (ii) MOLECULE TYPE: peptide (xi) SEQUENCE DESCRIPTION: SEQ ID NO: 107:

Trp Ile Gln Arg Gln Thr Val Leu Gln His Ser Phe Asn Asn Cys Thr
  1              5                   10               15

Phe Glu Leu Ser
              20

(2) INFORMATION FOR SEQ ID NO: 108:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 108:

```
Thr Phe Glu Leu Ser Gln Met Val Gln Trp Ala Tyr Asn Asn Asn Ile
 1               5                  10                  15

Val Asn Asn Ser
            20
```

(2) INFORMATION FOR SEQ ID NO: 109:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 109:

```
Ile Val Asn Asn Ser Glu Ile Ala Tyr Lys Tyr Ala Gln Leu Ala Asn
 1               5                  10                  15

Thr Asn Ser Asn
            20
```

(2) INFORMATION FOR SEQ ID NO: 110:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 110:

```
Asn Thr Asn Ser Asn Ala Ser Ala Phe Leu Lys Ser Asn Ser Gln Ala
 1               5                  10                  15

Lys Ile Val Lys
            20
```

(2) INFORMATION FOR SEQ ID NO: 111:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 111:

```
Ala Lys Ile Val Lys Asn Cys Ala Thr Met Cys Arg His Tyr Lys Arg
 1               5                  10                  15

Ala Glu Lys Lys
            20
```

(2) INFORMATION FOR SEQ ID NO: 112:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 112:

```
Arg Ala Glu Lys Lys Gln Met Ser Met Ser Gln Trp Ile Lys Tyr Arg
1               5                   10                  15

Cys Asn Arg Val
            20
```

(2) INFORMATION FOR SEQ ID NO: 113:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 113:

```
Arg Cys Asn Arg Val Asn Asn Gly Gly Asn Trp Lys Gln Ile Val Met
1               5                   10                  15

Phe Leu Arg Tyr
            20
```

(2) INFORMATION FOR SEQ ID NO: 114:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 114:

```
Met Phe Leu Arg Tyr Gln Gly Val Glu Phe Met Ser Phe Leu Thr Ala
1               5                   10                  15

Leu Lys Arg Phe
            20
```

(2) INFORMATION FOR SEQ ID NO: 115:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 115:

```
Ala Leu Lys Arg Phe Leu Gln Gly Ile Pro Lys Lys Asn Cys Ile Leu
1               5                   10                  15

Leu Tyr Gly Ala
            20
```

(2) INFORMATION FOR SEQ ID NO: 116:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 116:

```
Leu Leu Tyr Gly Ala Ala Asn Thr Gly Lys Ser Leu Phe Gly Met Ser
1               5                   10                  15
```

```
      Leu Met Lys Phe
              20
```

(2) INFORMATION FOR SEQ ID NO: 117:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 117:

```
      Ser Leu Met Lys Phe Leu Gln Gly Ser Val Ile Cys Phe Val Asn Ser
      1               5                  10                  15

Lys Ser His Phe
              20
```

(2) INFORMATION FOR SEQ ID NO: 118:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 118:

```
      Ser Lys Ser His Phe Trp Leu Gln Pro Leu Ala Asn Ala Lys Ile Gly
      1               5                  10                  15

Met Leu Asn Asn
              20
```

(2) INFORMATION FOR SEQ ID NO: 119:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 119:

```
      Gly Met Leu Asn Asn Ala Thr Val Pro Cys Trp Asn Tyr Ile Asn Asn
      1               5                  10                  15

Asn Leu Arg Asn
              20
```

(2) INFORMATION FOR SEQ ID NO: 120:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 120:

```
      Asn Asn Leu Arg Asn Ala Leu Asn Gly Asn Leu Val Ser Met Asn Val
      1               5                  10                  15

Lys His Arg Pro
              20
```

(2) INFORMATION FOR SEQ ID NO: 121:

(i) SEQUENCE CHARACTERISTICS:
        (A) LENGTH: 20 amino acids (B) TYPE: amino acid
            (D) TOPOLOGY: linear (ii) MOLECULE TYPE: peptide (xi) SEQUENCE DESCRIPTION: SEQ ID NO: 121:

Val Lys His Arg Pro Leu Val Gln Leu Lys Cys Pro Pro Leu Leu Ile
      1               5                   10                  15

Thr Ser Asn Ile
                  20

(2) INFORMATION FOR SEQ ID NO: 122:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 122:

Ile Thr Ser Asn Ile Asn Ala Gly Thr Asn Ser Arg Trp Pro Tyr Leu
      1               5                   10                  15

His Asn Arg Leu
                  20

(2) INFORMATION FOR SEQ ID NO: 123:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 123:

Leu His Asn Arg Leu Val Val Phe Thr Phe Pro Asn Glu Phe Pro Phe
      1               5                   10                  15

Asn Glu Asn Gly
                  20

(2) INFORMATION FOR SEQ ID NO: 124:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO: 124:

Phe Asn Glu Asn Gly Asn Pro Val Tyr Glu Leu Asn Asn Lys Asn Trp
      1               5                   10                  15

Lys Ser (2) INFORMATION FOR SEQ ID NO: 125:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO: 125:

Lys Asn Trp Lys Ser Phe Phe Ser Arg Thr Trp Ser Arg Leu Ser Leu
      1               5                   10                  15

His Glu (2) INFORMATION FOR SEQ ID NO: 126:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO: 126:

Leu Ser Leu His Glu Asn Glu Asn Lys Glu Asn Asn Gly Asn Ser Leu
    1               5                   10                  15

Pro Thr (2) INFORMATION FOR SEQ ID NO: 127:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO: 127:

Asn Ser Leu Pro Thr Phe Lys Cys Val Ser Gly Gln Asn Thr Asn Thr
    1               5                   10                  15

Leu (2) INFORMATION FOR SEQ ID NO: 128:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO: 128:

Glu Thr Leu Cys Gln Arg Leu Asn Val Cys Gln Asn Lys Ile Leu Thr
    1               5                   10                  15

His Tyr Glu (2) INFORMATION FOR SEQ ID NO: 129:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 129:

Leu Thr His Tyr Glu Asn Asn Ser Thr Asn Leu Arg Asn His Ile Asn
    1               5                   10                  15

Tyr Trp Lys His
                20

(2) INFORMATION FOR SEQ ID NO: 130:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 130:

```
Asn Tyr Trp Lys His Met Arg Leu Glu Cys Ala Ile Tyr Tyr Lys Ala
1               5                  10                 15

Arg Glu Met Gly
            20
```

(2) INFORMATION FOR SEQ ID NO: 131:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 131:

```
Ala Arg Glu Met Gly Phe Lys His Ile Asn His Gln Val Val Pro Thr
1               5                  10                 15

Leu Ala Val Ser
            20
```

(2) INFORMATION FOR SEQ ID NO: 132:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 132:

```
Thr Leu Ala Val Ser Lys Asn Lys Ala Leu Gln Ala Ile Glu Leu Gln
1               5                  10                 15

Leu Thr Leu Glu
            20
```

(2) INFORMATION FOR SEQ ID NO: 133:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 133:

```
Gln Leu Thr Leu Glu Thr Ile Tyr Asn Ser Gln Tyr Ser Asn Glu Lys
1               5                  10                 15

Trp Thr Leu Gln
            20
```

(2) INFORMATION FOR SEQ ID NO: 134:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 134:

```
Lys Trp Thr Leu Gln Asn Val Ser Leu Glu Val Tyr Leu Thr Ala Pro
1               5                  10                 15

Thr Gly Cys Ile
```

20

(2) INFORMATION FOR SEQ ID NO: 135:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 135:

Pro Thr Gly Cys Ile Lys Lys His Gly Tyr Thr Val Glu Val Gln Phe
      1               5                  10                  15

Asn Gly Asn Ile
                  20

(2) INFORMATION FOR SEQ ID NO: 136:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 136:

Phe Asn Gly Asn Ile Cys Asn Thr Met His Tyr Thr Asn Trp Thr His
      1               5                  10                  15

Ile Tyr Ile Cys
                  20

(2) INFORMATION FOR SEQ ID NO: 137:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO: 137:

His Tyr Ile Cys Glu Glu Ala Ser Val Thr Val Val Glu Gly Gln Val
      1               5                  10                  15

Asn Tyr Tyr (2) INFORMATION FOR SEQ ID NO: 138:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 138:

Gln Val Asn Tyr Tyr Gly Leu Tyr Tyr Val His Glu Gly Ile Arg Thr
      1               5                  10                  15

Tyr Phe Val Gln
                  20

(2) INFORMATION FOR SEQ ID NO: 139:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 139:

Thr Tyr Phe Val Gln Phe Lys Asn Asn Ala Glu Lys Tyr Ser Lys Asn
           1               5                   10                  15

Lys Val Trp Glu
                       20

(2) INFORMATION FOR SEQ ID NO: 140:

(i) SEQUENCE CHARACTERISTICS:
           (A) LENGTH: 20 amino acids
           (B) TYPE: amino acid
           (D) TOPOLOGY: linear (ii) MOLECULE TYPE: peptide (xi) SEQUENCE DESCRIPTION: SEQ ID NO: 140:

Asn Lys Val Trp Glu Val His Ala Gly Gly Gln Val Ile Leu Cys Pro
           1               5                   10                  15

Thr Ser Val Phe
                       20

(2) INFORMATION FOR SEQ ID NO: 141:

(i) SEQUENCE CHARACTERISTICS:
           (A) LENGTH: 20 amino acids
           (B) TYPE: amino acid
           (D) TOPOLOGY: linear (ii) MOLECULE TYPE: peptide (xi) SEQUENCE DESCRIPTION: SEQ ID NO: 141:

Pro Thr Ser Val Phe Ser Ser Asn Glu Val Ser Ser Pro Glu Ile Ile
           1               5                   10                  15

Arg Gln His Leu
                       20

(2) INFORMATION FOR SEQ ID NO: 142:

(i) SEQUENCE CHARACTERISTICS:
           (A) LENGTH: 20 amino acids
           (B) TYPE: amino acid
           (D) TOPOLOGY: linear (ii) MOLECULE TYPE: peptide (xi) SEQUENCE DESCRIPTION: SEQ ID NO: 142:

Ile Arg Gln His Leu Ala Asn His Pro Ala Ala Thr His Thr Lys Ala
           1               5                   10                  15

Val Ala Leu Gly
                       20

(2) INFORMATION FOR SEQ ID NO: 143:

(i) SEQUENCE CHARACTERISTICS:
           (A) LENGTH: 20 amino acids
           (B) TYPE: amino acid
           (D) TOPOLOGY: linear (ii) MOLECULE TYPE: peptide (xi) SEQUENCE DESCRIPTION: SEQ ID NO: 143:

Ala Val Ala Leu Gly Thr Glu Glu Thr Gln Thr Thr Ile Gln Arg Pro
           1               5                   10                  15

Arg Ser Glu Pro
                20

(2) INFORMATION FOR SEQ ID NO: 144:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 144:

Pro Arg Ser Glu Pro Asn Thr Gly Asn Pro Cys His Thr Thr Lys Leu
        1               5                   10                  15

Leu His Arg Asn
                20

(2) INFORMATION FOR SEQ ID NO: 145:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 145:

Leu Leu His Arg Asn Ser Val Asn Ser Ala Pro Ile Leu Thr Ala Phe
        1               5                   10                  15

Asn Ser Ser His
                20

(2) INFORMATION FOR SEQ ID NO: 146:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 146:

Phe Asn Ser Ser His Lys Gly Arg Ile Asn Cys Asn Ser Asn Thr Thr
        1               5                   10                  15

Pro Ile Val His
                20

(2) INFORMATION FOR SEQ ID NO: 147:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 147:

Thr Pro Ile Val His Leu Lys Gly Asn Ala Asn Thr Leu Lys Cys Leu
        1               5                   10                  15

Arg Tyr Arg Phe
                20

(2) INFORMATION FOR SEQ ID NO: 148:

(i) SEQUENCE CHARACTERISTICS:
        (A) LENGTH: 20 amino acids (B) TYPE: amino acid
        (D) TOPOLOGY: linear (ii) MOLECULE TYPE: peptide (xi) SEQUENCE DESCRIPTION: SEQ ID NO: 148:

Leu Arg Tyr Arg Phe Lys Lys His Cys Thr Leu Tyr Thr Ala Val Ser
       1               5                   10                  15

Ser Thr Trp His
                   20

(2) INFORMATION FOR SEQ ID NO: 149:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 149:

Ser Ser Thr Trp His Trp Thr Gly His Asn Val Lys His Lys Ser Ala
       1               5                   10                  15

Ile Val Thr Leu
                   20

(2) INFORMATION FOR SEQ ID NO: 150:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 150:

Ala Ile Val Thr Leu Thr Tyr Asn Ser Glu Trp Gln Arg Asn Gln Phe
       1               5                   10                  15

Leu Ser Gln Val
                   20

(2) INFORMATION FOR SEQ ID NO: 151:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 151:

Phe Leu Ser Gln Val Lys Ile Pro Lys Thr Ile Thr Val Ser Thr Gly
       1               5                   10                  15

Phe Met Ser Ile
                   20

(2) INFORMATION FOR SEQ ID NO: 152:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 152:

His Gly Asn Thr Pro Thr Leu His Glu Tyr Met Leu Asn Leu Gln Pro

```
            1               5              10              15

Glu Thr Thr Asn
                    20

(2) INFORMATION FOR SEQ ID NO: 153:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 153:

Pro Glu Thr Thr Asn Leu Tyr Cys Tyr Glu Gln Leu Asn Asn Ser Ser
        1               5                  10                  15

Glu Glu Glu Asn
                    20

(2) INFORMATION FOR SEQ ID NO: 154:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 154:

Ser Glu Glu Glu Asn Glu Ile Asn Gly Pro Ala Gly Gln Ala Glu Pro
        1               5                  10                  15

Asn Arg Ala His
                    20

(2) INFORMATION FOR SEQ ID NO: 155:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 155:

Pro Asn Arg Ala His Tyr Asn Ile Val Thr Phe Cys Cys Lys Cys Asn
        1               5                  10                  15

Ser Thr Leu Arg
                    20

(2) INFORMATION FOR SEQ ID NO: 156:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 156:

Asn Ser Thr Leu Arg Leu Cys Val Gln Ser Thr His Val Asn Ile Arg
        1               5                  10                  15

Thr Leu Glu Asn Leu
                    20

(2) INFORMATION FOR SEQ ID NO: 157:
```

```
    (i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 157:

Thr Leu Glu Asn Leu Leu Met Gly Thr Leu Gly Ile Val Cys Pro Ile
      1               5                  10                  15

Cys Ser Gln Lys Pro
                  20

(2) INFORMATION FOR SEQ ID NO: 158:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 158:

His Gln Lys Arg Thr Ala Met Phe Gln Asn Pro Gln Glu Arg Pro Arg
      1               5                  10                  15

Lys Leu Pro Gln
                  20

(2) INFORMATION FOR SEQ ID NO: 159:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 159:

Arg Lys Leu Pro Gln Leu Cys Thr Glu Leu Gln Thr Thr Ile His Asn
      1               5                  10                  15

Ile Ile Leu Glu
                  20

(2) INFORMATION FOR SEQ ID NO: 160:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 160:

Asn Ile Ile Leu Glu Cys Val Tyr Cys Lys Gln Gln Leu Leu Arg Arg
      1               5                  10                  15

Glu Val Tyr Asn
                  20

(2) INFORMATION FOR SEQ ID NO: 161:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 161:
```

```
    Arg Glu Val Tyr Asn Phe Ala Phe Arg Asn Leu Cys Ile Val Tyr Arg
    1               5                   10                  15

Asn Gly Asn Pro
                20
```

(2) INFORMATION FOR SEQ ID NO: 162:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 162:

```
    Arg Asn Gly Asn Pro Tyr Ala Val Cys Asn Lys Cys Leu Lys Phe Tyr
    1               5                   10                  15

Ser Lys Ile Ser
                20
```

(2) INFORMATION FOR SEQ ID NO: 163:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 163:

```
    Tyr Ser Lys Ile Ser Glu Tyr Arg His Tyr Cys Tyr Ser Leu Tyr Gly
    1               5                   10                  15

Thr Thr Leu Glu
                20
```

(2) INFORMATION FOR SEQ ID NO: 164:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 164:

```
    Gly Thr Thr Leu Glu Gln Gln Tyr Asn Lys Pro Leu Cys Asn Leu Leu
    1               5                   10                  15

Ile Arg Cys Ile
                20
```

(2) INFORMATION FOR SEQ ID NO: 165:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 165:

```
    Leu Ile Arg Cys Ile Asn Cys Gln Lys Pro Leu Cys Pro Glu Glu Lys
    1               5                   10                  15

Gln Arg His Leu
                20
```

(2) INFORMATION FOR SEQ ID NO: 166:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 166:

Lys Gln Arg His Leu Asn Lys Lys Gln Arg Phe His Asn Ile Arg Gly
    1               5                   10                  15

Arg Trp Thr Gly Arg
                20

(2) INFORMATION FOR SEQ ID NO: 167:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 167:

Arg Trp Thr Gly Arg Cys Met Ser Cys Arg Ser Ser Arg Thr Arg
    1               5                   10                  15

Arg Glu Thr Gln Leu
                20

(2) INFORMATION FOR SEQ ID NO: 168:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 168:

Tyr Tyr Val Leu His Leu Cys Leu Ala Ala Thr Lys Tyr Pro Leu Leu
    1               5                   10                  15

Lys Leu Leu Gly
                20

(2) INFORMATION FOR SEQ ID NO: 169:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 169:

Leu Lys Leu Leu Gly Ser Thr Trp Pro Thr Thr Pro Pro Arg Pro Ile
    1               5                   10                  15

Pro Lys Pro Ser
                20

(2) INFORMATION FOR SEQ ID NO: 170:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 170:

Ile Pro Lys Pro Ser Pro Trp Ala Pro Lys Lys His Arg Arg Leu Ser
    1               5                   10                  15

Ser Asn Gln Asn
                20

(2) INFORMATION FOR SEQ ID NO: 171:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 171:

Ser Ser Asn Gln Asn Gln Ser Gln Thr Pro Glu Thr Pro Ala Thr Pro
    1               5                   10                  15

Leu Ser Cys Cys
                20

(2) INFORMATION FOR SEQ ID NO: 172:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 172:

Pro Leu Ser Cys Cys Thr Glu Thr Gln Trp Thr Val Leu Gln Ser Ser
    1               5                   10                  15

Leu His Leu Thr
                20

(2) INFORMATION FOR SEQ ID NO: 173:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 173:

Ser Leu His Leu Thr Ala His Thr Lys Asn Gly Leu Thr Val Ile Val
    1               5                   10                  15

Thr Leu His Pro
                20

(2) INFORMATION FOR SEQ ID NO: 174:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 174:

Val Thr Gln Ala Ile Ala Cys Gln Lys His Thr Pro Pro Ala Pro Lys
    1               5                   10                  15

Glu Asp Asp Pro Leu
                20

(2) INFORMATION FOR SEQ ID NO: 175:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 175:

```
Gly Gly Thr Leu Glu Asp Thr Tyr Arg Phe Val Thr Gln Ala Ile Ala
 1               5                  10                  15

Cys Gln Lys His
            20
```

(2) INFORMATION FOR SEQ ID NO: 176:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 176:

```
Ala Cys Gln Lys His Thr Pro Pro Ala Pro Lys Glu Asp Asp Pro Leu
 1               5                  10                  15

Lys Lys Tyr Thr
            20
```

(2) INFORMATION FOR SEQ ID NO: 177:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 177:

```
Val Gln Phe Asp Gly Asp Ile Cys Asn Thr Met His Tyr Thr Asn Trp
 1               5                  10                  15

Thr His Ile Tyr
            20
```

(2) INFORMATION FOR SEQ ID NO: 178:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 178:

```
Gly Asp Ile Cys Asn Thr Met His Tyr Thr Asn Trp Thr His Ile Trp
 1               5                  10                  15

Ile Cys Glu Glu
            20
```

(2) INFORMATION FOR SEQ ID NO: 179:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 179:

Val His Thr Gly Phe Gly Ala Met Asp Pro Thr Thr Leu Gln Ala Asn
        1               5                   10                  15

Lys Ser Glu Val
                    20

(2) INFORMATION FOR SEQ ID NO: 180:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 180:

Gly Gly Thr Leu Glu Asp Thr Tyr Arg Phe Val Thr Gln Ala Ile Ala
        1               5                   10                  15

Cys Gln Lys His
                    20

(2) INFORMATION FOR SEQ ID NO: 181:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 181:

Ala Cys Gln Lys His Thr Pro Pro Ala Pro Lys Glu Asp Asp Pro Leu
        1               5                   10                  15

Lys Lys Tyr Thr
                    20

(2) INFORMATION FOR SEQ ID NO: 182:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 182:

Leu Lys Lys Tyr Thr Phe Tyr Glu Val Asn Leu Lys Glu Lys Phe Ser
        1               5                   10                  15

Ala Asp Leu Asp
                    20

(2) INFORMATION FOR SEQ ID NO: 183:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO: 183:

Ser Ala Asp Leu Asp Gln Phe Pro Leu Gly Arg Lys Phe Leu Leu Gly
        1               5                   10                  15

Gly Cys (2) INFORMATION FOR SEQ ID NO: 184:

(i) SEQUENCE CHARACTERISTICS:
        (A) LENGTH: 18 amino acids
        (B) TYPE: amino acid
        (C) TOPOLOGY: linear (ii) MOLECULE TYPE: peptide (xi) SEQUENCE DESCRIPTION: SEQ ID NO: 184:

```
  Val His Thr Gly Phe Gly Ala Met Asp Pro Thr Thr Leu Gln Ala Asn
  1               5                   10                  15

Lys Ser
```

(2) INFORMATION FOR SEQ ID NO: 185:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO: 185:

```
  Cys Xaa Xaa Cys Xaa Xaa Xaa Xaa Xaa Xaa Xaa Xaa Xaa Xaa Xaa
  1               5                   10                  15

Xaa Xaa Xaa Xaa Xaa Xaa Xaa Xaa Leu Leu Xaa Xaa Xaa Leu
                  20                  25                  30
```

(2) INFORMATION FOR SEQ ID NO: 186:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO: 186:

```
  Cys Arg Asn Cys Glu Val Lys Leu Arg Ile Phe Val His Ala Thr Glu
  1               5                   10                  15

Phe Gly Ile Arg Ala Phe Gln Gln Leu Leu Thr Gly Asp Leu
                  20                  25                  30
```

(2) INFORMATION FOR SEQ ID NO: 187:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 187:

```
  Arg Leu Ser Ser Asp Gln Asp Gln Ser Gln Thr Pro Glu Thr Pro Ala
  1               5                   10                  15

Thr Pro Leu Ser
                  20
```

(2) INFORMATION FOR SEQ ID NO: 188:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 188:

```
Asp Gln Asp Gln Ser Gln Thr Pro Glu Thr Pro Ala Thr Pro Leu Ser
1               5                   10                  15
Cys Cys Thr Glu
            20
```

(2) INFORMATION FOR SEQ ID NO: 189:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 189:

```
Asp Gln Asp Gln Ser Gln Thr Pro Glu Thr Pro
1               5                   10
```

(2) INFORMATION FOR SEQ ID NO: 190:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO: 190:

```
Lys His Arg Arg Leu Ser Ser Asp Gln Asp Gln Ser Gln Thr Pro Glu
1               5                   10                  15
Thr Pro Ala Thr Pro Leu Ser Cys Cys Thr Glu Thr Gln Trp
            20                  25                  30
```

(2) INFORMATION FOR SEQ ID NO: 191:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO: 191:

```
Gln Ser Gln Thr Pro Glu Thr Pro Ala Thr Pro Leu Ser Cys Cys Thr
1               5                   10                  15
Glu Thr Gln Trp Thr Val Leu Gln Ser Ser Leu His Leu Thr
            20                  25                  30
```

(2) INFORMATION FOR SEQ ID NO: 192:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO: 192:

```
Thr Glu Thr Gln Trp Thr Val Leu Gln Ser Ser Leu His Leu Thr Ala
1               5                   10                  15
His Thr Lys Asp Gly Leu Thr Val Ile Val Thr Leu His Pro
            20                  25                  30
```

(2) INFORMATION FOR SEQ ID NO: 193:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO: 193:

```
Lys His Arg Arg Leu Ser Ser Asp Gln Asp Gln Ser Gln Thr Pro Glu
 1               5                  10                  15

Thr Pro Ala Thr Pro Leu Ser Cys Cys Thr Glu Thr Gln Trp
            20                  25                  30
```